US009820949B2

(12) United States Patent
Desai et al.

(10) Patent No.: US 9,820,949 B2
(45) Date of Patent: *Nov. 21, 2017

(54) METHODS OF TREATMENT OF PANCREATIC CANCER

(71) Applicant: Abraxis BioScience, LLC, Los Angeles, CA (US)

(72) Inventors: Neil P. Desai, Los Angeles, CA (US); Patrick Soon-Shiong, Los Angeles, CA (US)

(73) Assignee: ABRAXIS BIOSCIENCE, LLC, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/192,077

(22) Filed: Jun. 24, 2016

(65) Prior Publication Data

US 2017/0049711 A1    Feb. 23, 2017

Related U.S. Application Data

(63) Continuation of application No. 13/701,002, filed as application No. PCT/US2011/037462 on May 20, 2011, now Pat. No. 9,399,071.

(60) Provisional application No. 61/446,932, filed on Feb. 25, 2011, provisional application No. 61/377,035, filed on Aug. 25, 2010, provisional application No. 61/351,846, filed on Jun. 4, 2010.

(51) Int. Cl.

| | |
|---|---|
| *A61K 9/51* | (2006.01) |
| *A61K 45/06* | (2006.01) |
| *A61K 47/48* | (2006.01) |
| *A61K 31/519* | (2006.01) |
| *A61K 31/436* | (2006.01) |
| *A61K 31/4745* | (2006.01) |
| *A61K 31/506* | (2006.01) |
| *A61K 31/513* | (2006.01) |
| *A61K 31/337* | (2006.01) |
| *A61K 31/16* | (2006.01) |
| *A61K 31/4709* | (2006.01) |
| *A61K 31/517* | (2006.01) |
| *A61K 31/5377* | (2006.01) |
| *A61K 31/69* | (2006.01) |
| *A61K 31/7068* | (2006.01) |
| *A61K 39/395* | (2006.01) |

(52) U.S. Cl.
CPC ............ *A61K 9/5169* (2013.01); *A61K 31/16* (2013.01); *A61K 31/337* (2013.01); *A61K 31/436* (2013.01); *A61K 31/4709* (2013.01); *A61K 31/4745* (2013.01); *A61K 31/506* (2013.01); *A61K 31/513* (2013.01); *A61K 31/517* (2013.01); *A61K 31/519* (2013.01); *A61K 31/5377* (2013.01); *A61K 31/69* (2013.01); *A61K 31/7068* (2013.01); *A61K 39/3955* (2013.01); *A61K 45/06* (2013.01); *A61K 47/48284* (2013.01)

(58) Field of Classification Search
CPC .............. A61K 2300/00; A61K 31/337; A61K 31/7068; A61K 9/5169; A61K 45/06; A61K 47/48284; A61K 31/519; A61K 31/436; A61K 31/4745; A61K 31/506; A61K 31/513; A61K 31/4709; A61K 31/5377; A61K 31/69; A61K 39/3955
See application file for complete search history.

(56) References Cited

U.S. PATENT DOCUMENTS

| | | |
|---|---|---|
| 5,362,478 A | 11/1994 | Desai et al. |
| 5,439,686 A | 8/1995 | Desai et al. |
| 5,470,571 A | 11/1995 | Herlyn et al. |
| 5,498,421 A | 3/1996 | Grinstaff et al. |
| 5,505,932 A | 4/1996 | Grinstaff et al. |
| 5,508,021 A | 4/1996 | Grinstaff et al. |
| 5,510,118 A | 4/1996 | Bosch et al. |
| 5,512,268 A | 4/1996 | Grinstaff et al. |
| 5,534,270 A | 7/1996 | De Castro |
| 5,558,864 A | 9/1996 | Bendig et al. |
| 5,560,933 A | 10/1996 | Soon-Shiong et al. |
| 5,635,207 A | 6/1997 | Grinstaff et al. |
| 5,639,473 A | 6/1997 | Grinstaff et al. |
| 5,650,156 A | 7/1997 | Grinstaff et al. |
| 5,651,986 A | 7/1997 | Brem et al. |
| 5,662,883 A | 9/1997 | Bagchi et al. |
| 5,665,382 A | 9/1997 | Grinstaff et al. |
| 5,665,383 A | 9/1997 | Grinstaff et al. |

(Continued)

FOREIGN PATENT DOCUMENTS

| | | |
|---|---|---|
| CN | 101601123 A | 12/2009 |
| EP | 0 584 001 A1 | 2/1994 |
| EP | 1 650 220 B1 | 9/2007 |
| EP | 1 862 179 A1 | 12/2007 |
| RU | 2006112834 A | 10/2007 |

(Continued)

OTHER PUBLICATIONS

US 8,968,752, 03/2015, Desai et al. (withdrawn)

(Continued)

*Primary Examiner* — Snigdha Maewall
(74) *Attorney, Agent, or Firm* — Morrison & Foerster LLP

(57) ABSTRACT

The present invention provides methods and compositions for treating pancreatic cancer in an individual who has been previously treated for pancreatic cancer (e.g., gemcitabine-based therapy) by administering a composition comprising nanoparticles that comprise a taxane and an albumin. The invention also provides combination therapy methods of treating pancreatic cancer (for example, in an individual who has been previously treated for pancreatic cancer) comprising administering to an individual an effective amount of a composition comprising nanoparticles that comprise a taxane and an albumin and another agent.

48 Claims, 4 Drawing Sheets

(56) References Cited

U.S. PATENT DOCUMENTS

| | | |
|---|---|---|
| 5,690,928 A | 11/1997 | Heimbrook et al. |
| 5,733,925 A | 3/1998 | Kunz et al. |
| 5,744,460 A | 4/1998 | Müller et al. |
| 5,859,018 A | 1/1999 | Brown et al. |
| 5,873,904 A | 2/1999 | Ragheb et al. |
| 5,886,026 A | 3/1999 | Hunter et al. |
| 5,916,596 A | 6/1999 | Desai et al. |
| 5,977,163 A | 11/1999 | Li et al. |
| 5,981,568 A | 11/1999 | Kunz et al. |
| 5,994,341 A | 11/1999 | Hunter et al. |
| 5,997,904 A | 12/1999 | Magdassi et al. |
| 6,096,070 A | 8/2000 | Ragheb et al. |
| 6,096,331 A | 8/2000 | Desai et al. |
| 6,143,276 A | 11/2000 | Unger |
| 6,239,124 B1 | 5/2001 | Zenke et al. |
| 6,268,390 B1 | 7/2001 | Kunz |
| 6,306,421 B1 | 10/2001 | Kunz et al. |
| 6,506,405 B1 | 1/2003 | Desai et al. |
| 6,515,009 B1 | 2/2003 | Kunz et al. |
| 6,528,067 B1 | 3/2003 | Magdassi et al. |
| 6,537,579 B1 | 3/2003 | Desai et al. |
| 6,544,544 B2 | 4/2003 | Hunter et al. |
| 6,548,531 B2 | 4/2003 | Breimer et al. |
| 6,565,842 B1 | 5/2003 | Desai et al. |
| 6,566,405 B2 | 5/2003 | Weidner et al. |
| 6,569,441 B2 | 5/2003 | Kunz et al. |
| 6,652,884 B2 | 11/2003 | Falciani |
| 6,682,758 B1 | 1/2004 | Tabibi et al. |
| 6,689,803 B2 | 2/2004 | Hunter |
| 6,727,256 B1 | 4/2004 | Carter et al. |
| 6,730,699 B2 | 5/2004 | Li et al. |
| 6,749,868 B1 | 6/2004 | Desai et al. |
| 6,752,803 B2 | 6/2004 | Goldman et al. |
| 6,753,006 B1 | 6/2004 | Desai et al. |
| 6,872,715 B2 | 3/2005 | Santi et al. |
| 6,884,817 B2 | 4/2005 | Li et al. |
| 6,884,879 B1 | 4/2005 | Baca et al. |
| 6,929,818 B2 | 8/2005 | Luthra et al. |
| 6,946,456 B2 | 9/2005 | Rosen et al. |
| 7,038,071 B2 | 5/2006 | Lal |
| 7,101,568 B2 | 9/2006 | Dang et al. |
| 7,129,368 B2 | 10/2006 | Lal et al. |
| 7,141,576 B2 | 11/2006 | Lackey et al. |
| 7,232,919 B2 | 6/2007 | Lal |
| 7,332,568 B2 | 2/2008 | Trieu et al. |
| 7,405,208 B2 | 7/2008 | Santi et al. |
| 7,758,891 B2 | 7/2010 | Desai et al. |
| 7,771,751 B2 | 8/2010 | Desai et al. |
| 7,780,984 B2 | 8/2010 | Desai et al. |
| 7,820,788 B2 | 10/2010 | Desai et al. |
| 7,923,536 B2 | 4/2011 | Desai et al. |
| 7,981,445 B2 | 7/2011 | De et al. |
| 8,034,375 B2 | 10/2011 | Desai et al. |
| 8,034,765 B2 | 10/2011 | De et al. |
| 8,137,684 B2 | 3/2012 | Desai et al. |
| 8,138,229 B2 | 3/2012 | Desai et al. |
| 8,257,733 B2 | 9/2012 | Desai et al. |
| 8,268,348 B2 | 9/2012 | Desai et al. |
| 8,314,156 B2 | 11/2012 | Desai et al. |
| 8,735,394 B2 | 5/2014 | Desai et al. |
| 8,846,771 B2 | 9/2014 | Desai et al. |
| 8,853,260 B2 | 10/2014 | Desai et al. |
| 8,911,786 B2 | 12/2014 | Desai et al. |
| 8,927,019 B2 | 1/2015 | Desai et al. |
| 8,999,396 B2 | 4/2015 | Desai et al. |
| 9,012,518 B2 | 4/2015 | Desai et al. |
| 9,012,519 B2 | 4/2015 | Desai et al. |
| 9,061,014 B2 | 6/2015 | Seward et al. |
| 9,101,543 B2 | 8/2015 | Desai et al. |
| 9,149,455 B2 | 10/2015 | Desai et al. |
| 9,308,180 B2 | 4/2016 | De et al. |
| 9,393,318 B2 | 7/2016 | Desai et al. |
| 9,446,003 B2 | 9/2016 | Desai et al. |
| 9,511,046 B2 | 12/2016 | Desai et al. |
| 9,561,288 B2 | 2/2017 | Desai et al. |
| 9,585,960 B2 | 3/2017 | Foss et al. |
| 2002/0031505 A1 | 3/2002 | Bissery |
| 2002/0169140 A1 | 11/2002 | Prendergast |
| 2003/0185894 A1 | 10/2003 | Zenoni et al. |
| 2003/0187062 A1 | 10/2003 | Zenoni et al. |
| 2003/0216369 A1 | 11/2003 | Rosen et al. |
| 2003/0220354 A1 | 11/2003 | McClure et al. |
| 2004/0033271 A1 | 2/2004 | Lederman |
| 2004/0047835 A1 | 3/2004 | Bianco |
| 2004/0053946 A1 | 3/2004 | Lackey et al. |
| 2004/0126400 A1 | 7/2004 | Iversen et al. |
| 2004/0143004 A1 | 7/2004 | Fargnoli et al. |
| 2004/0167079 A1 | 8/2004 | Tidmarsh |
| 2004/0248781 A1 | 12/2004 | Kerbel |
| 2005/0000900 A1 | 1/2005 | Huang et al. |
| 2005/0004002 A1 | 1/2005 | Desai et al. |
| 2005/0032699 A1 | 2/2005 | Holash et al. |
| 2005/0058684 A1 | 3/2005 | Shanley et al. |
| 2005/0095267 A1 | 5/2005 | Campbell et al. |
| 2005/0186208 A1 | 8/2005 | Fyfe et al. |
| 2006/0003931 A1 | 1/2006 | Eigenbrot, Jr. et al. |
| 2006/0013819 A1 | 1/2006 | Kelsey |
| 2006/0062821 A1 | 3/2006 | Simhambhatla et al. |
| 2006/0135486 A1 | 6/2006 | Owa et al. |
| 2006/0165744 A1 | 7/2006 | Jamil et al. |
| 2006/0199248 A1 | 9/2006 | Trieu et al. |
| 2007/0093547 A1 | 4/2007 | Desai et al. |
| 2007/0116774 A1 | 5/2007 | Desai et al. |
| 2007/0117133 A1 | 5/2007 | Trieu et al. |
| 2007/0129448 A1 | 6/2007 | Desai et al. |
| 2007/0166388 A1 | 7/2007 | Desai et al. |
| 2007/0207196 A1 | 9/2007 | Zhang |
| 2008/0045559 A1 | 2/2008 | Zhang et al. |
| 2008/0063699 A1 | 3/2008 | Teifel et al. |
| 2008/0085902 A1 | 4/2008 | Bold et al. |
| 2008/0146598 A1 | 6/2008 | Bianco |
| 2008/0280987 A1 | 11/2008 | Desai et al. |
| 2009/0018078 A1 | 1/2009 | Labhasetwar |
| 2009/0047337 A1 | 2/2009 | Mescheder et al. |
| 2009/0263483 A1 | 10/2009 | Desai et al. |
| 2009/0304805 A1 | 12/2009 | Desai et al. |
| 2010/0048499 A1 | 2/2010 | Desai et al. |
| 2010/0166869 A1 | 7/2010 | Desai et al. |
| 2010/0183728 A1 | 7/2010 | Desai et al. |
| 2010/0215751 A1 | 8/2010 | Desai et al. |
| 2010/0297243 A1 | 11/2010 | Desai et al. |
| 2011/0052708 A1 | 3/2011 | Soon-Shiong et al. |
| 2011/0118298 A1 | 5/2011 | Fritz et al. |
| 2011/0118342 A1 | 5/2011 | De et al. |
| 2011/0151012 A1 | 6/2011 | Desai et al. |
| 2011/0165256 A1 | 7/2011 | Desai et al. |
| 2012/0004177 A1 | 1/2012 | Desai et al. |
| 2012/0070502 A1 | 3/2012 | Desai et al. |
| 2012/0076862 A1 | 3/2012 | Desai et al. |
| 2012/0128732 A1 | 5/2012 | Trieu et al. |
| 2012/0189701 A1 | 7/2012 | Desai et al. |
| 2012/0231082 A1 | 9/2012 | Desai et al. |
| 2012/0283205 A1 | 11/2012 | Desai et al. |
| 2012/0308612 A1 | 12/2012 | De et al. |
| 2013/0045240 A1 | 2/2013 | Tao et al. |
| 2013/0071438 A1 | 3/2013 | Desai et al. |
| 2013/0115296 A1 | 5/2013 | Yeo et al. |
| 2013/0195922 A1 | 8/2013 | Desai et al. |
| 2013/0195983 A1 | 8/2013 | Desai et al. |
| 2013/0195984 A1 | 8/2013 | Desai et al. |
| 2013/0202709 A1 | 8/2013 | Desai et al. |
| 2013/0209518 A1 | 8/2013 | Desai et al. |
| 2013/0244952 A1 | 9/2013 | Desai et al. |
| 2013/0266659 A1 | 10/2013 | Desai et al. |
| 2013/0280336 A1 | 10/2013 | Desai et al. |
| 2013/0280337 A1 | 10/2013 | Desai et al. |
| 2014/0017315 A1 | 1/2014 | Desai et al. |
| 2014/0017323 A1 | 1/2014 | Desai et al. |
| 2014/0023717 A1 | 1/2014 | Desai et al. |
| 2014/0039069 A1 | 2/2014 | Desai et al. |
| 2014/0039070 A1 | 2/2014 | Desai et al. |
| 2014/0056986 A1 | 2/2014 | Desai et al. |
| 2014/0072630 A1 | 3/2014 | Tao et al. |
| 2014/0072631 A1 | 3/2014 | Trieu et al. |

(56) References Cited

U.S. PATENT DOCUMENTS

| | | | |
|---|---|---|---|
| 2014/0072643 A1 | 3/2014 | Desai et al. |
| 2014/0079787 A1 | 3/2014 | Yeo et al. |
| 2014/0079788 A1 | 3/2014 | Desai et al. |
| 2014/0079793 A1 | 3/2014 | Desai et al. |
| 2014/0080901 A1 | 3/2014 | Desai et al. |
| 2014/0134257 A1 | 5/2014 | Desai et al. |
| 2014/0155344 A1 | 6/2014 | Desai et al. |
| 2014/0170228 A1 | 6/2014 | Desai et al. |
| 2014/0186447 A1 | 7/2014 | Desai |
| 2014/0199403 A1 | 7/2014 | Desai et al. |
| 2014/0199404 A1 | 7/2014 | Heise et al. |
| 2014/0199405 A1 | 7/2014 | Pierce et al. |
| 2014/0271871 A1 | 9/2014 | Desai et al. |
| 2014/0296279 A1 | 10/2014 | Seward et al. |
| 2014/0296353 A1 | 10/2014 | Desai et al. |
| 2014/0302157 A1 | 10/2014 | Desai et al. |
| 2015/0050356 A1 | 2/2015 | Desai et al. |
| 2015/0079177 A1 | 3/2015 | Desai et al. |
| 2015/0079181 A1 | 3/2015 | Desai et al. |
| 2015/0104521 A1 | 4/2015 | Desai et al. |
| 2015/0111960 A1 | 4/2015 | Desai et al. |
| 2015/0157722 A1 | 6/2015 | Foss et al. |
| 2015/0165047 A1 | 6/2015 | Desai et al. |
| 2015/0190519 A1 | 7/2015 | Desai et al. |
| 2015/0313866 A1 | 11/2015 | Desai et al. |
| 2016/0008330 A1 | 1/2016 | Desai et al. |
| 2016/0015681 A1 | 1/2016 | Desai et al. |
| 2016/0015817 A1 | 1/2016 | Benettaib et al. |
| 2016/0151325 A1 | 6/2016 | Desai et al. |
| 2016/0228401 A1 | 8/2016 | Desai et al. |
| 2016/0374952 A1 | 12/2016 | Yeo et al. |
| 2017/0007569 A1 | 1/2017 | De et al. |
| 2017/0014373 A1 | 1/2017 | Desai et al. |
| 2017/0020824 A1 | 1/2017 | Desai et al. |

FOREIGN PATENT DOCUMENTS

| | | |
|---|---|---|
| RU | 2007147382 A | 6/2009 |
| WO | WO-91/15193 A1 | 10/1991 |
| WO | WO-9418954 A1 | 9/1994 |
| WO | WO-95/03036 A1 | 2/1995 |
| WO | WO-98/07410 A1 | 2/1998 |
| WO | WO-98/14174 A1 | 4/1998 |
| WO | WO-98/14174 C1 | 4/1998 |
| WO | WO-98/14175 A1 | 4/1998 |
| WO | WO-99/00113 A1 | 1/1999 |
| WO | WO-00/06152 A1 | 2/2000 |
| WO | WO-00/64437 A1 | 11/2000 |
| WO | WO-00/71079 A2 | 11/2000 |
| WO | WO-00/71163 A1 | 11/2000 |
| WO | WO-01/34174 A2 | 5/2001 |
| WO | WO-01/34174 A3 | 5/2001 |
| WO | WO-01/76567 A1 | 10/2001 |
| WO | WO-0189522 A1 | 11/2001 |
| WO | WO-02/24179 A2 | 3/2002 |
| WO | WO-02/056912 A2 | 7/2002 |
| WO | WO-02/076459 A1 | 10/2002 |
| WO | WO-02087545 A1 | 11/2002 |
| WO | WO-03/008665 A1 | 1/2003 |
| WO | WO-03096944 A1 | 11/2003 |
| WO | WO-2004/017964 A1 | 3/2004 |
| WO | WO-2004/052401 A2 | 6/2004 |
| WO | WO-2005/000266 A2 | 1/2005 |
| WO | WO-2005/000900 A1 | 1/2005 |
| WO | WO-2005/027842 A2 | 3/2005 |
| WO | WO-2005/027842 A3 | 3/2005 |
| WO | WO-2005/039533 A1 | 5/2005 |
| WO | WO-2005/117952 A2 | 12/2005 |
| WO | WO-2005/117978 A2 | 12/2005 |
| WO | WO-2005/117986 A2 | 12/2005 |
| WO | WO-2006/090928 A1 | 8/2006 |
| WO | WO-2006089290 A1 | 8/2006 |
| WO | WO-2006/117220 A2 | 11/2006 |
| WO | WO-2006/117220 A3 | 11/2006 |
| WO | WO-2006/124684 A2 | 11/2006 |
| WO | WO-2006/124684 A3 | 11/2006 |
| WO | WO-2006/125101 A2 | 11/2006 |
| WO | WO-2006/125101 A3 | 11/2006 |
| WO | WO-2007/027819 A2 | 3/2007 |
| WO | WO-2007-027819 A3 | 3/2007 |
| WO | WO-2007/027941 A2 | 3/2007 |
| WO | WO-2007/027941 A3 | 3/2007 |
| WO | WO-2007/059116 A2 | 5/2007 |
| WO | WO-2007/107305 A2 | 9/2007 |
| WO | WO-2007/107305 A3 | 9/2007 |
| WO | WO-2008/021186 A2 | 2/2008 |
| WO | WO-2008/021186 A3 | 2/2008 |
| WO | WO-2008/027055 A1 | 3/2008 |
| WO | WO-2008/057562 A1 | 5/2008 |
| WO | WO-2008/076373 A1 | 5/2008 |
| WO | WO-2008/109163 A1 | 9/2008 |
| WO | WO-2008/137148 A2 | 11/2008 |
| WO | WO-2008/137148 A3 | 11/2008 |
| WO | WO-2008/150532 A1 | 12/2008 |
| WO | WO-2009/126175 A1 | 10/2009 |
| WO | WO-2009/126401 A2 | 10/2009 |
| WO | WO-2009/126938 A2 | 10/2009 |
| WO | WO-2010/068925 A1 | 6/2010 |
| WO | WO-2010/105172 A1 | 9/2010 |
| WO | WO-2010/118365 A1 | 10/2010 |
| WO | WO-2010/121000 A1 | 10/2010 |
| WO | WO-2011/025838 A1 | 3/2011 |
| WO | WO-2011/119988 A1 | 9/2011 |
| WO | WO-2011/123393 A1 | 10/2011 |
| WO | WO-2011/123395 A1 | 10/2011 |
| WO | WO-2011/153009 A1 | 12/2011 |
| WO | WO-2011/153485 A2 | 12/2011 |
| WO | WO-2011-153485 A3 | 12/2011 |
| WO | WO-2011/156119 A1 | 12/2011 |
| WO | WO-2012/149451 A1 | 11/2012 |

OTHER PUBLICATIONS

Abou-Alfa, G. K. et al. (Sep. 20, 2006). "Randomized Phase III Study of Exatecan and Gemcitabine Compared with Gemcitabine Alone in Untreated Advanced Pancreatic Cancer," *J. Clin. Oncol.* 24(27):4441-4447.

Abraxis Bioscience, Inc. (Mar. 17, 2010). "Abraxane Meets Primary Endpoint in Phase 3 Trial for Advanced Non-Small Cell Lung Cancer," Press Release located at <http://www.biospace.com/news_print.aspx?NewsEntityId=174173>, last visited May 3, 2010, 3 pages total.

ADIS Data Information BV. (Aug. 28, 2004). "Paclitaxel [Taxol] and Liposomal Doxorubicin [Caelyx] Cotherapy Appears to be an Effective First-line Treatment in Patients with Metastatic Breast Cancer," *Inpharma* 1452:8.

Albain, K. S. et al. (Sep. 1991). "Survival Determinants in Extensive-Stage Non-Small-Cell Lung Cancer: The Southwest Oncology Group Experience," *J. Clin. Oncol.* 9(9):1618-1626.

Alberola, V. et al. (Sep. 1, 2003). "Cisplatin Plus Gemcitabine versus a Cisplatin-Based Triplet Versus Nonplatinum Sequential Doublets in Advanced Non-Small-Cell Lung Cancer: A Spanish Lung Cancer Group Phase III Randomized Trial," *J. Clin. Oncol.* 21(17)3207-3213.

Alberts, S. R. et al. (Oct. 2005). "PS-341 and Gemcitabine in Patients with Metastatic Pancreatic Adenocarcinoma: a North Central Cancer Treatment Group (NCCTG) Randomized Phase II Study," *Annals of Oncology* 16(10):1654-1661.

Allerton, J.P. et al. (Jun. 20, 2006). "A Phase II Evaluation of the Combination of Paclitaxel Protein-bound and Carboplatin in the First-line Treatment of Advanced Non-small Cell Lung Cancer (NSCLC)," Abstract, 2006 ASCO Annual Meeting Proceedings, Part 1, *J. Clin. Oncol.* 24(18 Suppl.): Abstract No. 7127, located at http://www.asco.org/portal/site/ASCO/template.RAW/menu-item . . . >, last visited on Oct. 1, 2008, two pages.

Almhanna, K. et al. (Sep. 2008). "Second-Line Therapy for Gemcitabine-Refractory Pancreatic Cancer: Is There a Standard?" *Oncology*, 22(10):1176-1196.

Altmayer, P. et al. (Oct. 1995). "Propofol Binding to Human Blood Proteins," *Arzneimittelforschung* 45(II):1053-1056.

(56) References Cited

OTHER PUBLICATIONS

American Cancer Society, (2009). "Cancer Facts and Figures," located at http://www.cancer.org/downloads/STT/500809web.pdf, pp. 1-19.

American Cancer Society, (2009). "Cancer Facts and Figures," located at http://www.cancer.org/downloads/STT/500809web.pdf, pp. 1-72.

American Cancer Society (2009). "Surveillance and Health Policy Research," located at http://www.cancer.org/downloads/STT/500809web.pdf, pp. 1-19.

Ardavanis, A. et al. (2009). "Biweekly Gemcitabine (GEM) in Combination With Eriotinib (ERL): An Active and Convenient Regimen for Advanced Pancreatic Cancer," *Anticancer Research* 29:5211-5218.

Ashkenas, J. (Mar./Apr. 2003). "The Metronome Ticks On," *Preclinica*, located at <http://www.preclinica.com/default.asp?page=articles&issue=0303>, last visited on Apr. 29, 2007, pp. 1-2.

Belani, C.P. et al. (Aug. 1, 2003). "Multicenter, Randomized Trial for Stage IIIB or IV Non-Small-Cell Lung Cancer Using Weekly Paclitaxel and Carboplatin Followed by Maintenance Weekly Paclitaxel or Observation," *J. Clin. Oncol* .21(15):2933-2939.

Belani, C. P. et al. (Jan. 20, 2008). "Randomized, Phase III Study of Weekly Paclitaxel in Combination With Carboplatin Versus Standard Every-3-Weeks Administration of Carboplatin and Paclitaxel for Patients With Previously Untreated Advanced Non-Small-Cell Lung Cancer," *J. Clin. Oncol.* 26(3):468-473.

Berlin, J. D. et al. (Aug. 1, 2002). "Phase III Study of Gemcitabine in Combination With Fluorouracil Versus Gemcitabine Alone in Patients With Advanced Pancreatic Carcinoma: Eastern Cooperative Oncology Group Trial E2297," *J. Clin. Oncol.* 20(15):3270-3275.

Bertolini, F. et al. (Aug. 1, 2003). "Maximum Tolerable Dose and Low-Dose Metronomic Chemotherapy Have Opposite Effects on the Mobilization and Viability of Circulating Endothelial Progenitor Cells," *Cancer Res.* 63(15):4342-4346.

Bocci, G. et al. (Dec. 1, 2002). "Protracted Low-Dose Effects on Human Endothelial Cell Proliferation and Survival in Vitro reveal a Selective Antiangiogenic Window for Various Chemotherapeutic Drugs," *Cancer Res.* 62:6938-6943.

Bocci, G. et al. (Oct. 15, 2003). "Thrombospondin 1, a Mediator of the Antianggiogenic Effects of Low-dose Metronomic Chemotherapy," *Proc. Nat. Acad. Sci. USA* 100(22):12917-12922.

Bonomi, P. D. et al. (Nov. 1989). "Combination Chemotherapy Versus Single Agents Followed by Combination Chemotherapy in Stage IV Non-Small-Cell Lung Cancer: A Study of the Eastern Cooperative Oncology Group," *J. Clin Oncol.* 7(11):1602-1613.

Bourgeois, H et al. (Jun. 2006). "Phase I-II Study of Pegylated Liposomal Doxorubicin Combined With Weekly Paclitaxel as First-Line Treatment in Patients with Metastatic Breast Cancer," *American Journal of Clinical Oncology* 29(3):267-275.

Bramhall, S. R. et al. (Jul. 15, 2002). "A Double-Blind Placebo-Controlled, Randomised Study Comparing Gemcitabine and Marimastat With Gemcitabine and Placebo as First Line Therapy in Patients With Advanced Pancreatic Cancer," *British J. Cancer* (2002) 87(2):161-167.

Bristol-Myers Squibb Company (Rev Jul. 2007). "TAXOL® (Paclitaxel) Injection, (Patient Information Included)," located at http://packageinserts.bms.com/pi/pi_taxol.pdf, last visited May 6, 2010, 55 pages.

Bunn, P. A. Jr. (Aug. 1989). "The Expanding Role of Cisplatin in the Treatment of Non-Small-Cell Lung Cancer," *Semin. Oncol.* 16(4)(Suppl. 6):10-21.

Carmeliet, P. et al. (Sep. 14, 2000). "Angiogenesis in Cancer and Other Diseases," *Nature* 407(6801):249-257.

Carter, D.C. et al. (1994). "Structure of Serum Albumin," *Adv. Protein Chem.* 45:153-203.

Cascinu, S. et al. (Feb. 2003). "Weekly Gemcitabine and Cisplatin Chemotherapy: A Well-Tolerated but Ineffective Chemotherapeutic Regimen Ii Advanced Pancreatic Cancer Patients. A report from the Italian Group for the Study of Digestive Tract Cancer (GISCAD)," *Annals of Oncology* 14(2):205-208.

Cerny, T. et al. (1994). "Docetaxel (Taxotere™) is Active in Non-Small-Cell Lung Cancer: A Phase II Trial of the Eortc Early Clinical Trials Group (ECTG)," *Br. J. Cancer* 70:384-387.

Chustecka, Z. et al. (Sep. 16, 2008). "New Drug Shows Promise in Pancreatic Cancer in Phase 2 Trial," *Medscape Medical News*, located at htpp://www.medscape.com/viewarticle/580571, last visited Nov. 19, 2009, 2 pages.

Clinical Trials (Jan. 12, 2010). "Phase II Trial of Abraxane in the Treatment of Patients With Pancreatic Cancer Who Have Failed First-Line Treatment With Gemcitabine-Based Therapy," article located at <http://clinicaltrials.gov/archive/NCT00691054/2010_01_12>, last visited on Feb. 13, 2013, 3 pages.

Colomer, R. (Dec. 2004). "Gemcitabine and Paclitaxel in Metastatic Breast Cancer: A Review," *Oncology* 18(14): Supplement, pp. 8-12.

Colucci, G. et al. (Feb. 15, 2002). "Gemcitabine Alone or with Cisplatin for the Treatment of Patients with Locally Advanced and/or Metastatic Pancreatic Carcinoma: A Prospective, Randomized Phase III Study of the Gruppo Oncologia dell'Italia Meridionale," *Cancer* 94(4)902-910.

Conrad, C. et al. (Jul. 2007). "Antiangiogentic and Antitumor Activity of a Novel Vascular Endothelial Growth Factor Receptor-2 Tyrosine Kinase Inhibitor ZD6474 in a Metastatic Human Pancreatic Tumor Model," *Anticancer Drugs* 18(5):569-579.

Crinò, L. et al. (Nov. 1999). "Gemcitabine and Cisplatin versus Mitomycin, Ifosfamide, and Cisplatin in Advanced Non-Small-Cell Lung Cancer: A Randomized Phase III Study of the Italian Lung Cancer Project," *J. Clin. Oncol.* 17(11):3522-3530.

Curry, S. et al. (Sep. 1998). "Crystal Structure of Human Serum Albumin Complexed with Fatty Acid Reveals an Asymmetric Distribution of Binding Sites," *Nat. Struct. Biol.* 5(9):827-835.

Custodio, A. et al. (2009). "Second-Line Therapy for Advanced Pancreatic Cancer: A Review of the Literature and Future Directions," *Cancer Treatment Review* 35:676-684.

Damascelli, B. et al. (Nov. 15, 2001). "Intraarterial Chemotherapy with Polyoxyethylated Castor Oil Free Pacitaxil, Incorporated in Albumin Nanoparticles (ABI-007)," *Cancer* 92(10):2592-2602.

Damascelli, B. et al. (Jul. 2003). "A Novel Intraarterial Chemotherapy Using Paclitaxel in Albumin Nanoparticles to Treat Advanced Squamous Cell Carcinoma of the Tongue: Preliminary Findings," *AJR* 181:253-260.

Dennis, A. et al. (2007). "hERG Channel Trafficking: Novel Targets in Drug-Induced Long QT Syndrome," *Biochem. Soc. Trans.* 35(5):1060-1063.

Depierre, A. et al. (Mar. 1988). "Phase II Study of Navelbine (NVB) in Non Small Cell Lung Cancer (NSCLC)," *Proc. Am. Soc. Clin. Oncol*, 24th Annual Meeting of the American Society of Clinical Oncology (ASCO), May 22-24, 1988, Proceedings, New Orleans, Louisiana, vol. 7, p. 201, Abstract No. 778.

Desai, N. et al. (Jul. 2003). "Oral Bioavailability of Paclitaxel in a Novel, Cremophor EL-free, Protein-based Nanoparticle Preparation," *Proceedings of the Amer. Assn. for Cancer Research* 44(2):732, Abstract No. 3673.

Desai, N. et al. (Feb. 15, 2006). "Increased Antitumor Activity, Intratumor Paclitaxel Concentrations, and Endothelial Cell Transport of Cremophor-Free, Albumin-Bound Paclitaxel, ABI-007, Compared with Cremophor-Based Paclitaxel,"*Clin. Cancer Res.* 12(4):1317-1324.

De Vos A. et al. (Nov. 1997). "Differential Modulation of Cisplatin Accumulation in Leukocytes and Tumor Cell Lines by the Paclitaxel Vehicle Cremophor EL," *Ann. Onc.* 8(11):1145-1150.

drugs.com (May 20, 2010). "Second Trial With Abraxane to Demonstrate Increased Survival in Patients With Advanced Pancreatic Cancer," article located at <http://www.drugs.com/clinical_trials/second-trial-abraxane-demonstrate-increased-survival -patients-advanced-pancreatic-cancer-9451.html>, last visited on Aug. 16, 2011, 4 pages.

Du Bois, A. et al. (1997). "Phase I/II Study of the Combination of Carboplatin and Paclitaxel as First-line Chemotherapy in Patients with Advanced Epithelial Ovarian Cancer," *Ann. Oncol.* 8:355-361.

(56) References Cited

OTHER PUBLICATIONS

Edge, S. B. (eds) et al. (2010). Lung: Carcinoid Tumors are Included. Sarcomas and Other Rare Tumors are not included), Chapter 25 in *AJCC Cancer Staging Manual*, Seventh Edition, American Joint Committee on Cancer, Springer, Chicago, IL, pp. 253-270.
El-Khoueiry, A. B. et al. (May 20, 2010 Supplement). "A Phase I Study of Two Different Schedules of Nab-Paclitaxel (Nab-p) With Ascending Doses of Vandetanib (V) in Patients (pts) With Advanced Solid Tumors," *J. Clin. Oncol.* 28(15s): Abstract 3059, 2 pages.
Ellerby, H.M. et al. (Sep. 1999). "Anti-Cancer Activity of Targeted Pro-Apoptotic Peptides," *Nat. Med.* 5(9):1032-1038.
European Search Report dated Jun. 29, 2011, for European Patent Application No. 100111061, filed on Feb. 21, 2006, 9 pages.
Extended European Search Report dated Jul. 3, 2012, for European Patent Application No. 12154995.0, filed on Nov. 6, 2007, 6 pages.
Extended European Search Report dated Sep. 20, 2013, for European Patent Application No. 11790193.4, filed on Dec. 19, 2012, 6 pages.
Fehske, K.J. et al. (1981). "The Location of Drug Binding Sites in Human Serum Albumin," *Biochem. Pharmcol.* 30(7):687-692.
Ficker, E. et al. (Jun. 27, 2003, e-pub. May 29, 2003). "Role of the Cytosolic Chaperones Hsp70 and Hsp90 in Maturation of the Cardiac Potassium Channel hERG," *Circ. Res.* 92:e87-e100.
Ficker, E. et al. (2005). "The hERG Cardiac Potassium Channel: Structure, Function and Long QT Syndrome," *Novartis Found. Symp.* 266:57-69.
Finlayson, J.S. (1980). "Albumin Products," *Seminars in Thrombosis and Hemostasis* 6(2):85-120.
Fleming, G.F. et al. (Jun. 1, 2004). "Phase III Trial of Doxorubicin Plus Cisplatin with or without Paclitaxel plus Filgrastim in Advanced Endometrial Carcinoma: a Gynecologic Oncology Group Study," *J. Clin. Oncol.* 22(11):2159-2166.
Foote, M. et al. (2007). "Using Nanotechnology to Improve the Characteristics of Antineoplastic Drugs: Improved Characteristics of nab-Paclitaxel Compared With Solvent-Based Paclitaxel," *Biotechnology Annual Review* 13:345-357.
Fossella, F. V. et al. (Mar. 1995). "Phase II Study of Docetaxel for Advanced or Metastatic Platinum-Refractory Non-Small-Cell Lung Cancer," *J. Clin. Oncol.* 13(3):645-651.
Fossella, F. et al. (Aug. 15, 2003). "Randomized, Multinational, Phase III Study of Docetaxel Plus Platinum Combinations Versus Vinorelbine Plus Cisplatin for Advanced Non-Small-Cell Lung Cancer: the TAX 326 Study Group," *J. Clin. Oncol.* 21(16):3016-3024.
Fujimoto-Ouchi, K. et al. (Apr. 2001). "Schedule of Dependency of Antitumor Activity in Combination Therapy with Capecitabine/5'Deoxy-5-fluorouridine and Docetaxel in Breast Cancer Models," *Clin. Cancer Res.* 7:1079-1086.
Fulfaro F. et al. (Jul. 15, 2004). "Weekly Paclitaxel (T) and Pegylated Liposomal Doxorubicin (PLD) as First Line Treatment in Metastatic Breast Cancer (MBC) Patients," *J. Clin. Oncol.* 22(145):53S, Abstract No. 704.
Garrido, M.J. et al. (1994). "Binding Characteristics of Propofol to Plasma Proteins and Possible Interactions," *Rev. Esp. Anestesiol. Reanim.* 41(6):308-312.
Gatzemeier, U. et al. (1995). "Phase II Study with Paclitaxel for the Treatment of Advanced Inoperable Non Small Cell Lung Cancer," *Lung Cancer* 12(Suppl 2):S101-S106.
Gatzemeier, U. et al. (Oct. 1, 2000). "Phase III Comparative Study of High-Dose Cisplatin Versus a Combination of Paclitaxel and Cisplatin in Patients with Advanced Non-Small-Cell Lung Cancer," *J. Clin. Oncol.* 18(19):3390-3399.
Gelderblom, H. et al. (2001). "Cremophor EL: The Drawbacks and Advantages of Vehicle Selection for Drug Formulation," *Eur. J. Cancer* 37:1590-1598.
Gelderblom, H. et al. (Apr. 2002). "Influence of Cremophor EL on the Bioavailability of Interperitoneal Paclitaxel," *Clin. Cancer Res.* 8:1237-1241.

Gemzar® (Gemcitabine hci) for Injection Product Label, (revised May 7, 2007). Description, Eli Lilly and Company, IN 46285, 10 pages.
Goodman et al. (1996). *The Pharmacological Basis of Therapeutics*, 9th ed, McGraw-Hill New York, pp. v-xii (Table of Contents Only.)
Gradishar, W.J. et al. (Nov. 1, 2005). "Phase III Trial of Nanoparticle Albumin-Bound Paclitaxel Compared with Polyethylated Castor Oil-Based Paclitaxel in Women With Breast Cancer," *J. Clin. Oncol.* 23(31):7794-7803.
Green, M. R. et al. (Aug. 2006, e-pub. Jun. 1, 2006). "Abraxane® A Novel Cremophor-Free, Albumin-Bound Particle Form of Paclitaxel for the Treatment of Advanced Non-Small-Cell Lung Cancer," *Ann. Oncol.* 17(8):1263-1268.
Grilli, R. et al. (Oct. 1993). "Chemotherapy for Advanced Non-Small-Cell Lung Cancer: How Much Benefit is Enough?" *J. Clin. Oncol.* 11(10):1866-1872.
Hainsworth, J. D. et al. (Jul. 1995). "Paclitaxel by 1-Hour Infusion: An Active Drug in Metastatic Non-Small-Cell Lung Cancer," *J. Clin. Oncol.* 13(7):1609-1614.
Harries, M. et al. (Nov. 1, 2005). "Nanoparticle Albumin-Bound Paclitaxel for Metastatic Breast Cancer," *J. Clin. Oncol.* 23(31):7768-7771.
Hauser, C.J. et al. (Jun. 1980). "Oxygen Transport Responses to Colloids and Crystalloids in Critically Ill Surgical Patients," *Surgery Gynecology & Obstetrics* 150(6):811-816.
Hawkins, M.J. et al. (Jun. 20, 2006). "Dose Escalation Study of Nab-Paclitaxel Followed by Carboplatin as First Line Therapy in Advanced Non-small Cell Lung Cancer (NSCLC)," Abstract, 2006 ASCO Annual Meeting Proceedings, Part 1, *J. Clin. Oncol.* 24(18 Suppl.): Abstract No. 7132, located at http://www.asco.org/portal/site/ASCO/template.RAW/menuitem . . . >, last visited on Oct. 1, 2008, two pages.
Hawkins, M.J. et al. (Jun. 20, 2007). "Study of Three Weekly Nab-Paclitaxel Regimens in Combination with Carboplatin as First-line Therapy in Advanced Non-small Cell Lung Cancer (NSCLC)," Abstract, 2007 ASCO Annual Meeting Proceedings, Part 1, *J. Clin. Oncol.* 25(18 Suppl.): Abstract No. 7659, located at http://www.asco.org/portal/site/ASCO/template.RAW/menuitem . . . >, last visited on Oct. 1, 2008, two pages.
Hawkins, M.J. et al. (Sep. 2007). "High-dose 130-nanometer Albumin-bound Paclitaxel in Combination with Carboplatin as First-line Therapy in Advanced Non-small Cell Lung Cancer," Poster No. 6563, *Eur. J. Cancer Supplements* 5(4):376-377.
Haymarket Group (Jan. 2005). "Neoplastic Disorders," in Section 18 of MIMS, pp. 333-343.
He, X.M. et al. (Jul. 16, 1992). "Atomic Structure and Chemistry of Human Serum Albumin," *Nature* 358:209-215.
Heinemann, V. et al. (Aug. 20, 2006). "Randomized Phase III Trial of Gemcitabine plus Cisplatin Compared with Gemcitabine Alone in Advanced Pancreatic Cancer," *J. Clin. Oncol.* 24(24):3946-3952.
Herbst, R. S. et al. (Mar. 1, 2004). "Gefitinib in Combination with Paclitaxel and Carboplatin in Advanced Non-Small-Cell Lung Cancer: A Phase III Trial—INTACT 2," *J. Clin. Oncol.* 22(5):785-794.
Herrmann, R. et al. (Jun. 1, 2007). "Gemcitabine Plus Capecitabine Compared with Gemcitabine Alone in Advanced Pancreatic Cancer: A Randomized, Multicenter, Phase III Trial of the Swiss Group for Clinical Cancer Research and the Central European Cooperative Oncology Group," *J. Clin. Oncol.* 25(16):2212-2217.
Hosein, P. J. et al. (2001). "A Phase II Trial of Nab-Paclitaxel (NP) in Patients With Advanced Pancreatic Cancer (PC) Who Have Progressed on Gemcitabine (G)-Based Therapy," *J. Clin. Oncol.* 28(15s): Abstract 4120, 3 pages.
Hudis, C. et al. (Jan. 1999). "Sequential Dose-dense Doxorubicin, Paclitaxel, and Cyclophosphamide for Resectable High-risk Breast Cancer: Feasibility and Efficacy," *J. Clin. Oncol.* 17(1):93-100.
Hudis, C. (Aug. 20, 2005). "Testing Chemotherapy for Breast Cancer: Timing is Everything," *J. Clin. Oncol.* 23(24):5434-5436.
Ibrahim, N. K. et al. (May 2002). "Phase I and Pharmacokinetic Study of ABI-007, a Cremophor-Free, Protein-Stabilized, Nanoparticle Formulation of Paclitaxel," *Clinical Cancer Research* 8:1038-1044.

(56) References Cited

OTHER PUBLICATIONS

Ibrahim, N.K. et al. (Sep. 1, 2005). "Multicenter Phase II Trial of ABI-007, an Albumin-Bound Paclitaxel, in Women With Metastatic Breast Cancer," *J. Clin. Oncol.* 23(25):6019-6026.

International Search Report dated Jul. 11, 2011, for PCT Patent Application No. PCT/US2011/037462, filed on May 20, 2011, 4 pages.

International Search Report dated Jul. 7, 2006, for PCT Application No. PCT/US2006/006167, filed on Feb. 21, 2006, 4 pages.

International Search Report dated Mar. 17, 2008, for PCT Application No. PCT/US2007/023446, filed on Nov. 6, 2007, 3 pages.

Jafar, N. et al. (Apr. 19, 2010). "Caveolin-1 Inhibits Survivin and Increases Sensitivity to Paclitaxel in Breast Cancer Cells," AACR 101st Annual Meeting 2010, Meeting held on Monday, Apr. 19, 2010, in Washington D.C., Poster Section 23, Poster Board No. 4, Abstract 2547, one page.

Jimenez, J.J. et al. (Jan. 15, 1992). "Protection from 1-β-D-Arabinofuranosylcytosine-Induced Alopecia by Epidermal Growth Factor and Fibroblast Growth Factor in the Rat Model," *Cancer Research* 52(2):413-415.

Johnson, D.H. et al. (1996). "Paclitaxel Plus Carboplatin in Advanced Non-small-cell Lung Cancer: A Phase II Trial," *J. Clin. Oncol.* 14:2054-2060.

Jones, C. M. et al. (Oct. 18, 2007). "Targeted Therapies for NSCLC," US Pharmacist, article located at <http://www.uspharmacist.com/content/t/oncologv/c/10219/> last visited May 6, 2010, 9 pages.

Jones, V. et al. (2000). "Phase II Study of Weekly Paclitaxel (Taxol) and Liposomal Doxorubicin (Doxil) in Patients with Locally Advanced and Metastatic Breast Cancer," *Proc. Amer. Soc. Clin. Oncol.* 19:116a, Abstract No. 451.

Kelly, K. et al. (Jul. 1, 2001). "Randomized Phase III Trial of Paclitaxel Plus Carboplatin Versus Vinorelbine Plus Cisplatin in the Treatment of Patients with Advanced Non-Small-Cell Lung Cancer: A Southwest Oncology Group Trial," *J. Clin. Oncol.* 19(13):3210-3218.

Kim, S.-O. et al. (2005). "Superior Antitumor Efficacy of Genexol®-PM, a Biodegradable Polymeric Micelle-Based Formulation of Paclitaxel (Genexol®) Compared with Gemzar® (Gemcitabine) and Taxol® in Human Pancreatic Cancer Cells in Vitro and in Vivo," Experimental and Molecular Therapeutics 10: Drug Targeting, *Proc. Amer. Assoc. Cancer Res.*, vol. 46, Abstract No. 1440, 2 pages, located at <http://www.aacrmeetingabstracts.org/cgi/content/abstract/2005/1/337-b>, last visited Feb. 22, 2010.

Kim, Y.-N. et al. (2002). "Caveolin-1 Phosphorylation in Human Squamous and Epidermoid Carcinoma Cells: Dependence on ErbB1 Expression and Src Activation," *Exp.Cell Res.* 280:134-147.

Klement, G. et al. (Jan. 2002). "Differences in Therapeutic Indexes of Combination Metronomic Chemotherapy and an Anti-VEGFR-2 Antibody in Multidrug-Resistant Human Breast Cancer Xenografts," *Clin. Cancer. Res.* 8(1)221-232.

Ko, A. et al. (2005). "Serum CA19-9 Response as a Surrogate for Clinical Outcome in Patients Receiving Fixed-Dose Rate Gemcitabine for Advanced Pancreatic Cancer," *British Journal of Cancer* 93:195-199.

Kolodgie, F. D. et al. (Sep. 3, 2002). "Sustained Reduction of in-Stent Neointimal Growth with the Use of a Novel Systemic Nanoparticle Paclitaxel," *Circulation* 106(10):1195-1198.

Kondrateva, A. P. (2001). The Combination of Radiation and Drug Therapies for the Organ Safe Treating of Malignant Tumours, *Modern Oncology* 3(3), located at <http://www.consiliummedicum.com/magazines/cm/pediatrics/article/8403>, in Russian, with English translation (author translated as A. P. Kondratieff) (from translategoogle.com), 6 pages total.

Kosmidis, P. et al. (Sep. 1, 2002). "Paclitaxel Plus Carboplatin Versus Gemcitabine Plus Paclitaxel in Advanced Non-small-cell Lung Cancer: A Phase III Randomized Trial," *J. Clin. Oncol.* 20(17):3578-3585.

Kragh-Hansen, U. (Feb. 1990). "Structure and Ligand Binding Properties of Human Serum Albumin," *Dan. Med. Bull.* 37(1):57-84.

Langer, C.J. et al. (Aug. 1995). "Paclitaxel by 24- or 1-Hour Infusion in Combination with Carboplatin in Advanced Non-Small Cell Lung Cancer: The Fox Chase Cancer Center Experience," *Semin. Oncol.* 22(4-Suppl. 9):18-29.

Langer, C.J. et al. (Dec. 1996). "Combination Paclitaxel (1-Hour) and Carboplatin (AUC 7.5) in Advanced Non-Small Cell Lung Cancer: A Phase II Study by the Fox Chase Cancer Center Network," *Semin. Oncol.* 23(6-Suppl. 16):35-41.

Langer, C. J. et al. (Jun. 2008). "Phase III Trial Comparing Paclitaxel Poliglumex (CT-2103, PPX) in Combination with Carboplatin Versus Standard Paclitaxel and Carboplatin in the Treatment of PS 2 Patients with Chemotherapy-Naïve Advanced Non-Small Cell Lung Cancer," *J. Thorac. Oncol.* 3(6):623-630.

Le Chevalier, T. et al. (Feb. 1994). "Randomized Study of Vinorelbine and Cisplatin Versus Vindesine and Cisplatin versus Vinorelbine Alone in Advanced Non-Small-Cell Lung Cancer: Results of a European Multicenter Trial Including 612 Patients," *J. Clin. Oncol.* 12(2):360-367.

Leong, S.-S. et al. (Feb. 1, 2005, E-pub. Dec. 20, 2004). "Paclitaxel, Carboplatin, and Gemcitabine in Metastatic Nasopharyngeal Carcinoma: A Phase II Trial Using a Triplet Combination," *Cancer* 103(3):569-575.

Levine, M. N. et al. (Published Ahead of Print on Apr. 30, 2012). "Method to Our Madness or Madness in Our Method? Pitfalls in our Methodology, " *J. Clin. Oncol.* 3 pages.

Li, C. et al. (Jun. 1, 1998). "Complete Regression of Well-Established Tumors Using a Novel Water-Soluble Poly(L-Glutamic Acid)-Paclitaxel Conjugate," *Cancer Research* 58:2404-2409.

Li, C. et al. (Jul. 2000). "Tumor Irradiation Enhances the Tumor-Specific Distribution of Poly(L- Glutamic Acid)—Conjugated Paclitaxel and Its Antitumor Efficacy," *Clin. Cancer Res.* 6(7):2829-2834.

Li, C. et al. (May 22, 2008). "Polymer-Drug Conjugates: Recent Development in Clinical Oncology," *Adv. Drug Deliv. Rev.* 60(8):886-898, 24 pages.

Li, J. et al. (Jul. 6, 2009). "Any Progress in the Management of Advanced Pancreatic Cancer?," Highlights from the 45th ASCO Annual Meeting, Orlando, FL., USA, May 29-Jun. 2, 2009, *Journal of the Pancreas* 10(4):361-365.

Lilenbaum, R. C. et al. (2002). "Single-Agent (SA) Versus Combination Chemotherapy (CC) in Advanced Non-Small Cell Lung Cancer (NSCLC): A CALGB Randomized Trial of Efficacy, Quality of Life (QOL), and Cost-Effectiveness," *Proc. Am. Soc. Clin. Oncol.* presented at 2002 Annual Meeting of the American Society of Clinical Oncology (ASCO), Jun. 2002, vol. 21, Abstract No. 2.

Link, J. S. et al. (Oct. 2007). "Bevacizumab and Albumin-Bound Paclitaxel Treatment in Metastatic Breast Cancer," *Clin. Breast Cancer* 7(10):779-783.

Loehr, M. et al. (2009). "Cationic Liposomal Paclitaxel in Combination with Gemcitabine in Patients with Advanced Pancreatic Cancer: A Phase II Trial," *Journal of Clinical Oncology* 2009 ASCO Annual Meeting Proceedings (Post-Meeting Edition), 27(15S)(May 20 Supplement) 2009:4526, 2 pages, located <http://meeting.ascopubs.org/cgi/content/abstract/27/15S/4526>, last visited on Feb. 18, 2010.

Louvet, C. et al. (Mar. 15, 2002). "Gemcitabine combined With Oxaliplatin in Advanced Pancreatic Adenocarcinoma: Final Results of a GERCOR Multicenter Phase II Study," *J. Clin. Oncol.* 20(6):1512-1518.

Louvet, C. et al. (May 20, 2005). "Gemcitabine in Combination with Oxaliplatin Compared with Gemcitabine Alone in Locally Advanced or Metastatic Pancreatic Cancer: Results of a GERCOR and GISCAD Phase III Trial," *J. Clin. Oncol.* 23(15):3509-3516.

Lowry, F. (Nov. 2008). "Drug Combo Shrinks Pancreatic Tumors in Phase I Trial," *GI & Hepatology News*, p. 14.

Lynch, T. J. et al. (2005). "Optimizing Chemotherapy and Targeted Agent Combinations in NSCLC," *Lung Cancer* 50 (Suppl. 2):S25-S32.

(56) References Cited

OTHER PUBLICATIONS

Lynch, T. J. et al. (Feb. 20, 2010). "Cetuximab and First-Line Taxane/Carboplatin Chemotherapy in Advanced Non-Small-Cell Lung Cancer: Results of the Randomized Multicenter Phase III Trial BMS099," *J. Clin. Oncol.* 28(6):911-917.

Maitra, A. et al. (Dec. 10, 2009). "Abstract C246: nab®-Paclitaxel Targets Tumor Stroma and Results, Combined with Gemcitabine, in High Efficacy Against Pancreatic Cancer Models," *Molecular Cancer Therapeutics* 8 (Meeting Abstract Supplement), C246, Abstracts: AACR-NCI-EORTC International Conference: Molecular Targets and Cancer Therapeutics, Nov. 15-19, 2009, Boston, MA, abstract located at <http://mct.aacrjournals.org/cgi/content/meeting_abstract/8/12_MeetingAbstracts/C246?sid=2cd1379d-eb9e-4215-94ed-b34b9b8c25ec>, last visited on Feb. 12, 2013, 2 pages.

Mavroudis, D. et al. (2002). "Phase I Study of Paclitaxel (Taxol) and Pegylated Liposomal Doxorubicin (Caelyx) Administered Every 2 Weeks in Patients with Advanced Solid Tumors," *Oncology* 62:216-222.

Micha, J. P. et al. (Feb. 2006, e-pub Oct. 14 2005). "Abraxane in the Treatment of Ovarian Cancer: the Absence of Hypersensitivity Reactions," *Gynecol Oncol* 100(2):437-438, 15 pages.

Miele, E. et al. (2009). "Albumin-Bound Formulation of Paclitaxel (Abraxane® ABI-007) In the Treatment of Breast Cancer," *International Journal of Nanomedicine* 4:99-105.

Milella, M. et al. (2004). "Pilot Study of celecoxib and Infusional 5-Fluorouracil as Second-Line Treatment for Advanced Pancreatic Carcinoma," *Cancer* 101(1):133-138.

Modiano, M. et al. (1999). "Phase I Study of DOXIL® (Pegylated Liposomal Doxorubicin) Plus Escalating Doses of TAXOL® in the Treatment of Patients with Advanced Breast or Gynecologic Malignancies," *Proc. Amer. Soc. Clin. Oncol.*18:220a, Abstract No. 848.

Mondesire, W. H. et al. (Oct. 15, 2004). "Targeting Mammalian Target of Rapamycin Synergistically Enhances Chemotherapy-Induced Cytotoxicity in Breast Cancer Cells," *Clin. Cancer Res.* 10(20):7031-7042.

Moore, M. J. et al. (May 20, 2007). "Erlotinib Plus Gemcitabine Compared with Gemcitabine Alone in Patients with Advanced Pancreatic Cancer: A Phase III Trial of the National Cancer Institute of Canada Clinical Trials Group," *Journal of Clinical Oncology* 25(15):1960-1966.

Moreno-Aspitia, A. et al. (2005). "Nanoparticle Albumin-bound Paclitaxel (ABI-007): a Newer Taxane Alternative in Breast Cancer," *Future Oncol.* 1(6):755-762.

Moreno-Aspitia, A. et al. (Oct. 2005). "North Central Cancer Treatment Group N0531: Phase II Trail of Weekly Albumin-bound Paclitaxel (ABI-007, Abraxane®) in Combination with Gemcitabine in Patients with Metastatic Breast Cancer," *Clinical Breast Cancer* 6(4):361-364.

Müller, B.G. et al. (1996). "Albumin Nanospheres as Carriers for Passive Drug Targeting: An Optimized Manufacturing Technique," *Pharmaceutical Research* 13(1):32-37.

Ng, S.S.W. et al. (Feb. 1, 2004). "Taxane-mediated Antiangiogenesis in Vitro: Influence of Formulation Vehicles and Binding Proteins," *Cancer Res.* 64:821-824.

Nieto, J. et al. (2008). "Metastatic Pancreatic Cancer 2008: is the Glass Less Empty?" *The Oncologist* 13:562-576.

Notice of Opposition and Grounds for Opposition filed by Generics [UK] Limited (Trading as Mylan), on Aug. 1, 2012, 23 pages.

Notice of Opposition and Grounds for Opposition filed by Medigene AG, on Aug. 2, 2012, 10 pages.

Novelos Therapeutics, Inc. (2010). "NOV-002, Cancer," located at http://www.novelos.com/html/our_products/BAM_002.htm, last visited May 6, 2010, 4 pages.

Nyman, D.W. et al. (Nov. 1, 2005). "Phase I and Pharmacokinetics Trial of ABI-007, a Novel Nanoparticle Formulation of Paclitaxel in Patients with Advanced Nonhematologic Malignancies," *J. Clin. Oncol.* 23(31):7785-7793.

O'Reilly, M.S. et al. (Oct. 21, 1994). "Angiostatin: A Novel Angiogenesis Inhibitor That Mediates the Suppression of Metastases by a Lewis Lung Carcinoma," *Cell* 79(2):315-328.

O'Reilly, M.S. et al. (Jan. 24, 1997). "Endostatin: An Endogenous Inhibitor of Angiogenesis and Tumor Growth," *Cell* 88(2):277-285.

Oettle, H. et al. (Oct. 2005). "A Phase III Trial of Pemetrexed Plus Gemcitabine Versus Gemcitabine in Patients With Unresectable or Metastatic Pancreatic Cancer," *Annals of Oncology*, 16(10):1639-1645, erratum in *Ann. Oncol.* (Mar. 2006). 17(3):525.

Okada, S. et al. (1999). "Phase II Study of Docetaxel in Patients with Metastatic Pancreatic Cancer: A Japanese Cooperative Study," *British Journal of Cancer* 80(3/4):438-443.

Onn, A. et al. (2004). "Treatment of Non-Small-Cell Lung Cancer: A Perspective on the Recent Advances and the Experience with Gefitinib," *Br. J. Cancer* 91(Suppl 2):S11-S17.

O'Shaughnessy, J.A. et al. (2004). "Weekly Nanoparticle Albumin Paclitaxel (Abraxane) Results in Long-Term Disease Control in Patients With Taxane-Refractory Metastatic Breast Cancer," *Breast Cancer Research and Treatment, 27th Annual Charles A. Coltman San Antonio Breast Cancer Symposium*, San Antonio, Texas, Dec. 8-11, 2004, 88(1):565, Abstract No. 1070.

Paal, K. et al. (2001). "High Affinity Binding of Paclitaxel to Human Serum Albumin," *Eur. J. Biochem.* 268(7), 2187-2191.

Paccagnella, A. et al. (Dec. 1996). "Paclitaxel and Carboplatin: A Phase I Study in Advanced Non-Small Cell Lung Cancer," *Semin. Oncol.* 23(6-Suppl. 16):76-79.

Papyan, a. et al. (2005). "MBT-0206 Enhances the Anti-Tumor Treatment in a Highly Metastatic Human Pancreatic Cancer Mouse Model," *Proc. Amer. Assoc. Cancer Res.* vol. 45, Cellular, Molecular, and Tumor Biology 80: Angiogenesis Inhibitors III, Abstract No. 4104, 2 pages, located at <http://aacrmeetingabstracts.org/cgi/content/abstract/2004/1/947-c>, last visited Feb. 22, 2010.

Pectasides, D. et al. (2005). "Comparison of Docetaxel and Docetaxel-Irinotecan Combination as Second-Line Chemotherapy in Advanced Non-Small-Cell Lung Cancer: A Randomized Phase II Trial," *Annals of Oncology* 16:294-299.

Perabo, F. G. et al. (Nov.-Dec. 2003). "Preclinical Evaluation of Gemcitabine/Paclitaxel-Interactions in Human Bladder Cancer Lines," *Anticancer Res.* 23(6C):4805-4814.

Pirker, R. et al. (May 2, 2009). "Cetuximab Plus Chemotherapy in Patients with Advanced Non-Small-Cell Lung Cancer (FLEX): An Open-Label Randomised Phase III Trial," *Lancet* 373:1525-1531.

Purcell, M. et al. (2000). "Interaction of Taxol With Human Serum Albumin," *Biochim. et Biophys. Acta* 1478:61-68.

Raspaglio, G. et al. (Jan. 1, 2005). "Thiocolchicine Dimers: A Novel Class of Topoisomerase-I Inhibitors," *Biochem. Pharmacol.* 69(1):113-121.

Reni, M. et al. (2008). "PEFG (Cisplatin, Epirubicin, 5-Fluorouracil, Gemcitabine), Regimen as Second-Line Therapy in Patients With Progressive or Recurrent Pancreatic Cancer After Gemcitabine-Containing Chemotherapy," *Am. J. Clin. Oncol.* 31:145-150.

Reynolds, C. et al. (Jun. 20, 2007). "An Open-label, Phase II Trial of Nanoparticle Albumin Bound Paclitaxel (Nab-paclitaxel), Carboplatin, and Bevacizumab in First-line Patients with Advanced Non-squamous Non-small Cell Llung Cancer (NSCLC)," Abstract, 2007 ASCO Annual Meeting Proceedings, Part 1, *J. Clin. Oncol.* 25(18 Suppl.): Abstract No. 7610, located at http://www.asco.org/portal/site/ASCO/template.RAW/menuitem . . . >, last visited on Oct. 1, 2008, two pages.

Reynolds, C. et al. (Dec. 2009). "Phase II Trial of Nanoparticle Albumin-Bound Paclitaxel, Carboplatin, and Bevacizumab in First-Line Patients with Advanced Nonsquamous Non-Small Cell Lung Cancer," *J. Thorac. Oncol.* 4(12):1537-1543.

Rigas, J.R. (Jun. 2, 2004). "Taxane-Platinum Combination in Advanced Non-Small Cell Lung Cancer: a Review," *Oncol.* 9(Suppl. 2):16-23.

Rizvi, N. A. et al. (Feb. 1, 2008). "Phase I/II Trial of Weekly Intravenous 130-nm Albumin-Bound Paclitaxel as Initial Chemotherapy in Patients with Stage IV Non-Small-Cell Lung Cancer," *J. Clin. Oncol.* 26(4):639-643.

(56) References Cited

OTHER PUBLICATIONS

Robert, N. et al. (Dec. 2005). "Pilot Study of Dose-dense Doxorubicin Plus Cyclophosphamide Followed by ABI-007 in Patients with Early-Stage Breast Cancer," *San Antonio Breast Cancer Symposium*, San Antonio, TX, Dec. 8-11, 2005, two pages.

Rocha-Lima, C. M. et al. (Sep. 15, 2004). "Irinotecan Plus Gemcitabine Results in No Survival Advantage Compared with Gemcitabine Monotherapy in Patients with Locally Advanced or Metastatic Pancreatic Cancer Despite Increased Tumor Response Rate," *J. Clin. Oncol.* 22(18):3776-3783.

Roche Laboratories, Inc. (Apr. 2006). "Xeloda® (Capecitabine) Tablets Product Insert," 43 pages.

Roe, S. M. et al. (Jan. 28, 1999, e-pub. Jan. 1, 1999). "Structural Basis for Inhibition of the Hsp90 Molecular Chaperone by the Antitumor Antibiotics Radicicol and Geldanamycin," *J. Med. Chem.* 42(2)260-266.

Romond, E.H. et al. (2005). "Combined Analysis of NSABP-B31/NCCTG-N9381: Disease-Free and Overall Survival Data," *Breast Cancer Update* 4(6):15-19.

Rosell, R. et al. (2002). "Phase III Randomised Trial Comparing Paclitaxel/Carboplatin with Paclitaxel/Cisplatin in Patients with Advanced Non-small-cell Lung Cancer: A Cooperative Multinational Trial," *Ann. Oncol.* 13:1539-1549.

Safran, H. et al. (2001). "Paclitaxel and Concurrent Radiation for Locally Advanced Pancreatic Cancer," *Int. J. Radiation Oncology Biol. Phys.* 49(5):1275-1279.

Safran, H. et al. (Sep. 1, 2002). "Gemcitabine, Paclitaxel, and Radiation for Locally Advanced Pancreatic Cancer: A Phase I Trial," *Int. J. Radiation Oncol. Biol. Phys.* 54(1):137-141.

Sandler, A. B. et al. (Jan. 2000). "Phase III Trial of Gemcitabine Plus Cisplatin Versus Cisplatin Alone in Patients with Locally Advanced or Metastatic Non-Small-Cell Lung Cancer," *J. Clin. Oncol.* 18(1):122-130.

Sandler, A. et al. (Dec. 14, 2006). "Paclitaxel-Carboplatin Alone or with Bevacizumab for Non-Small-Cell Lung Cancer," *New Eng. J. Med.* 355(24):2542-2550.

Sausville, E. A. et al. (Oct. 2003). "Clinical Development of 17-Allylamino, 17-Demethoxygeldanamycin," *Curr. Cancer Drug Targets* 3(5):377-383.

Sawada, N. et al. (Apr. 1998). "Induction of Thymidine Phosphorylase Activity and Enhancement of Capecitabine Efficacy by Taxol/Taxotere in Human Cancer Xenografts," *Clinical Cancer Res.* 4(4):1013-1019.

Scagliotti, G. V. et al. (Nov. 1, 2002). "Phase III Randomized Trial Comparing Three Platinum-Based Doublets in Advanced Non-Small-Cell Lung Cancer," *J. Clin. Oncol.* 20:4285-4291.

Scagliotti, G. V. et al. (Jul. 20, 2008). "Phase III Study Comparing Cisplatin Plus Gemcitabine with Cisplatin Plus Pemetrexed in Chemotherapy-Naïve Patients with Advanced-Stage Non-Small-Cell Lung Cancer," *J. Clin. Oncol.* 26(21):3543-3551.

Schiller, J.H. et al., (Jan. 10, 2002). "Comparison of Four Chemotherapy Regimens for Advanced Non-Small-Cell Lung Cancer," *New England J. Med.* 346(2):92-98.

Schilsky, R.L. et al. (Jan. 15, 2002). "Dose-Escalating Study of Capecitabine Plus Gemcitabine Combination Therapy in Patients with Advanced Cancer," *J. Clin. Oncol.* 20(2):582-587.

Schnitzer, J.E. (Jan. 1992). "Gp60 is an Albumin-Binding Glycoprotein Expressed by Continuous Endothelium Involved in Albumin Transcytosis," *Am. J. Physiol.* 262(1, Pt. 2):H246-H254.

Schwonzen, M. et al. (2000). "Liposomal Doxorubicin and Weekly Paclitaxel in the Treatment of Metastatic Breast Cancer," *Anti-Cancer Drugs* 11:681-685.

Seidman, A.D. et al. (1993). "Taxol Plus Recombinant Human Granulocyte-Colony Stimulating Factor as Initial and as Salvage Chemotherapy for Metastatic Breast Cancer: A Preliminary Report," *J. of the National Cancer Institute Monographs* (15):171-175.

Shaked, Y. et al. (Jan. 2005). "Genetic Heterogeneity of the Vasculogenic Phenotype Parallels Angiogenesis: Implications for Cellular Surrogate Marker Analysis of Antiangiogenesis," *Cancer Cell* 7:101-111 and Supplemental Data located at <http://www.cancercell.org/cgi/content/full/7/1/101/DC1/>, last visited Apr. 30, 2007, four pages.

Shepherd, F. A. (Dec. 1995). "Phase II Trials of Single-Agent Activity of Gemcitabine in Patients with Advanced Non-Small Cell Lung Cancer: An Overview," *Anti-Cancer Drugs* 6(Suppl 6):19-25.

Shi, Q. et al. (Dec. 1997). "Antitumor Agents-CLXXV. Anti-Tubulin Action of (+)-Thiocolchine Prepared by Partial Synthesis," *Bioorg. Med. Chem.* 5(12):2277-2282.

Sledge, G.W. et al. (Feb. 15, 2003). "Phase III Trial of Doxorubicin, Paclitaxel, and the Combination of Doxorubicin and Paclitaxel as Front-line Chemotherapy for Metastatic Breast Cancer: an Intergroup Trial (E1193)," *J. Clin. Oncol.*21(4):588-592.

Socinski, M. (Oct. 2006). "Update on Nanoparticle Albumin-Bound Paclitaxel," *Clinical Advances in Hematology & Oncology* 4(10):745-746.

Socinski, M. A. et al. (Aug. 1, 2009). "PD3.3.4—Retrospective Analysis of a Phase II Study of nab-Paclitaxel plus Carboplatin in Advanced NSCLC: Response Based on Histology," *NSCLC—Advanced Disease I, International Association for the Study of Lung Cancer*, WCLC 13th World Conference on Lung Cancer, 2 pages.

Socinski, M. A. et al. (2009). "Retrospective Analysis of a Phase II Study of nab-Paclitaxel Plus Carboplatin in Advanced NSCLC, Response Based on Histology," *IASLC, 13th World Conference on Lung Cancer*, San Francisco, CA, Jul. 31-Aug. 4, 2009, Poster Discussion #PD3.3.4, one page.

Socinski, M. A. et al. (2010). "Results of a Randomized, Phase III Trial of Nab-Paclitaxel (nab-P) and Carboplatin (C) Compared with Cremophor-Based Paclitaxel (P) and Carboplatin as First-Line Therapy in Advanced Non-Small Cell Lung Cancer (NSCLC)," Abstract for 2010 American Society of Clinical Oncology Annual Meeting, Abstract Control No. 52889, located at http://www.asco.org/ASCOv2/Meetings/Abstracts?vmview=abst_detail_view&confID=74&abstractID=52889 <https://my.mofo.com/exchweb/bin/,DanaInfo=SSFEXC04-EVS1.mofo.com+redir.asp?URL=http://www.asco.org/ASCOv2/Meetings/Abstracts?vmview=abst_detail_view%26confID=74%26abstractID=52889>, last visited Oct. 10, 2010, *J. Clin. Oncol.* 28:18s (suppl. Abstr. LBA7511), 3 pages.

Socinski, M. A. et al. (Jun. 2010). "A Dose Finding Study of Weekly and Every-3-Week nab-Paclitaxel Followed by Carboplatin as First-Line Therapy in Patients with Advanced Non-Small Cell Lung Cancer," *J. Thorac. Oncol.* <https://my.mofo.com/dana-cached/help/empty.html>5(6):852-861.

Socinski, M. A. et al. (2012, e-pub. Apr. 30, 2012). Weekly Nab Paclitaxel in Combination With Carboplatin Versus Solvent-Based Paclitaxel Plus Carboplatin as First Line Therapy in Patients With Advanced Non-Small-Lung Cancer: Final Results of a Final Phase III Trial, *J. Clin. Oncol.* 8 pages.

Sonpavde, G. et al. (2008). Treatment of Metastatic Urothelial Cancer: Opportunities for Drug Discovery and Development, *BJU Int.* 102(9 Part B):1354-1360.

Sørensen, J. B. et al. (Mar. 1987). "Vinca Alkaloids in the Treatment of Non-Small Cell Lung Cancer," *Cancer Treatment Reviews* 14(1):29-51.

Sørensen, J. B. (1995). "Gemcitabine in Non-Small Cell Lung Cancer," *Lung Cancer* 12 (Suppl. 1):S173-S175.

Sparreboom, A. et al. (Jun. 1, 2005). "Comparative Preclinical and Clinical Pharmacokinetics of a Cremophor-Free, Nanoparticle Albumin-Bound Paclitaxel (ABI-007) and Paclitaxel Formulated in Cremophor (Taxol)," *Clin. Cancer Res.* 11(11):4136-4143.

Stinchcombe, T.E. et al. (2005). "Preliminary Results of Phase I Trial of Carboplatin (CP) in Combination with ABI-007 Administered Weekly or Every 3 Weeks in Patients (pts) With Solid Tumors," *Breast Cancer Research and Treatment, 28th Annual San Antonio Breast Cancer Symposium*, San Antonio, Texas, USA, Dec. 8-11, 2005, 94(1):S71, Abstract No. 1092.

(56) References Cited

OTHER PUBLICATIONS

Stinchcombe, T. E. et al. (Oct. 2007). "Phase I and Pharmacokinetic Trial of Carboplatin and Albumin-Bound Paclitaxel, ABI-007 (Abraxane) on Three Treatment Schedules in Patients with Solid Tumors," *Cancer Chemotherap. Pharmacol.* 60(5):759-766.

Stroyakovsky, D. L. et al. (Aug. 1, 2009). "PD3.4.1—Weekly and Every-3-Week Nab-Paclitaxel Followed by Carboplatin as First-Line Therapy is Effective in Patients With Advanced Non-Small Cell Lung Cancer: Final Results of a Phase II Study," NSCLC—Advanced Disease I, Poster Discussion, 13th World Conference on Lung Cancer, located at www.2009worldlungcancer.org <http://www.2009worldlungcancer.org>, <http://abstracts/webges.com/itinerary/itinerary.php?i=1&abstract=2157&keyword=paclitaxel>, last visited on Nov. 11, 2010, 2 pages.

Stroyakovsky, D. L. et al. (2009). "Weekly and Every-3-Week nab—Paclitaxel Followed by Carboplatin as First-Line Therapy is Effective in Patients With Advanced Non-Small Cell Lung Cancer: Final Results of a Phase II Study," *IASLC, 13th World Conference on Lung Cancer*, San Francisco, CA, Jul. 31-Aug. 4, 2009, Poster Discussion # PD3.4.1, one page.

Sugio, S. et al. (1999). "Crystal Structure of Human Serum Albumin at 2.5 A Resolution," *Protein. Eng.* 12(6):439-446.

Tao, C. et al. (2005). "Preparation of Nanoparticle Albumin Bound 17AAG (nab-17AAG) Suitable for Intravenous Administration," *Proc. Amer. Assoc. Cancer Res.* vol. 46, Experimental and Molecular Therapeutics 10: Drug Targeting, Abstract No. 1435, located at <http://www.aacrmeetingabstracts.org/cgi/content/abstract/2005/1/336-b?maxtosh . . . >, last visited Nov. 29, 2007, two pages.

Tao, C. et al. (2006). "Preparation and Evaluation of Novel Derivatives of Geldanamycin," Abstract 1121, *Proc. Amer. Assoc. Cancer Res.* vol. 47, Chemistry 2: Drug Discovery 1: Screening, Synthesis, and Structure-Activity Relationships, Abstract No. 1121, located at <http://www.aacrmeetingabstracts.org/cgi/content/abstract/2006/1/265>, last accessed on Jul. 22, 2009, two pages.

TARCEVA® (Erlotinib) Prescribing Product Label Information for Tablets, Oral Administration of TARCEVA® (revised as Apr. 2009). Initial U.S. Approval: 2004, Manufactured for: OSI Pharmaceuticals, Inc. Melville, NY 11747; Manufactured by Schwarz Pharma Manufacturing, Seymour, IN 47274; Distributed by Genentech USA, Inc. CA 94080-4990; Under Section 14 of "Clinical Studies", see specifically Sections Nos. 14.1 entitled "NSCLC—TARCEVA Administered Concurrently with Chemotherapy," and 14.2 entitled "Pancreatic Cancer—TARCEVA Administered Concurrently with Gemcitabine," 4 pages.

Ten Tije, a. J. et al. (2003). "Pharmacological Effects of Formulation Vehicles, Implications for Cancer Chemotherapy," *Clin. Pharmacokinet.* 42(7):665-685.

Trieu, V. et al. (2008). "Pharmacokinetic and ADME Study of Nanoparticle Albumin-Bound 17AAG (nab-17AAG) in Mice," Pharmacology: Nanoparticles and New Drug Delivery Strategies: Poster, Abstract No. 5747, *presented at 99th AACR Annual Meeting*, Apr. 12-16, 2008, San Diego, CA, located at <http://www.aacrmeetingabstracts.org/cgi/content/meeting_abstract/2008/1_Annual_Meeting/5747>, last accessed on Jul. 22, 2009 two pages.

Trieu, V. et al. (Apr. 2008). "Cardiovascular and Respiratory Assessment Following IV Administration of Nanoparticle Albumin-Bound 17AAG (nab-17AAG) in Conscious Cynomolgus Monkeys" Poster, *presented at 99th AACR Annual Meeting*, San Diego, CA, Apr. 12-16, 2008, Abstract No. 5746.

Tsai, J. Y. et al. (Aug. 2003). "Combined Modality Therapy for Pancreatic Cancer," *Seminars in Oncology* 30(4): Suppl. 9, pp. 71-79.

Tullis, J.L. (Jan. 31, 1977). "Albumin," *JAMA* 237(5):460-463.

Ueda, M. et al. (Jul. 2006). "Gemcitabine Interferon-α-+CDDP+5-FU—Preliminary Report," *Jpn. J. Cancer Chemother.* 33(7):937-940. (English Summary Only.)

Urien, S. et al. (1996). "Docetaxel Serum Protein Binding with High Affinity to Alpha1-Acid Glycoprotein," *Invest. New Drugs*, 14:147-151.

Van Cutsem, E. et al. (Apr. 15, 2004). "Phase III Trial of Gemcitabine Plus Tipifarnib Compared With Gemcitabine Plus Placebo in Advanced Pancreatic Cancer," *J. Clin. Oncology* 22(8):1430-1438.

Vogel, C. (Oct. 1, 2005). "Nab Paclitaxel," *Breast Cancer Update Nurses* 3(2): p. 12.

Von Hoff, D. D. et al. (2009). "SPARC Correlation with Response to Gemcitabine (G) Plus nab®-Paclitaxel (nab-P) in Patients with Advanced Pancreatic Cancer," *American Society of Clinical Oncology (ASCO)*, May 29-Jun. 2, 2009, Orlando, Florida, 27(155) (May 20 Supplement), Abstract No. 4525, 1 page (Poster).

Von Hoff, D. D. et al. (2009). "SPARC Correlation with Response to Gemcitabine (G) Plus nab®-Paclitaxel (nab-P) in Patients with Advanced Pancreatic Cancer: A Phase I/II Study," published by the American Society of Clinical Oncology, *2009 ASCO Annual Meeting*, Poster Discussion, Gastrointestinal (noncolorectal cancer), Abstract No. 4525, *J. Clin. Oncol.* 27:15s, 2009 (Suppl: Abstract 4525), located at <http://www.asco.org/ASCOv2/Meetings/Abstracts?&vmview=abst_detail_view&confID=65&abstractID=35160>, last visited on Feb. 18, 2010, 3 pages (Abstract).

Vorum, H. (Nov. 1999). "Reversible Ligand Binding to Human Serum Albumin. Theoretical and Clinical Aspects," *Dan. Med. Bull.* 46(5):379-399.

Welch, S. A. et al. (Jun. 1, 2007) "Combination Chemotherapy in Advanced Pancreatic Cancer: Time to Raise The White Flag?" *J. Clin. Oncol.* 25(16):2159-2161.

Willet, C. G. et al. (Dec. 2003). "Update on Combined-Modality Treatment Options for Pancreatic Cancer," *Oncology* 17(12): Suppl. 13, pp. 29-36.

Wozniak, A. J. et al. (Jul. 1998). "Randomized Trial Comparing Cisplatin with Cisplatin plus Vinorelbine in the Treatment of Advanced Non-Small-Cell Lung Cancer: A Southwest Oncology Group Study," *J. Clin. Oncol.* 16(7):2459-2465.

Written Opinion dated Jul. 11, 2011, for PCT Patent Application No. PCT/US2011/037462, filed on May 20, 2011, 7 pages.

Written Opinion dated Jul. 7, 2006 for PCT Application No. PCT/US2006/006167, filed on Feb. 21, 2006, 7 pages.

Written Opinion dated Mar. 17, 2008, for PCT Application No. PCT/US2007/023446, filed on Nov. 6, 2007, 6 pages.

Yoo, S.-H. et al. (2003). "Expression of Caveolin-1 is Associated with Poor Prognosis of Patients with Squamous Cell Carcinoma of the Lung," *Lung Cancer* 42:195-202.

Zalcberg, J. et al. (May 1998). "Phase II Study of Docetaxel and Cisplaten in Advanced Non-small-cell Lung Cancer," *J. Clin. Onc.* 16(5):1948-1953.

Zaniboni, A. et al. (May 20, 2014). "Gemcitabine Plus Nab-Paclitaxel as Second Line and beyond for Metastatic Pancreatic Cnacer (MPC): A Single Institution Retropective Analysis," 2014 ASCO Annual Meeting Abstracts, 32(15):Abstract e15202, two pages.

Zeinalova, K. P. et al. (2005). "Avastin (Bevacizumab) In Treating Malignant Tumors: New Data," *Farmateka* 18(113):22-26, with English translation (5 pages).

Non-Final Office Action dated Jan. 30, 2015, for U.S. Appl. No. 13/701,002, filed Apr. 12, 2013, 15 pages.

Non-Final Office Action dated Jan. 30, 2015, for U.S. Appl. No. 13/783,122, filed Mar. 1, 2013, 15 pages.

Non-Final Office Action dated Feb. 11, 2015, for U.S. Appl. No. 13/701,001, filed May 20, 2011, 15 pages.

Non-Final Office Action dated Feb. 12, 2015, for U.S. Appl. No. 13/782,992, filed Mar. 1, 2013, 15 pages.

Non-Final Office Action dated Sep. 24, 2015, for U.S. Appl. No. 13/701,002, filed May 20, 2011, 15 pages.

Non-Final Office Action dated Sep. 24, 2015, for U.S. Appl. No. 13/783,122, filed Mar. 1, 2013, 13 pages.

U.S. Appl. No. 61/318,774, filed Mar. 29, 2010, for Desai et al.
U.S. Appl. No. 61/318,777, filed Mar. 29, 2010, for Desai et al.
U.S. Appl. No. 14/714,131, filed May 15, 2015, by Seward et al.
U.S. Appl. No. 15/160,598, filed May 20, 2016, for Yeo et al.
U.S. Appl. No. 15/183,636, filed Jun. 15, 2016, for Desai et al.
U.S. Appl. No. 15/217,763, filed Jul. 22, 2016, for Desai et al.
U.S. Appl. No. 15/287,613, filed Oct. 6, 2016, for Desai et al.

(56) References Cited

OTHER PUBLICATIONS

U.S. Appl. No. 15/302,134, filed Apr. 3, 2015, for Desai et al.
Shah, A.N. et al. (2007, e-published on Oct. 2, 2007). "Development and Characterization of Gemcitabine-Resistant Pancreatic Tumor Cells," *Annuals of Surgical Oncology* 14(12):3629-3637.
U.S. Appl. No. 15/239,680, filed Aug. 17, 2016, for Desai et al.
U.S. Appl. No. 15/361,851, filed Nov. 28, 2016, for Desai et al.
U.S. Appl. No. 15/364,189, filed Nov. 29, 2016, for Desai et al.
U.S. Appl. No. 15/399,366, filed Jan. 5, 2017, for Pierce et al.
U.S. Appl. No. 15/412,897, filed Jan. 23, 2017, for Foss et al.
U.S. Appl. No. 15/462,361, filed Mar. 17, 2017, for Tao et al.
Arioka, H. (Oct. 29, 2005). "The Taxanes—Paclitaxel and Docetaxel," *Medical Footsteps* 215(5)368-371. (Translation of the Abstract Only).

Figure 1: CT scan showing early response in a target lesion
A. Baseline 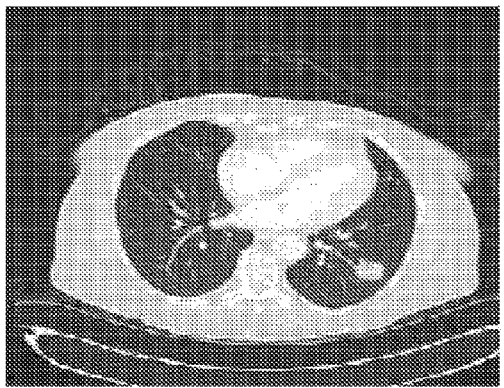
B. After 2 cycles of therapy 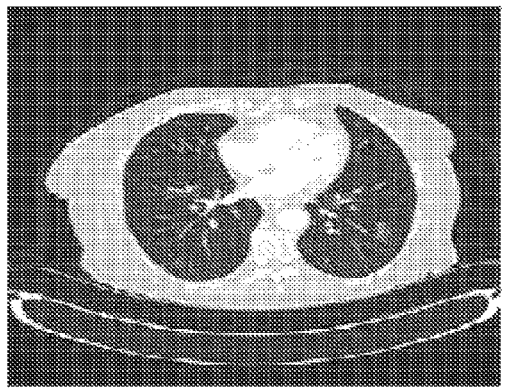

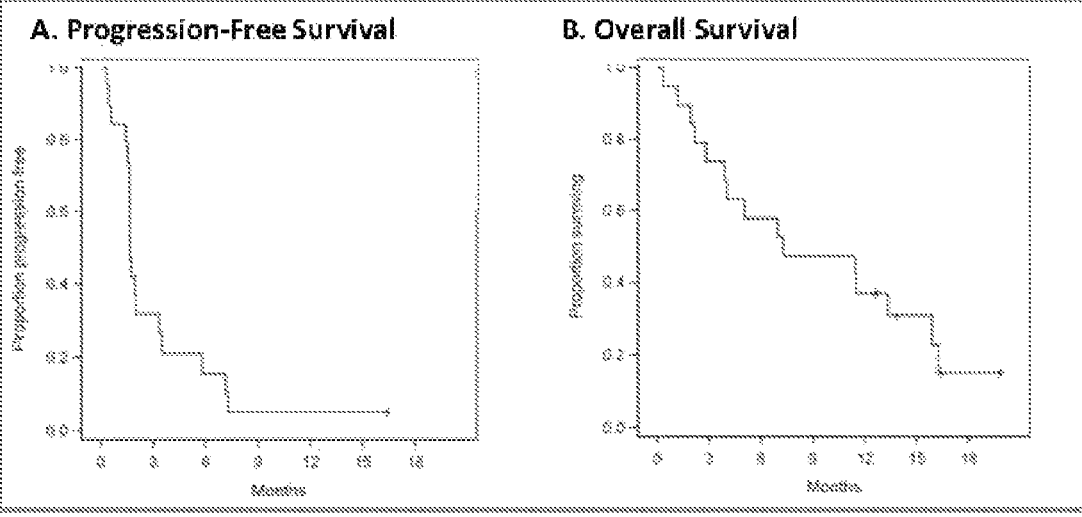

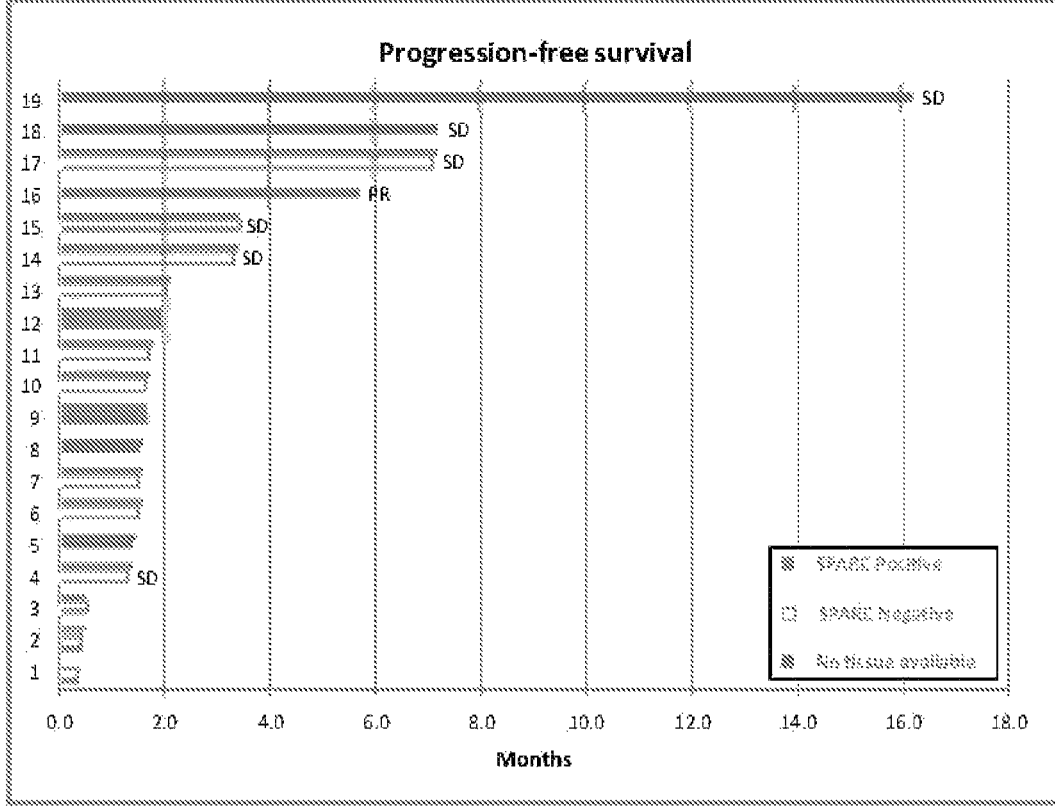

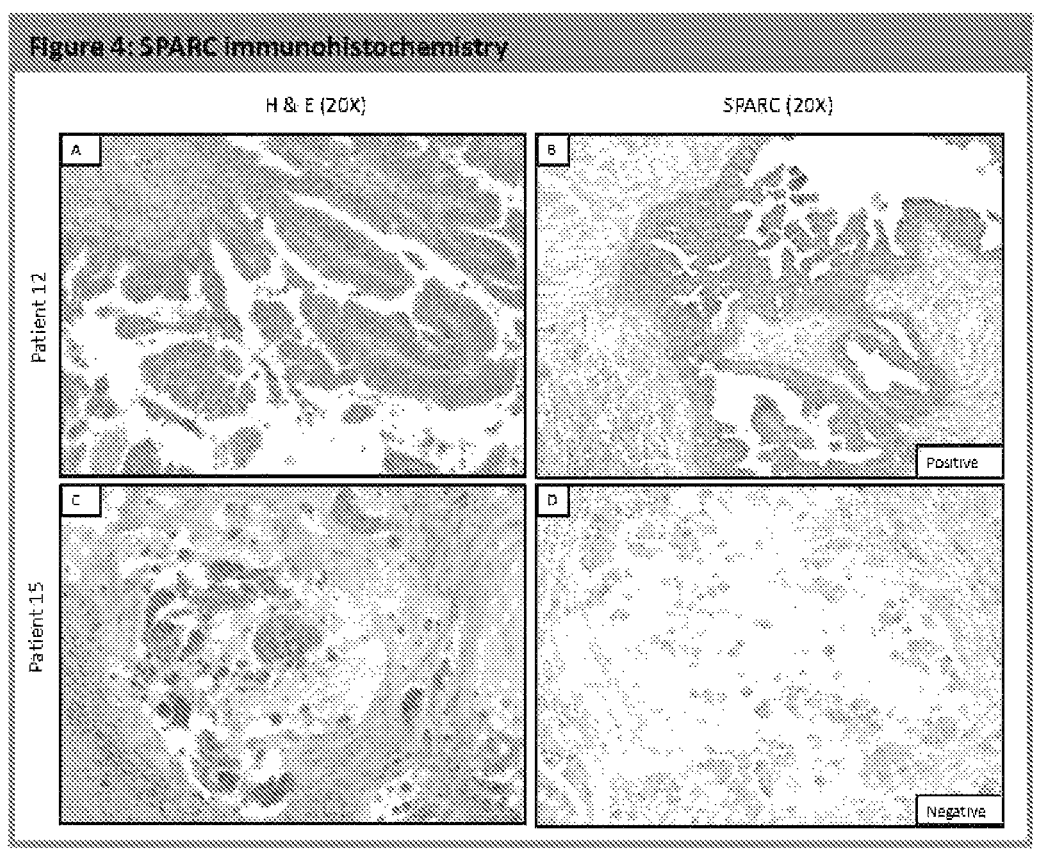

METHODS OF TREATMENT OF PANCREATIC CANCER

CROSS-REFERENCE TO RELATED APPLICATIONS

This application is a continuation of U.S. patent application Ser. No. 13/701,002, having an international filing date of May 20, 2011; which is a National Phase filing under 35 U.S.C. §371 of International Application No. PCT/US2011/037462, having an international filing date of May 20, 2011; which claims priority benefit to U.S. Provisional Patent Application Nos. 61/351,846, filed Jun. 4, 2010, 61/377,035, filed Aug. 25, 2010, and 61/446,932, filed Feb. 25, 2011, the contents of each are hereby incorporated herein by reference in their entirety.

TECHNICAL FIELD

The present invention relates to methods and compositions for the treatment of pancreatic cancer in an individual by administering compositions comprising nanoparticles that comprise a taxane and an albumin as a second-line therapy.

BACKGROUND

Pancreatic cancer has one of the highest mortality rates among all cancers and is the fourth most common cause of adult cancer death in the United States with an estimated 42,470 cases per year. See Nieto et al., *The Oncologist*, 13:562-576 (2008); and Cancer Facts and Figures, *American Cancer Society* (2009). It accounts for about 3% of all newly diagnosed cancers in the United States each year. However, almost double that number cancer patients, about 6%, die from pancreatic cancer. See Cancer Facts and Figures, *American Cancer Society* (2009). The high mortality rate from pancreatic cancer is a result of the high incidence of metastatic disease at the time of diagnosis. As a result, only 5%-15% of patients are candidates present with tumors are amenable to resection. See Nieto et al, *The Oncologist*, 13:562-576 (2008).

The standard first-line treatment for treating pancreatic cancer is gemcitabine (e.g., GEMZAR®), which was approved by the Food and Drug Administration ("FDA") in 1996. In a clinical study with 126 patients with locally advanced pancreatic cancer (63 treated with gemcitabine), gemcitabine was shown to be superior to 5-fluororuracil (5-FU) in terms of median overall survival (5.7 months for gemcitabine versus 4.2 months for 5-FU), median time to disease progression (2.1 months for gemcitabine versus 0.9 months for 5-FU), and clinical benefit responses. However, although gemcitabine has become a standard palliative therapy for treating pancreatic cancer since its approval in 1996, there has been little improvement in pancreatic cancer treatment. For all stages of pancreatic cancer combined, the 5-year relative survival rate for pancreatic cancer between 1996 and 2004 was 5%, drastically lower than survival rates for other cancers. See American Cancer Society, Surveillance and Health Policy Research (2009).

Multiple studies have been conducted but failed to identify an improved therapeutic regime for treating pancreatic cancer by combining gemcitabine with a second agent. The only exception to the failed attempts to identify effective combination therapy regime was the combination of gemcitabine and erlotinib (e.g., TARCEVA®). See Moore et al., *J. Clin. Oncol.* 25:1960-1966 (2007). The gemcitabine/erlotinib combination improved the median overall survival (6.4 months versus 6.0 months) and median progression free survival (3.8 months versus 3.5 months) over gemcitabine monotherapy. See id. Based on this very modest improvement in overall survival and progression free survival (0.4 and 0.3 months, respectively), the FDA approved the gemcitabine/erlotinib combination in 2005. Despite its approval, the gemcitabine/erlotinib combination has not been widely used as a standard of care for treating pancreatic cancer because of side effects associated with the gemcitabine/erlotinib combination and the minimal improvement on survival over gemcitabine monotherapy. See Nieto et al., *The Oncologist*, 13:562-576 (2008).

To date, no standard guidelines for second-line treatment of pancreatic cancer have been established. Data supporting the use of second-line therapy compared to best supportive care is lacking. Benefits of second-line therapy seems to be modest, at the cost of drug toxicity. Almhanna et al., 2008, Oncology, Vol. 22, No. 10.

Taxanes have been investigated as a second-line treatment in gemcitabine-resistant pancreatic cancer patients. In a small study, weekly paclitaxel treatment in 18 patients with recurrent disease produced a response rate of 6% and a median overall survival of 17.5 weeks. Almhanna et al., *Oncology*, 22:10 (2008). In two small studies using a combination of docetaxel and gefitinib, the median overall survival was about 12 weeks. Capecitabine was also combined with docetaxel, with response rates ranging from 1% to 12% and a median overall survival of 13 weeks. In a study of 15 patients, the combination of docetaxel with mitomycin and irinotecan produced no response and the median overall survival was 24 weeks. Clinical benefits were not reported in any of these studies. Almhanna et al., *Oncology*, 22:10 (2008).

Albumin bound paclitaxel (e.g., ABRAXANE®) in combination with gemcitabine was found to be well tolerated in advanced pancreatic cancer in a Phase I/II study and showed evidence of antitumor activity. See, for example, US Patent App. No. 2006/0263434; Maitra et al., *Mol. Cancer Ther.* 8(12 Suppl):C246 (2009); Loehr et al., *J. of Clinical Oncology* 27(15S)(May 20 Supplement):200, Abstract No. 4526 (2009); Von Hoff et al., *J. of Clinical Oncology* 27(15S) (May 20 Supplement), Abstract No. 4525 (2009); and Kim et al., *Proc. Amer. Assoc. Cancer Res.*, 46, Abstract No. 1440 (2005).

The disclosures of all publications, patents, patent applications and published patent applications referred to herein are hereby incorporated by reference in their entirety.

BRIEF SUMMARY OF THE INVENTION

The present invention in some embodiments provides a method of treating pancreatic cancer (such as advanced pancreatic cancer) in an individual in need thereof, comprising (or consisting of or consisting essentially of) administering to the individual an effective amount of a composition comprising nanoparticles comprising a taxane and an albumin (hereinafter also referred to as "the nanoparticle composition" or "taxane nanoparticle composition"), wherein the individual has been previously treated for pancreatic cancer (hereinafter also referred to "the prior therapy").

In some embodiments, the prior therapy comprises administration of gemcitabine ("a gemcitabine-based therapy"). In some embodiments, the prior therapy is gemcitabine monotherapy. In some embodiments, the prior therapy comprises the administration of gemcitabine and erlotinib. In some embodiments, the prior therapy comprises the administration of gemcitabine and capecitabine. In some embodiments, the prior therapy comprises the administration of gemcitabine and 5-FU. In some embodiments, the prior therapy comprises the administration of gemcitabine, erlotinib, capecitabine, and/or 5-FU. In some embodiments, the prior therapy is adjuvant gemcitabine therapy. In some embodiments, the prior therapy is neoadjuvant gemcitabine therapy.

In some embodiments, the individual has progressed on the prior therapy at the time of treatment. For example, the individual has progressed within any of about 1, 2, 3, 4, 5, 6, 7, 8, 9, 10, 11, or 12 months upon treatment with the prior therapy. In some embodiments, the individual is resistant or refractory to the prior therapy. In some embodiments, the individual has recurrent pancreatic cancer, i.e., the individual is initially responsive to the treatment with the prior therapy, but develops pancreatic cancer after about any of about 6, 7, 8, 9, 10, 11, 12, 24, or 36 months upon the cessation of the prior therapy.

Although the description below describes individuals who have progressed on a prior therapy (such as a gemcitabine-based therapy) as exemplary embodiments, it is understood that the description herein also applies to individuals who are resistant or refractory to the prior therapy, individuals who are unsuitable to continue with the prior therapy (for example due to failure to respond and/or due to toxicity), individuals who have recurrent pancreatic disease after the prior therapy, individuals who are non-responsive to the prior therapy, individuals who exhibit a less desirable degree of responsiveness and/or individuals who exhibit enhanced responsiveness. The methods described herein include all second-line therapies for treating pancreatic cancers that involve the administration of a composition comprising nanoparticles comprising albumin and a taxane. The methods described herein also include all third-line therapies for treating pancreatic cancers that involve the administration of a composition comprising nanoparticles comprising albumin and a taxane.

Thus, in some embodiments, there is provided a method of treating pancreatic cancer (such as advanced pancreatic cancer) in an individual in need thereof, comprising (or consisting of or consisting essentially of) administering to the individual an effective amount of a composition comprising nanoparticles comprising a taxane and an albumin, wherein the individual has progressed on prior therapy (for example progressed after any of about 3, 6, 9, or 12 months upon initiation of the prior therapy). In some embodiments, the prior therapy is gemcitabine-based therapy, erlotinib-based therapy, or 5-FU-based therapy. In some embodiments, the method does not comprise administering gemcitabine. In some embodiments, the method comprises administering gemcitabine in conjunction with the nanoparticle composition. In some embodiments, the method does not comprise the administration of a platinum-based agent (such as carboplatin or cisplatin). In some embodiments, the method does not comprise administration of an inhibitor of the hedgehog signaling pathway (a hedgehog inhibitor). In some embodiments, the taxane is paclitaxel. In some embodiments, the albumin is human serum albumin. In some embodiments, the nanoparticles comprise paclitaxel coated with albumin. In some embodiments, the average particle size of the nanoparticles in the nanoparticle composition is no more than about 200 nm (such as less than about 200 nm). In some embodiments, the composition comprises the albumin stabilized nanoparticle formulation of paclitaxel (Nab-paclitaxel (which is used interchangeably with the term "ABRAXANE®")). In some embodiments, the composition is Nab-paclitaxel (ABRAXANE®).

In some embodiments, there is provided a method of treating pancreatic cancer in an individual in need thereof, comprising administering to the individual an effective amount of a composition comprising nanoparticles comprising a taxane and an albumin, wherein the taxane is coated with the albumin, wherein the individual has progressed on a prior therapy (such as a gemcitabine-based therapy). In some embodiments, there is provided a method of treating pancreatic cancer in an individual in need thereof, comprising administering to the individual an effective amount of a composition comprising nanoparticles comprising a taxane and an albumin, wherein the average particle size of the nanoparticles in the nanoparticle composition is no greater than about 200 nm (such as less than about 200 nm), wherein the individual has progressed on gemcitabine-based therapy. In some embodiments, there is provided a method of treating pancreatic cancer in an individual in need thereof, comprising administering to the individual an effective amount of a composition comprising nanoparticles comprising a taxane and an albumin, wherein the taxane is coated with the albumin, wherein the average particle size of the nanoparticles in the nanoparticle composition is no greater than about 200 nm (such as less than about 200 nm), wherein the individual has progressed on gemcitabine-based therapy. In some embodiments, there is provided a method of treating pancreatic cancer in an individual in need thereof, comprising administering to the individual an effective amount of a composition comprising Nab-paclitaxel, wherein the individual has progressed on gemcitabine-based therapy. In some embodiments, there is provided a method of treating pancreatic cancer in an individual in need thereof, comprising administering to the individual an effective amount of Nab-paclitaxel, wherein the individual has progressed on gemcitabine-based therapy. In some embodiments, the method does not comprise administering gemcitabine. In some embodiments, the method comprises administering gemcitabine in conjunction with the nanoparticle composition. In some embodiments, the method does not comprise the administration of a platinum-based agent (such as carboplatin or cisplatin). In some embodiments, the method does not comprise administration of an inhibitor of the hedgehog signaling pathway (a hedgehog inhibitor).

In some embodiments, the composition is administered intravenously. In some embodiments, the composition is administered intraarterially. In some embodiments, the composition is administered intraperitoneally.

In some embodiments, levels of serum CA19-9 (carbohydrate antigen 19-9) in the individual administered with the composition comprising nanoparticles comprising a taxane and an albumin are decreased by at least about 50% (such as at least about any of 60%, 70%, 80%, 90%, 95%) in comparison to the levels of serum CA19-9 prior to the treatment.

In some embodiments, there is provided a method of treating an individual having locally advanced, unresectable, or metastatic pancreatic ductal carcinoma, wherein the individual has progressed within 6 months (such as within any of about 5, 4, 3, 2, 1 month) of gemcitabine-based therapy, comprising administering (such as administering intravenously) to the individual an effective amount of a composition comprising nanoparticles comprising albumin and a taxane (such as nanoparticles comprising albumin and paclitaxel, for example ABRAXANE®). In some embodiments, the nanoparticle composition is administered weekly at the dose of 100 mg/m². In some embodiments, the administration is carried out three out of four weeks.

Also provided are combination therapy methods for treating pancreatic cancer. Thus, for example, in some embodiments, there is provided a method of treating pancreatic cancer in an individual in need thereof, comprising administering to the individual (a) an effective amount of a composition comprising nanoparticles comprising taxane and albumin; and (b) an effective amount of another agent. In some embodiments, the individual has progressed on a prior therapy (for example progressed after any of about 3, 6, 9, or 12 months upon initiation of the prior therapy). In some embodiments, the prior therapy is gemcitabine-based therapy, erlotinib-based therapy, or 5-FU-based therapy. In some embodiments, the nanoparticle composition and the other agent are administered simultaneously or sequentially. In some embodiments, the nanoparticle composition and the other agent are administered concurrently. In some embodiments, the taxane is paclitaxel. In some embodiments, the taxane is docetaxel. In some embodiments, the albumin is human serum albumin. In some embodiments, the nanoparticles comprise paclitaxel coated with albumin. In some embodiments, the average particle size of the nanoparticles in the nanoparticle composition is no more than about 200 nm. In some embodiments, the composition comprises the albumin stabilized nanoparticle formulation of paclitaxel (Nab-paclitaxel (ABRAXANE®)). In some embodiments, the composition is Nab-paclitaxel (ABRAXANE®).

In some embodiments of any of the above embodiments related to combination therapy, the other agent is not gemcitabine. In some embodiments, the other agent is not a platinum-based agent (such as carboplatin or cisplatin). In some embodiments, the method does not comprise administration of an inhibitor of the hedgehog signaling pathway (a hedgehog inhibitor).

In some embodiments of any of the above embodiments related to combination therapy, the other agent is an antimetabolite agent, a tyrosine kinase inhibitors (e.g., an EGFR inhibitor), a matrix metalloproteinase inhibitor, a topoisomerase inhibitor, a proteasome inhibitor, a platinum-based agents, a therapeutic antibody, a farnesyltransferase inhibitor, an anti-angiogenic agent, and a macrolide. In some embodiments, the other agent is vandetanib, 5-fluororuracil, erlotinib, gefitnib, marimastat, irinotecan, tipifarnib, pemetrexed, exatecan, capecitabine, raltitrexed, cetuximab, bevacizumab, bortezomib, rapamycin, or gemcitabine.

In some embodiments, there is provided a method of treating pancreatic cancer in an individual in need thereof, comprising administering to the individual (a) an effective amount of a composition comprising nanoparticles comprising taxane and albumin; and (b) an effective amount of erlotinib, wherein the individual has progressed on gemcitabine-based therapy.

In some embodiments, there is provided a method of treating pancreatic cancer in an individual in need thereof, comprising administering to the individual (a) an effective amount of a composition comprising nanoparticles comprising taxane and albumin; and (b) an effective amount of an inhibitor of VEGFR2 and EGFR (hereinafter referred to as the "VEGFR/EGFR inhibitor").

In some embodiments, there is provided a method of treating pancreatic cancer in an individual in need thereof, comprising administering to the individual (a) an effective amount of a composition comprising nanoparticles comprising taxane and albumin; and (b) an effective amount of vandetanib. In some embodiments, the individual has not previously been treated for pancreatic cancer. In some embodiments, the individual has been previously treated for pancreatic cancer. In some embodiments the individual has failed gemcitabine-based therapy.

Pancreatic cancers that can be treated with methods described herein include, but are not limited to, exocrine pancreatic cancers and endocrine pancreatic cancers. Exocrine pancreatic cancers include, but are not limited to, adenocarcinomas, acinar cell carcinomas, adenosquamous carcinomas, colloid carcinomas, undifferentiated carcinomas with osteoclast-like giant cells, hepatoid carcinomas, intraductal papillary-mucinous neoplasms, mucinous cystic neoplasms, pancreatoblastomas, serous cystadenomas, signet ring cell carcinomas, solid and pseuodpapillary tumors, pancreatic ductal carcinomas, and undifferentiated carcinomas. In some embodiments, the exocrine pancreatic cancer is pancreatic ductal carcinoma.

Endocrine pancreatic cancers include, but are not limited to, insulinomas and glucagonomas.

In some embodiments, the pancreatic cancer is any of early stage pancreatic cancer, non-metastatic pancreatic cancer, primary pancreatic cancer, resected pancreatic cancer, advanced pancreatic cancer, locally advanced pancreatic cancer, metastatic pancreatic cancer, unresectable pancreatic cancer, pancreatic cancer in remission, recurrent pancreatic cancer, pancreatic cancer in an adjuvant setting, or pancreatic cancer in a neoadjuvant setting. In some embodiments, the pancreatic cancer is locally advanced pancreatic cancer, unresectable pancreatic cancer, or metastatic pancreatic ductal carcinoma. In some embodiments, the pancreatic cancer is resistant to the gemcitabine-based therapy. In some embodiments, the pancreatic cancer is refractory to the gemcitabine-based therapy.

The methods described herein can be used for any one or more of the following purposes: alleviating one or more symptoms of pancreatic cancer, delaying progression of pancreatic cancer, shrinking pancreatic cancer tumor size, disrupting (such as destroying) pancreatic cancer stroma, inhibiting pancreatic cancer tumor growth, prolonging overall survival, prolonging disease-free survival, prolonging time to pancreatic cancer disease progression, preventing or delaying pancreatic cancer tumor metastasis, reducing (such as eradiating) preexisting pancreatic cancer tumor metastasis, reducing incidence or burden of preexisting pancreatic cancer tumor metastasis, preventing recurrence of pancreatic cancer, and/or improving clinical benefit of pancreatic cancer.

Also provided are compositions (such as pharmaceutical compositions), medicine, kits, and unit dosages useful for methods described herein.

Provided herein are methods of treating pancreatic cancer in an individual in need thereof, comprising administering to the individual an effective amount of a composition comprising nanoparticles comprising a taxane and an albumin, wherein the individual has progressed on a gemcitabine-based therapy. In some embodiments, the progression is within less than about 12 months. In some embodiments, the gemcitabine-based therapy further comprises erlotinib. In some embodiments, the gemcitabine-based therapy is monotherapy.

Provided herein are methods of treating resistant or refractory pancreatic cancer in an individual in need thereof, comprising administering to the individual an effective amount of a composition comprising nanoparticles comprising a taxane and an albumin. In some embodiments, a prior therapy has stopped for at least 6 months when initiating administration to the individual of an effective amount of a composition comprising nanoparticles comprising a taxane and an albumin. In some embodiments, the prior therapy is a gemcitabine-based therapy. In some embodiments, the gemcitabine-based therapy further comprises erlotinib. In some embodiments, the gemcitabine-based therapy is monotherapy.

Provided herein are methods of treating recurrent pancreatic cancer in an individual in need thereof, comprising administering to the individual an effective amount of a composition comprising nanoparticles comprising a taxane and an albumin. In some embodiments, a prior therapy has stopped for at least 6 months when initiating administration to the individual of an effective amount of a composition comprising nanoparticles comprising a taxane and an albumin. In some embodiments, the prior therapy is a gemcitabine-based therapy. In some embodiments, the gemcitabine-based therapy further comprises erlotinib. In some embodiments, the gemcitabine-based therapy is monotherapy.

Provided herein are methods of treating pancreatic cancer in an individual in need thereof, comprising administering to the individual (a) an effective amount of a composition comprising nanoparticles comprising taxane and albumin; and (b) an effective amount of another agent, wherein the individual has progressed on gemcitabine-based therapy. In some embodiments, the nanoparticle composition and the other agent are administered simultaneously or sequentially. In some embodiments, the nanoparticle composition and the other agent are administered concurrently. In some embodiments, the other agent is selected from the group consisting of 5-fluororuracil, erlotinib, gefitnib, marimastat, irinotecan, tipifarnib, pemetrexed, exatecan, capecitabine, raltitrexed, cetuximab, bevacizumab, bortezomib, rapamycin, vandetanib and gemcitabine.

Provided herein are methods of treating pancreatic cancer in an individual in need thereof, comprising administering to the individual (a) an effective amount of a composition comprising nanoparticles comprising a taxane and an albumin, and (b) an effective amount of vandetanib. In some embodiments, the nanoparticle composition and the vandetanib are administered simultaneously or sequentially. In some embodiments, the nanoparticle composition and the vandetanib are administered concurrently.

In any of the embodiments disclosed herein, the pancreatic cancer is exocrine pancreatic cancer or endocrine pancreatic cancer. In any of the embodiments disclosed herein, the exocrine pancreatic cancer is pancreatic ductal carcinoma. In any of the embodiments disclosed herein, the pancreatic cancer is locally advanced pancreatic cancer, unresectable pancreatic cancer, or metastatic pancreatic ductal carcinoma. In any of the embodiments disclosed herein, the composition comprising nanoparticles comprising taxane and albumin is administered parenterally. In any of the embodiments disclosed herein, the composition comprising nanoparticles comprising taxane and albumin is administered intravenously or intraarterially. In any of the embodiments disclosed herein, the taxane is paclitaxel. In any of the embodiments disclosed herein, the nanoparticles in the composition have an average diameter of no greater than about 200 nm. In any of the embodiments disclosed herein, the nanoparticles in the composition have an average diameter of less than about 200 nm. In any of the embodiments disclosed herein, the taxane in the nanoparticles are coated with albumin. In any of the embodiments disclosed herein, the individual is human. In any of the embodiments disclosed herein, levels of serum CA19-9 (carbohydrate anti-gen 19-9) in the individual are decreased by at least about 50% in comparison to the levels of serum CA19-9 prior to the treatment.

These and other aspects and advantages of the present invention will become apparent from the subsequent detailed description and the appended claims. It is to be understood that one, some, or all of the properties of the various embodiments described herein may be combined to form other embodiments of the present invention.

BRIEF DESCRIPTION OF FIGURES

FIG. 1 shows early response in a target lesion of the baseline level and after 2 cycles of therapy with an albumin stabilized nanoparticle formulation of paclitaxel (i.e., Nab-paclitaxel).

FIG. 2 is a Kaplan-Meier Survival Curves showing progression-free survival (FIG. 2A) and overall survival (FIG. 2B) after treatments with Nab-paclitaxel in Stages III and IV pancreatic cancer patients.

FIG. 3 is a correlation between SPARC (Secreted Protein Rich in Cysteine) IHC (Immunohistochemsitry) and PFS (Progression-Free Survival). SD: Stable Disease; PR: Partial Response.

FIG. 4 is a SPARC immunohistochemistry of two different pancreatic cancer patients.

DETAILED DESCRIPTION OF THE INVENTION

The present invention provides methods and compositions for treating pancreatic cancer (such as advanced pancreatic cancer) in an individual as a second-line therapy (e.g., an individual who has been previously treated for pancreatic cancer) by administering a composition comprising nanoparticles comprising a taxane and an albumin. The method can either be a monotherapy or a combination therapy.

In a phase II trial in a population of patients with locally advanced, unresectable or metastatic pancreatic ductal carcinoma who progressed on gemcitabine-based therapy, we have found that an albumin stabilized nanoparticle formulation of paclitaxel, namely, Nab-paclitaxel, provided clinical benefit (partial response or disease stabilization) in about 37% of patients treated, and about 21% of patients remained on therapy for at least 6 months. The levels of serum CA19-9 were also found to decrease by about 52% in patients who had stable disease or partial response in comparison to about 18% decrease in patients with progressive disease.

In one aspect, there is provided a method of treating pancreatic cancer (such as advanced pancreatic cancer) in an individual in need thereof, comprising administering to the individual an effective amount of a composition comprising nanoparticles comprising a taxane and an albumin, wherein the individual has been previously treated for pancreatic cancer.

In another aspect, there is provided a method of treating pancreatic cancer (such as advanced pancreatic cancer) in an individual in need thereof, comprising administering to the individual (a) an effective amount of a composition comprising nanoparticles comprising taxane and albumin; and (b) an effective amount of another agent, wherein the individual has been previously treated for pancreatic cancer.

In another aspect, there is provided a method of treating pancreatic cancer (such as advanced pancreatic cancer) in an individual in need thereof, comprising administering to the individual (a) an effective amount of a composition comprising nanoparticles comprising taxane and albumin; and (b) an effective amount of vandetanib. In some embodiments, the individual has been previously treated for pancreatic cancer. In some embodiments, the individual has not been previously treated for pancreatic cancer.

Also provided are compositions (such as pharmaceutical compositions), medicine, kits, and unit dosages useful for the methods described herein.

Definitions

As used herein, "treatment" or "treating" is an approach for obtaining beneficial or desired results including clinical results. For purposes of this invention, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread (e.g., metastasis) of the disease, preventing or delaying the recurrence of the disease, delay or slowing the progression of the disease, ameliorating the disease state, providing a remission (partial or total) of the disease, decreasing the dose of one or more other medications required to treat the disease, delaying the progression of the disease, increasing or improving the quality of life, increasing weight gain, and/or prolonging survival. Also encompassed by "treatment" is a reduction of pathological consequence of pancreatic cancer. The methods of the invention contemplate any one or more of these aspects of treatment.

The term "individual" refers to a mammal and includes, but is not limited to, human, bovine, horse, feline, canine, rodent, or primate.

"Prior therapy" used herein refers to a therapeutic regime that is different from and was instituted prior to the methods of administering the nanoparticle compositions. The prior therapy generally, but not necessarily, does not involve the administration of the taxane nanoparticle composition. It is to be understood that the prior therapy may involve some of the same therapeutic agent(s) with the methods described herein.

As used herein, an "at risk" individual is an individual who is at risk of developing pancreatic cancer. An individual "at risk" may or may not have detectable disease, and may or may not have displayed detectable disease prior to the treatment methods described herein. "At risk" denotes that an individual has one or more so-called risk factors, which are measurable parameters that correlate with development of pancreatic cancer, which are described herein. An individual having one or more of these risk factors has a higher probability of developing cancer than an individual without these risk factor(s).

"Adjuvant setting" refers to a clinical setting in which an individual has had a history of pancreatic cancer, and generally (but not necessarily) been responsive to therapy, which includes, but is not limited to, surgery (e.g., surgery resection), radiotherapy, and chemotherapy. However, because of their history of pancreatic cancer, these individuals are considered at risk of development of the disease. Treatment or administration in the "adjuvant setting" refers to a subsequent mode of treatment. The degree of risk (e.g., when an individual in the adjuvant setting is considered as "high risk" or "low risk") depends upon several factors, most usually the extent of disease when first treated.

"Neoadjuvant setting" refers to a clinical setting in which the method is carried out before the primary/definitive therapy.

As used herein, "delaying" the development of pancreatic cancer means to defer, hinder, slow, retard, stabilize, and/or postpone development of the disease. This delay can be of varying lengths of time, depending on the history of the disease and/or individual being treated. As is evident to one skilled in the art, a sufficient or significant delay can, in effect, encompass prevention, in that the individual does not develop the disease. A method that "delays" development of pancreatic cancer is a method that reduces probability of disease development in a given time frame and/or reduces the extent of the disease in a given time frame, when compared to not using the method. Such comparisons are typically based on clinical studies, using a statistically significant number of subjects. Pancreatic cancer development can be detectable using standard methods, including, but not limited to, computed tomography (CT Scan, e.g., helical spiral CT scan), endoscopic ultrasound (EUS), endoscopic retrograde cholangiopancreatography (ERCP), laparoscopy, or biopsy (e.g., percutaneous needle biopsy or fine needle aspiration). Development may also refer to pancreatic cancer progression that may be initially undetectable and includes recurrence.

As used herein, by "combination therapy" is meant that a first agent be administered in conjunction with another agent. "In conjunction with" refers to administration of one treatment modality in addition to another treatment modality, such as administration of a nanoparticle composition described herein in addition to administration of the other agent to the same individual. As such, "in conjunction with" refers to administration of one treatment modality before, during, or after delivery of the other treatment modality to the individual.

The term "effective amount" used herein refers to an amount of a compound or composition sufficient to treat a specified disorder, condition or disease such as ameliorate, palliate, lessen, and/or delay one or more of its symptoms. In reference to pancreatic cancer, an effective amount comprises an amount sufficient to cause a tumor to shrink and/or to decrease the growth rate of the tumor (such as to suppress tumor growth) or to prevent or delay other unwanted cell proliferation in pancreatic cancer. In some embodiments, an effective amount is an amount sufficient to delay development of pancreatic cancer. In some embodiments, an effective amount is an amount sufficient to prevent or delay recurrence. An effective amount can be administered in one or more administrations. In the case of pancreatic cancer, the effective amount of the drug or composition may: (i) reduce the number of pancreatic cancer cells; (ii) reduce tumor size; (iii) inhibit, retard, slow to some extent and preferably stop pancreatic cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; (vii) relieve to some extent one or more of the symptoms associated with pancreatic cancer; and/or (viii) disrupting (such as destroying) pancreatic cancer stroma.

The term "simultaneous administration," as used herein, means that a first therapy and second therapy in a combination therapy are administered with a time separation of no more than about 15 minutes, such as no more than about any of 10, 5, or 1 minutes. When the first and second therapies are administered simultaneously, the first and second therapies may be contained in the same composition (e.g., a composition comprising both a first and second therapy) or in separate compositions (e.g., a first therapy in one composition and a second therapy is contained in another composition).

As used herein, the term "sequential administration" means that the first therapy and second therapy in a combination therapy are administered with a time separation of more than about 15 minutes, such as more than about any of 20, 30, 40, 50, 60, or more minutes. Either the first therapy or the second therapy may be administered first. The first and second therapies are contained in separate compositions, which may be contained in the same or different packages or kits.

As used herein, the term "concurrent administration" means that the administration of the first therapy and that of a second therapy in a combination therapy overlap with each other.

As used herein, by "pharmaceutically acceptable" or "pharmacologically compatible" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

It is understood that aspect and embodiments of the invention described herein include "consisting" and/or "consisting essentially of" aspects and embodiments.

Reference to "about" a value or parameter herein includes (and describes) variations that are directed to that value or parameter per se. For example, description referring to "about X" includes description of "X".

As used herein and in the appended claims, the singular forms "a," "or," and "the" include plural referents unless the context clearly dictates otherwise.

Where aspects or embodiments of the invention are described in terms of a Markush group or other grouping of alternatives, the present invention encompasses not only the entire group listed as a whole, but each member of the group individually and all possible subgroups of the main group, but also the main group absent one or more of the group members. The present invention also envisages the explicit exclusion of one or more of any of the group members in the claimed invention.

Methods of Treating Pancreatic Cancer

The invention provides methods of treating pancreatic cancer (such as advanced pancreatic cancer) in an individual (such as human) comprising administering to the individual an effective amount of a composition comprising nanoparticles comprising a taxane and an albumin, wherein the individual has been previously treated for pancreatic cancer (also referred to as the "prior therapy").

The present invention also provides methods of treating pancreatic cancer (such as advanced pancreatic cancer) in an individual (such as human) comprising administering to the individual a) an effective amount of a composition comprising nanoparticles comprising a taxane and an albumin; and b) an effective amount of another agent, wherein the individual has been previously treated for pancreatic cancer.

It is understood that reference to and description of methods of treating pancreatic cancer below is exemplary and that this description applies equally to and includes methods of treating pancreatic cancer using combination therapy. Further, although the description below describes individuals who have progressed on a prior therapy (such as a gemcitabine-based therapy) as exemplary embodiments, it is understood that the description herein also applies to individuals who are resistant or refractory to the prior therapy, individuals who are unsuitable to continue with the prior therapy (for example due to failure to respond and/or due to toxicity), individuals who have recurrent pancreatic disease after the prior therapy, individuals who are non-responsive to the prior therapy, individuals who exhibit a less desirable degree of responsiveness and/or individuals who exhibit enhanced responsiveness. As used herein, responsiveness can be determined by levels of CA19-9, RECIST, CT scan, biopsy, immunohistochemistry and the like. The methods described herein include all second-line therapies for treating pancreatic cancers that involve the administration of a composition comprising nanoparticles comprising albumin and a taxane. The methods described herein also include all third-line therapies for treating pancreatic cancers that involve the administration of a composition comprising nanoparticles comprising albumin and a taxane.

In some embodiments, the individual has progressed on the prior therapy at the time of treatment. For example, the individual has progressed within any of about 1, 2, 3, 4, 5, 6, 7, 8, 9, 10, 11, or 12 months upon treatment with the prior therapy. In some embodiments, the individual is resistant or refractory to the prior therapy. In some embodiments, the individual is unsuitable to continue with the prior therapy (for example due to failure to respond and/or due to toxicity). In some embodiments, the individual has failed to respond to the prior therapy. In some embodiments, the individual is non-responsive to the prior therapy. In some embodiments, the individual is partially responsive to the prior therapy. In some embodiments, the individual exhibits a less desirable degree of responsiveness. In some embodiments, the individual exhibits enhanced responsiveness. In some embodiments, the individual has recurrent pancreatic cancer, i.e., the individual is initially responsive to the treatment with the prior therapy, but develops pancreatic cancer after about any of about 2, 3, 4, 5, 6, 7, 8, 9, 10, 11, 12, 24, or 36 months upon the cessation of the prior therapy.

In some embodiments, the prior therapy has stopped (for example for at least 1, 2, 3, 4, 5, 6, 7, 8, 9, or 10 months) when initiating the methods of the present invention. In some embodiments, the prior therapy has not stopped when initiating the methods of the present invention.

In some embodiments, the method further comprises a step of selecting patients for treatment. For example, in some embodiments, there is provided a method of treating pancreatic cancer in an individual who has been treated with a prior therapy, the method comprising: a) determining whether the individual has progressed on the prior therapy (such as gemcitabine-based therapy), and b) administering an effective amount of a composition comprising nanoparticles comprising albumin and a taxane to the individual. In some embodiments, there is provided a method of treating pancreatic cancer in an individual who has been treated with a prior therapy, the method comprising: a) selecting the individual who is not responsive to the prior therapy (such as gemcitabine-based therapy), and b) administering an effective amount of a composition comprising nanoparticles comprising albumin and a taxane to the individual. In some embodiments, there is provided a method of treating pancreatic cancer in an individual who has been treated with a prior therapy (such as gemcitabine-based therapy), the method comprising administering an effective amount of a composition comprising nanoparticles comprising albumin and a taxane to the individual, wherein said individual is selected for treatment based on the determination that the individual has progressed on the prior therapy. In some embodiments, there is provided a method of treating pancreatic cancer in an individual who has been treated with a prior therapy (such as gemcitabine-based therapy), the method comprising administering an effective amount of a composition comprising nanoparticles comprising albumin and a taxane to the individual, wherein said individual is selected on the basis of the non-responsiveness to the prior therapy.

In some embodiments, there is provided a method of treating pancreatic cancer in an individual who has been treated with a prior therapy (such as gemcitabine-based therapy), the method comprising: a) determining whether the individual is suitable for continued treatment with the prior therapy (for example due to lack of responsiveness and/or toxicity); and b) administering an effective amount of a composition comprising nanoparticles comprising albumin and a taxane to the individual. In some embodiments, there is provided a method of treating pancreatic cancer in an individual who has been treated with a prior therapy (such as gemcitabine-based therapy), the method comprising administering an effective amount of a composition comprising nanoparticles comprising albumin and a taxane to the individual, wherein said individual is selected based on the determination that the individual is unsuitable for continued treatment with the prior therapy (for example due to lack of responsiveness and/or toxicity). An individual can also be unsuitable for continued treatment with the prior therapy if the individual exhibits a less than desirable responsiveness or exhibits undesirable symptoms associated with the prior therapy.

In some embodiments, there is provided a method of treating pancreatic cancer in an individual who has been treated with a prior therapy, the method comprising: a) determining whether the individual is resistant or refractory to the prior therapy (such as gemcitabine-based therapy); and b) administering an effective amount of a composition comprising nanoparticles comprising albumin and a taxane to the individual. In some embodiments, there is provided a method of treating pancreatic cancer in an individual who has been treated with a prior therapy, the method comprising administering an effective amount of a composition comprising nanoparticles comprising albumin and a taxane to the individual, wherein said individual is selected based on the determination that the individual is resistant or refractory to the prior therapy (such as gemcitabine-based therapy). In some embodiments, the method does not comprise administration of an inhibitor of the hedgehog signaling pathway (a hedgehog inhibitor).

In some embodiments, the prior therapy comprises administration of gemcitabine ("gemcitabine-based therapy"). In some embodiments, the prior therapy is gemcitabine monotherapy. In some embodiments, the prior therapy comprises the administration of gemcitabine and erlotinib. In some embodiments, the prior therapy comprises the administration of gemcitabine and capecitabine. In some embodiments, the prior therapy comprises the administration of gemcitabine and 5-FU. In some embodiments, the prior therapy comprises the administration of gemcitabine, erlotinib, capecitabine, and/or 5-FU. In some embodiments, the prior therapy is adjuvant gemcitabine therapy. In some embodiments, the prior therapy is neoadjuvant gemcitabine therapy. In some embodiments, the prior therapy comprises surgery.

In some embodiments, the method described herein comprises administering taxane nanoparticle composition in conjunction with one or more of the same agent(s) used in the prior therapy. In some embodiments, the method described herein comprises administering taxane nanoparticle composition in conjunction with the agent(s) that is not used in the prior therapy.

In some embodiments, the method comprises administering to the individual an effective amount of a composition comprising nanoparticles comprising a taxane and an albumin, wherein the taxane in the nanoparticles is coated with the albumin, wherein the individual has progressed on a prior therapy (for example progressed after any of about 3, 6, 9, or 12 months upon initiation of the prior therapy). In some embodiments, the prior therapy is gemcitabine-based therapy, erlotinib-based therapy, or 5-FU-based therapy. In some embodiments, the method does not comprise administering gemcitabine. In some embodiments, the method comprises administering gemcitabine in conjunction with the nanoparticle composition. In some embodiments, the method does not comprise the administration of a platinum based agent (such as carboplatin or cisplatin). In some embodiments, the taxane is paclitaxel. In some embodiments, the albumin is human serum albumin. In some embodiments, the nanoparticles comprise paclitaxel coated with albumin. In some embodiments, the average particle size of the nanoparticles in the nanoparticle composition is no more than about 200 nm (such as less than about 200 nm). In some embodiments, the composition comprises the albumin stabilized nanoparticle formulation of paclitaxel (Nab-paclitaxel (ABRAXANE®)). In some embodiments, the composition is Nab-paclitaxel (ABRAXANE®). In some embodiments, the individual has non-metastatic pancreatic cancer. In some embodiments, the individual has primary pancreatic cancer.

In some embodiments, the method comprises administering to the individual an effective amount of a composition comprising nanoparticles comprising a taxane and an albumin, wherein the taxane in the nanoparticles is coated with the albumin, and wherein the individual is resistant or refractory to a prior therapy. In some embodiments, the prior therapy is gemcitabine-based therapy, erlotinib-based therapy, or 5-FU-based therapy. In some embodiments, the method does not comprise administering gemcitabine. In some embodiments, the method comprises administering gemcitabine in conjunction with the nanoparticle composition. In some embodiments, the method does not comprise the administration of a platinum-based agent (such as carboplatin or cisplatin). In some embodiments, the taxane is paclitaxel. In some embodiments, the albumin is human serum albumin. In some embodiments, the nanoparticles comprise paclitaxel coated with albumin. In some embodiments, the average particle size of the nanoparticles in the nanoparticle composition is no more than about 200 nm (such as less than about 200 nm). In some embodiments, the composition comprises the albumin stabilized nanoparticle formulation of paclitaxel (Nab-paclitaxel (ABRAXANE®)). In some embodiments, the composition is Nab-paclitaxel (ABRAXANE®). In some embodiments, the individual has non-metastatic pancreatic cancer. In some embodiments, the individual has primary pancreatic cancer.

In some embodiments, the method comprises administering to the individual an effective amount of a composition comprising nanoparticles comprising a taxane and an albumin, wherein the taxane in the nanoparticles is coated with the albumin, and wherein the individual has failed to respond to a prior therapy. In some embodiments, the prior therapy is gemcitabine-based therapy, erlotinib-based therapy, or 5-FU-based therapy. In some embodiments, the method does not comprise administering gemcitabine. In some embodiments, the method comprises administering gemcitabine in conjunction with the nanoparticle composition. In some embodiments, the method does not comprise the administration of a platinum-based agent (such as carboplatin or cisplatin). In some embodiments, the taxane is paclitaxel. In some embodiments, the albumin is human serum albumin. In some embodiments, the nanoparticles comprise paclitaxel coated with albumin. In some embodiments, the average particle size of the nanoparticles in the nanoparticle composition is no more than about 200 nm (such as less than about 200 nm). In some embodiments, the composition comprises the albumin stabilized nanoparticle formulation of paclitaxel (Nab-paclitaxel (ABRAXANE®)). In some embodiments, the composition is Nab-paclitaxel (ABRAXANE®). In some embodiments, the individual has non-metastatic pancreatic cancer. In some embodiments, the individual has primary pancreatic cancer.

In some embodiments, the method comprises administering to the individual an effective amount of a composition comprising nanoparticles comprising a taxane and an albumin, wherein the taxane in the nanoparticles is coated with the albumin, and wherein the individual exhibits a less desirable degree of responsiveness to a prior therapy. In some embodiments, the prior therapy is gemcitabine-based therapy, erlotinib-based therapy, or 5-FU-based therapy. In some embodiments, the method does not comprise administering gemcitabine. In some embodiments, the method comprises administering gemcitabine in conjunction with the nanoparticle composition. In some embodiments, the method does not comprise the administration of a platinum-based agent (such as carboplatin or cisplatin). In some embodiments, the taxane is paclitaxel. In some embodiments, the albumin is human serum albumin. In some embodiments, the nanoparticles comprise paclitaxel coated with albumin. In some embodiments, the average particle size of the nanoparticles in the nanoparticle composition is no more than about 200 nm (such as less than about 200 nm). In some embodiments, the composition comprises the albumin stabilized nanoparticle formulation of paclitaxel (Nab-paclitaxel (ABRAXANE®)). In some embodiments, the composition is Nab-paclitaxel (ABRAXANE®). In some embodiments, the individual has non-metastatic pancreatic cancer. In some embodiments, the individual has primary pancreatic cancer.

In some embodiments, the method comprises administering to the individual an effective amount of a composition comprising nanoparticles comprising a taxane and an albumin, wherein the taxane in the nanoparticles is coated with the albumin, and wherein the individual has recurrent pancreatic cancer (for example, the individual develops pancreatic cancer after about any of about 2, 3, 4, 5, 6, 7, 8, 9, 10, 11, 12, 24, or 36 months upon the cessation of a prior therapy). In some embodiments, the prior therapy is gemcitabine-based therapy, erlotinib-based therapy, or 5-FU-based therapy. In some embodiments, the method does not comprise administering gemcitabine. In some embodiments, the method comprises administering gemcitabine in conjunction with the nanoparticle composition. In some embodiments, the method does not comprise the administration of a platinum-based agent (such as carboplatin or cisplatin). In some embodiments, the taxane is paclitaxel. In some embodiments, the albumin is human serum albumin. In some embodiments, the nanoparticles comprise paclitaxel coated with albumin. In some embodiments, the average particle size of the nanoparticles in the nanoparticle composition is no more than about 200 nm (such as less than about 200 nm). In some embodiments, the composition comprises the albumin stabilized nanoparticle formulation of paclitaxel (Nab-paclitaxel (ABRAXANE®)). In some embodiments, the composition is Nab-paclitaxel (ABRAXANE®). In some embodiments, the individual has non-metastatic pancreatic cancer. In some embodiments, the individual has primary pancreatic cancer.

In some embodiments, the method comprises administering to the individual an effective amount of a composition comprising nanoparticles comprising a taxane and an albumin, wherein the taxane in the nanoparticles is coated with the albumin, and wherein a prior therapy has stopped (for example, for at least 1, 2, 3, 4, 5, 6, 7, 8, 9, or 10 months) when initiating the administration of the effective amount of the composition comprising nanoparticles comprising a taxane and an albumin to the individual. In some embodiments, the prior therapy is gemcitabine-based therapy, erlotinib-based therapy, or 5-FU-based therapy. In some embodiments, the method does not comprise administering gemcitabine. In some embodiments, the method comprises administering gemcitabine in conjunction with the nanoparticle composition. In some embodiments, the method does not comprise the administration of a platinum-based agent (such as carboplatin or cisplatin). In some embodiments, the taxane is paclitaxel. In some embodiments, the albumin is human serum albumin. In some embodiments, the nanoparticles comprise paclitaxel coated with albumin. In some embodiments, the average particle size of the nanoparticles in the nanoparticle composition is no more than about 200 nm (such as less than about 200 nm). In some embodiments, the composition comprises the albumin stabilized nanoparticle formulation of paclitaxel (Nab-paclitaxel (ABRAXANE®)). In some embodiments, the composition is Nab-paclitaxel (ABRAXANE®). In some embodiments, the individual has non-metastatic pancreatic cancer. In some embodiments, the individual has primary pancreatic cancer.

In some embodiments, the method comprises administering to the individual an effective amount of a composition comprising nanoparticles comprising a taxane and an albumin, wherein the taxane is coated with the albumin, wherein the individual has progressed on a prior therapy (such as gemcitabine-based therapy). In some embodiments, there is provided a method of treating pancreatic cancer in an individual in need thereof, comprising administering to the individual an effective amount of a composition comprising nanoparticles comprising a taxane and an albumin, wherein the average particle size of the nanoparticles in the nanoparticle composition is no greater than about 200 nm (such as less than about 200 nm), wherein the individual has progressed on a gemcitabine-based therapy. In some embodiments, there is provided a method of treating pancreatic cancer in an individual in need thereof, comprising administering to the individual an effective amount of a composition comprising nanoparticles comprising a taxane and an albumin, wherein the taxane is coated with the albumin, wherein the average particle size of the nanoparticles in the nanoparticle composition is no greater than about 200 nm (such as less than about 200 nm), wherein the individual has progressed on gemcitabine-based therapy. In some embodiments, there is provided a method of treating pancreatic cancer in an individual in need thereof, comprising administering to the individual an effective amount of a composition comprising Nab-paclitaxel, wherein the individual has progressed on gemcitabine-based therapy. In some embodiments, there is provided a method of treating pancreatic cancer in an individual in need thereof, comprising administering to the individual an effective amount of Nab-paclitaxel, wherein the individual has progressed on gemcitabine-based therapy. In some embodiments, the method does not comprise administering gemcitabine. In some embodiments, the method comprises administering gemcitabine in conjunction with the nanoparticle composition. In some embodiments, the method does not comprise the administration of a platinum-based agent (such as carboplatin or cisplatin). In some embodiments, the method does not comprise administration of an inhibitor of the hedgehog signaling pathway (a hedgehog inhibitor). In some embodiments, the individual has non-metastatic pancreatic cancer. In some embodiments, the individual has primary pancreatic cancer.

In some embodiments, the method comprises administering to the individual an effective amount of a composition comprising nanoparticles comprising a taxane and an albumin, wherein the taxane is coated with the albumin, and wherein the individual is resistant or refractory to a prior therapy (such as gemcitabine-based therapy). In some embodiments, there is provided a method of treating pancreatic cancer in an individual in need thereof, comprising administering to the individual an effective amount of a composition comprising nanoparticles comprising a taxane and an albumin, wherein the average particle size of the nanoparticles in the nanoparticle composition is no greater than about 200 nm (such as less than about 200 nm), wherein the individual is resistant or refractory to a prior therapy (such as gemcitabine-based therapy). In some embodiments, there is provided a method of treating pancreatic cancer in an individual in need thereof, comprising administering to the individual an effective amount of a composition comprising nanoparticles comprising a taxane and an albumin, wherein the taxane is coated with the albumin, wherein the average particle size of the nanoparticles in the nanoparticle composition is no greater than about 200 nm (such as less than about 200 nm), wherein the individual is resistant or refractory to a prior therapy (such as gemcitabine-based therapy). In some embodiments, there is provided a method of treating pancreatic cancer in an individual in need thereof, comprising administering to the individual an effective amount of a composition comprising Nab-paclitaxel, wherein the individual is resistant or refractory to a prior therapy (such as gemcitabine-based therapy). In some embodiments, there is provided a method of treating pancreatic cancer in an individual in need thereof, comprising administering to the individual an effective amount of Nab-paclitaxel, wherein the individual is resistant or refractory to a prior therapy (such as gemcitabine-based therapy). In some embodiments, the method does not comprise administering gemcitabine. In some embodiments, the method comprises administering gemcitabine in conjunction with the nanoparticle composition. In some embodiments, the method does not comprise the administration of a platinum-based agent (such as carboplatin or cisplatin). In some embodiments, the method does not comprise administration of an inhibitor of the hedgehog signaling pathway (a hedgehog inhibitor). In some embodiments, the individual has non-metastatic pancreatic cancer. In some embodiments, the individual has primary pancreatic cancer.

In some embodiments, the method comprises administering to the individual an effective amount of a composition comprising nanoparticles comprising a taxane and an albumin, wherein the taxane is coated with the albumin, and wherein the individual has failed to respond to a prior therapy (such as gemcitabine-based therapy). In some embodiments, there is provided a method of treating pancreatic cancer in an individual in need thereof, comprising administering to the individual an effective amount of a composition comprising nanoparticles comprising a taxane and an albumin, wherein the average particle size of the nanoparticles in the nanoparticle composition is no greater than about 200 nm (such as less than about 200 nm), wherein the individual has failed to respond to a prior therapy (such as gemcitabine-based therapy). In some embodiments, there is provided a method of treating pancreatic cancer in an individual in need thereof, comprising administering to the individual an effective amount of a composition comprising nanoparticles comprising a taxane and an albumin, wherein the taxane is coated with the albumin, wherein the average particle size of the nanoparticles in the nanoparticle composition is no greater than about 200 nm (such as less than about 200 nm), wherein the individual has failed to respond to a prior therapy (such as gemcitabine-based therapy). In some embodiments, there is provided a method of treating pancreatic cancer in an individual in need thereof, comprising administering to the individual an effective amount of a composition comprising Nab-paclitaxel, wherein the individual has failed to respond to a prior therapy (such as gemcitabine-based therapy). In some embodiments, there is provided a method of treating pancreatic cancer in an individual in need thereof, comprising administering to the individual an effective amount of Nab-paclitaxel, wherein the individual has failed to respond to a prior therapy (such as gemcitabine-based therapy). In some embodiments, the method does not comprise administering gemcitabine. In some embodiments, the method comprises administering gemcitabine in conjunction with the nanoparticle composition. In some embodiments, the method does not comprise the administration of a platinum-based agent (such as carboplatin or cisplatin). In some embodiments, the method does not comprise administration of an inhibitor of the hedgehog signaling pathway (a hedgehog inhibitor). In some embodiments, the individual has non-metastatic pancreatic cancer. In some embodiments, the individual has primary pancreatic cancer.

In some embodiments, the method comprises administering to the individual an effective amount of a composition comprising nanoparticles comprising a taxane and an albumin, wherein the taxane is coated with the albumin, and wherein the individual exhibits a less desirable degree of responsiveness to a prior therapy (such as a gemcitabine-based therapy). In some embodiments, there is provided a method of treating pancreatic cancer in an individual in need thereof, comprising administering to the individual an effective amount of a composition comprising nanoparticles comprising a taxane and an albumin, wherein the average particle size of the nanoparticles in the nanoparticle composition is no greater than about 200 nm (such as less than about 200 nm), wherein the individual exhibits a less desirable degree of responsiveness to a prior therapy (such as a gemcitabine-based therapy). In some embodiments, there is provided a method of treating pancreatic cancer in an individual in need thereof, comprising administering to the individual an effective amount of a composition comprising nanoparticles comprising a taxane and an albumin, wherein the taxane is coated with the albumin, wherein the average particle size of the nanoparticles in the nanoparticle composition is no greater than about 200 nm (such as less than about 200 nm), wherein the individual exhibits a less desirable degree of responsiveness to a prior therapy (such as a gemcitabine-based therapy). In some embodiments, there is provided a method of treating pancreatic cancer in an individual in need thereof, comprising administering to the individual an effective amount of a composition comprising Nab-paclitaxel, wherein the individual exhibits a less desirable degree of responsiveness to a prior therapy (such as a gemcitabine-based therapy). In some embodiments, there is provided a method of treating pancreatic cancer in an individual in need thereof, comprising administering to the individual an effective amount of Nab-paclitaxel, wherein the individual exhibits a less desirable degree of responsiveness to a prior therapy (such as a gemcitabine-based therapy). In some embodiments, the method does not comprise administering gemcitabine. In some embodiments, the method comprises administering gemcitabine in conjunction with the nanoparticle composition. In some embodiments, the method does not comprise the administration of a platinum-based agent (such as carboplatin or cisplatin). In some embodiments, the method does not comprise administration of an inhibitor of the hedgehog signaling pathway (a hedgehog inhibitor). In some embodiments, the individual has non-metastatic pancreatic cancer. In some embodiments, the individual has primary pancreatic cancer.

In some embodiments, the method comprises administering to the individual an effective amount of a composition comprising nanoparticles comprising a taxane and an albumin, wherein the taxane is coated with the albumin, and wherein the individual has recurrent pancreatic cancer (for example, the individual develops pancreatic cancer after about any of about 2, 3, 4, 5, 6, 7, 8, 9, 10, 11, 12, 24, or 36 months upon the cessation of a gemcitabine-based therapy). In some embodiments, there is provided a method of treating pancreatic cancer in an individual in need thereof, comprising administering to the individual an effective amount of a composition comprising nanoparticles comprising a taxane and an albumin, wherein the average particle size of the nanoparticles in the nanoparticle composition is no greater than about 200 nm (such as less than about 200 nm), wherein the individual has recurrent pancreatic cancer (for example, the individual develops pancreatic cancer after about any of about 2, 3, 4, 5, 6, 7, 8, 9, 10, 11, 12, 24, or 36 months upon the cessation of a gemcitabine-based therapy). In some embodiments, there is provided a method of treating pancreatic cancer in an individual in need thereof, comprising administering to the individual an effective amount of a composition comprising nanoparticles comprising a taxane and an albumin, wherein the taxane is coated with the albumin, wherein the average particle size of the nanoparticles in the nanoparticle composition is no greater than about 200 nm (such as less than about 200 nm), wherein the individual has recurrent pancreatic cancer (for example, the individual develops pancreatic cancer after about any of about 2, 3, 4, 5, 6, 7, 8, 9, 10, 11, 12, 24, or 36 months upon the cessation of a gemcitabine-based therapy). In some embodiments, there is provided a method of treating pancreatic cancer in an individual in need thereof, comprising administering to the individual an effective amount of a composition comprising Nab-paclitaxel, wherein the individual has recurrent pancreatic cancer (for example, the individual develops pancreatic cancer after about any of about 2, 3, 4, 5, 6, 7, 8, 9, 10, 11, 12, 24, or 36 months upon the cessation of a gemcitabine-based therapy). In some embodiments, there is provided a method of treating pancreatic cancer in an individual in need thereof, comprising administering to the individual an effective amount of Nab-paclitaxel, wherein the individual has recurrent pancreatic cancer (for example, the individual develops pancreatic cancer after about any of about 2, 3, 4, 5, 6, 7, 8, 9, 10, 11, 12, 24, or 36 months upon the cessation of a gemcitabine-based therapy). In some embodiments, the method comprises administering gemcitabine in conjunction with the nanoparticle composition. In some embodiments, the method does not comprise the administration of a platinum-based agent (such as carboplatin or cisplatin). In some embodiments, the method does not comprise administration of an inhibitor of the hedgehog signaling pathway (a hedgehog inhibitor). In some embodiments, the individual has non-metastatic pancreatic cancer. In some embodiments, the individual has primary pancreatic cancer.

In some embodiments, the method comprises administering to the individual an effective amount of a composition comprising nanoparticles comprising a taxane and an albumin, wherein the taxane is coated with the albumin, and wherein a prior therapy (such as a gemcitabine-based therapy) has stopped (for example, for at least 1, 2, 3, 4, 5, 6, 7, 8, 9, or 10 months) when initiating the administration of the effective amount of the composition comprising nanoparticles comprising a taxane and an albumin to the individual. In some embodiments, there is provided a method of treating pancreatic cancer in an individual in need thereof, comprising administering to the individual an effective amount of a composition comprising nanoparticles comprising a taxane and an albumin, wherein the average particle size of the nanoparticles in the nanoparticle composition is no greater than about 200 nm (such as less than about 200 nm), wherein a prior therapy (such as a gemcitabine-based therapy) has stopped (for example, for at least 1, 2, 3, 4, 5, 6, 7, 8, 9, or 10 months) when initiating the administration of the effective amount of the composition comprising nanoparticles comprising a taxane and an albumin to the individual. In some embodiments, there is provided a method of treating pancreatic cancer in an individual in need thereof, comprising administering to the individual an effective amount of a composition comprising nanoparticles comprising a taxane and an albumin, wherein the taxane is coated with the albumin, wherein the average particle size of the nanoparticles in the nanoparticle composition is no greater than about 200 nm (such as less than about 200 nm), wherein a prior therapy (such as a gemcitabine-based therapy) has stopped (for example, for at least 1, 2, 3, 4, 5, 6, 7, 8, 9, or 10 months) when initiating the administration of the effective amount of the composition comprising nanoparticles comprising a taxane and an albumin to the individual. In some embodiments, there is provided a method of treating pancreatic cancer in an individual in need thereof, comprising administering to the individual an effective amount of a composition comprising Nab-paclitaxel, wherein a prior therapy (such as a gemcitabine-based therapy) has stopped (for example, for at least 1, 2, 3, 4, 5, 6, 7, 8, 9, or 10 months) when initiating the administration of the effective amount of the composition comprising nanoparticles comprising a taxane and an albumin to the individual. In some embodiments, there is provided a method of treating pancreatic cancer in an individual in need thereof, comprising administering to the individual an effective amount of Nab-paclitaxel, wherein a prior therapy (such as a gemcitabine-based therapy) has stopped (for example, for at least 1, 2, 3, 4, 5, 6, 7, 8, 9, or 10 months) when initiating the administration of the effective amount of the composition comprising nanoparticles comprising a taxane and an albumin to the individual. In some embodiments, the method does not comprise administering gemcitabine. In some embodiments, the method comprises administering gemcitabine in conjunction with the nanoparticle composition. In some embodiments, the method does not comprise the administration of a platinum-based agent (such as carboplatin or cisplatin). In some embodiments, the method does not comprise administration of an inhibitor of the hedgehog signaling pathway (a hedgehog inhibitor). In some embodiments, the individual has non-metastatic pancreatic cancer. In some embodiments, the individual has primary pancreatic cancer.

In some embodiments, levels of serum CA 19-9 in the individual administered with the composition of the present invention decrease significantly. In some embodiments, the levels of serum CA 19-9 in the individual administered with the composition comprising nanoparticles comprising a taxane and an albumin are decreased by at least about 20% (including for example at least about any of 20%, 30%, 40%, 50%, 52%, 53%, 55%, 57%, 59%, 60%, 70%, 80%, 90%, 95%, or 100%) in comparison to the levels of serum CA 19-9 prior to the treatment. In some embodiments, the levels of serum CA 19-9 in the individual administered with the composition comprising nanoparticles comprising a taxane and an albumin are decreased by at least about 50% in comparison to the levels of serum CA 19-9 prior to the treatment.

In some embodiments, the method is for treating an individual having locally advanced, unresectable, or metastatic pancreatic ductal carcinoma, wherein the individual has progressed within 6 months (such as within any of about 5, 4, 3, 2, 1 month) of gemcitabine-based therapy, comprising administering (such as administering intravenously) to the individual an effective amount of a composition comprising nanoparticles comprising albumin and a taxane (such as nanoparticles comprising albumin and paclitaxel, for example ABRAXANE®). In some embodiments, the nanoparticle composition is administered weekly at the dose of 100 mg/m$^2$. In some embodiments, the administration is carried out three out of four weeks.

In some embodiments, the pancreatic cancer is exocrine pancreatic cancer or endocrine pancreatic cancer. The exocrine pancreatic cancer includes, but is not limited to, adenocarcinomas, acinar cell carcinomas, adenosquamous carcinomas, colloid carcinomas, undifferentiated carcinomas with osteoclast-like giant cells, hepatoid carcinomas, intraductal papillary-mucinous neoplasms, mucinous cystic neoplasms, pancreatoblastomas, serous cystadenomas, signet ring cell carcinomas, solid and pseuodpapillary tumors, pancreatic ductal carcinomas, and undifferentiated carcinomas. In some embodiments, the exocrine pancreatic cancer is pancreatic ductal carcinoma.

The endocrine pancreatic cancer includes, but is not limited to, insulinomas and glucagonomas.

In some embodiments, the pancreatic cancer is early stage pancreatic cancer, non-metastatic pancreatic cancer, primary pancreatic cancer, advanced pancreatic cancer, locally advanced pancreatic cancer, metastatic pancreatic cancer, unresectable pancreatic cancer, pancreatic cancer in remission, or recurrent pancreatic cancer. In some embodiments, the pancreatic cancer is locally advanced pancreatic cancer, unresectable pancreatic cancer, or metastatic pancreatic ductal carcinoma. In some embodiments, the pancreatic cancer is resistant to the gemcitabine-based therapy. In some embodiments, the pancreatic cancer is refractory to the gemcitabine-based therapy. In some embodiments, the pancreatic cancer is resectable (i.e., tumors that are confined to a portion of the pancreas or has spread just beyond it that allows for complete surgical removal), or locally advanced (unresectable) (i.e., the localized tumors may be unresectable because of local vessel impingement or invasion by tumor). In some embodiments, the pancreatic cancer is, according to American Joint Committee on Cancer (AJCC) TNM classifications, a stage 0 tumor (the tumor is confined to the top layers of pancreatic duct cells and has not invaded deeper tissues, and it has not spread outside of the pancreas (e.g., pancreatic carcinoma in situ or pancreatic intraepithelial neoplasia III), a stage IA tumor (the tumor is confined to the pancreas and is less than 2 cm in size, and it has not spread to nearby lymph nodes or distinct sites), a stage IB tumor (the tumor is confined to the pancreas and is larger than 2 cm in size, and it has not spread to nearby lymph nodes or distant sites), a stage IIA tumor (the tumor is growing outside the pancreas but not into large blood vessels, and it has not spread to nearby lymph nodes or distant sites), stage IIB (the tumor is either confined to the pancreas or growing outside the pancreas but not into nearby large blood vessels or major nerves, and it has spread to nearby lymph nodes but not distant sites), stage III (the tumor is growing outside the pancreas into nearby large blood vessels or major nerves, and it may or may not have spread to nearby lymph nodes. It has not spread to distant sites) or stage IV tumor (the cancer has spread to distant sites).

The methods provided herein can be used to treat an individual (e.g., human) who has been diagnosed with pancreatic cancer and has progressed on a prior therapy (e.g., gemcitabine-based, erlotinib-based, or 5-fluorouracil-based therapy). In some embodiments, the individual is resistant to treatment of pancreatic cancer with gemcitabine-based therapy (e.g., gemcitabine monotherapy or gemcitabine combination therapy) and has progressed after treatment (e.g., the pancreatic cancer has been refractory). In some embodiments, the individual is initially responsive to treatment of pancreatic cancer with gemcitabine-based therapy (e.g., gemcitabine monotherapy or gemcitabine combination therapy) but has progressed after treatment. In some embodiments, the individual is human. In some embodiments, the individual is at least about any of 30, 35, 40, 45, 50, 55, 60, 65, 70, 75, 80, or 85 years old. In some embodiments, the individual has a family history of pancreatic cancer (e.g., at least 2 first-degree relatives affected with pancreatic cancer without accumulation of other cancers or familial diseases). In some embodiments, the individual has one or more hereditary pancreatic cancer syndromes, including, but not limited to, BRCA2 mutation, familial atypical multiple mole melanoma (FAMMM), peutz-jeghers syndrome, and hereditary pancreatitis. In some embodiments, the individual is a long-time smoker (e.g., more than 10, 15, or 20 years). In some embodiments, the patient has adult-onset diabetes. In some embodiments, the individual is a male. In some embodiments, the individual is a female. In some embodiments, the individual has early stage of pancreatic cancer, non-metastatic pancreatic cancer, primary pancreatic cancer, resected pancreatic cancer, advanced pancreatic cancer, locally advanced pancreatic cancer, metastatic pancreatic cancer, unresectable pancreatic cancer, pancreatic cancer in remission, or recurrent pancreatic cancer. In some embodiments, the individual has Stage 0, IA, IB, IIA, IIB, III, or IV pancreatic cancer according to AJCC (American Joint Commission on Cancer) TNM staging criteria. In some embodiments, the individual has ECOG/WHO/Zubrod score of 0 (asymptomatic), 1 (symptomatic but completely ambulatory), 2 (symptomatic, <50% in bed during the day), 3 (symptomatic, >50% in bed, but not bedbound), or 4 (bedbound). In some embodiments, the individual has a single lesion at presentation. In some embodiments, the individual has multiple lesions at presentation.

In some embodiments, the individual is a human who exhibits one or more symptoms associated with pancreatic cancer. In some embodiments, the individual is at an early stage of pancreatic cancer. In some embodiments, the individual is at an advanced stage of pancreatic cancer. In some embodiments, the individual has non-metastatic pancreatic cancer. In some embodiments, the individual has primary pancreatic cancer. In some of embodiments, the individual is genetically or otherwise predisposed (e.g., having a risk factor) to developing pancreatic cancer. These risk factors include, but are not limited to, age, sex, race, diet, history of previous pancreatic cancer, presence of hereditary pancreatic cancer syndrome (e.g., BRCA2 mutation, familial atypical multiple mole melanoma, Peutz-Jeghers Syndrome, hereditary pancreatitis), genetic (e.g., familial pancreatic cancer) considerations, and environmental exposure. In some embodiments, the individuals at risk for pancreatic cancer include, e.g., those having at least 2 first-degree relatives who have experienced pancreatic cancer without accumulation of other cancers or familial diseases, and those whose risk is determined by analysis of genetic or biochemical markers (e.g., BRCA2, p16, STK11/LKB1, or PRSS1 gene). In some embodiments, the individual is positive for SPARC expression (for example based on IHC standard). In some embodiments, the individual is negative for SPARC expression.

The methods provided herein may be practiced in an adjuvant setting. In some embodiments, the method is practiced in a neoadjuvant setting, i.e., the method may be carried out before the primary/definitive therapy.

The methods described herein are useful for various aspects of pancreatic cancer treatment. In some embodiments, there is provided a method of inhibiting pancreatic cancer cell proliferation (such as pancreatic cancer tumor growth) in an individual, comprising administering to the individual an effective amount of a composition comprising nanoparticles comprising a taxane and an albumin, wherein the individual has progressed on gemcitabine-based therapy. In some embodiments, at least about 10% (including for example at least about any of 20%, 30%, 40%, 60%, 70%, 80%, 90%, or 100%) cell proliferation is inhibited. In some embodiments, the taxane is paclitaxel. In some embodiments, the taxane in the nanoparticle in the composition is administered by intravenous administration.

In some embodiments, there is provided a method of inhibiting pancreatic cancer tumor metastasis in an individual, comprising administering to the individual an effective amount of a composition comprising nanoparticles comprising a taxane and an albumin, wherein the individual has progressed on gemcitabine-based therapy. In some embodiments, at least about 10% (including for example at least about any of 20%, 30%, 40%, 60%, 70%, 80%, 90%, or 100%) metastasis is inhibited. In some embodiments, a method of inhibiting metastasis to one or more lymph nodes is provided. In some embodiments, the taxane is paclitaxel. In some embodiments, the taxane in the nanoparticle in the composition is administered by intravenous administration.

In some embodiments, there is provided a method of inhibiting pancreatic cancer tumor metastasis in an individual, comprising administering to the individual an effective amount of a composition comprising nanoparticles comprising a taxane and an albumin, and wherein the individual is resistant or refractory to a gemcitabine-based therapy. In some embodiments, at least about 10% (including for example at least about any of 20%, 30%, 40%, 60%, 70%, 80%, 90%, or 100%) metastasis is inhibited. In some embodiments, a method of inhibiting metastasis to one or more lymph nodes is provided. In some embodiments, the taxane is paclitaxel. In some embodiments, the taxane in the nanoparticle in the composition is administered by intravenous administration.

In some embodiments, there is provided a method of inhibiting pancreatic cancer tumor metastasis in an individual, comprising administering to the individual an effective amount of a composition comprising nanoparticles comprising a taxane and an albumin, and wherein the individual has failed to respond to a gemcitabine-based therapy. In some embodiments, at least about 10% (including for example at least about any of 20%, 30%, 40%, 60%, 70%, 80%, 90%, or 100%) metastasis is inhibited. In some embodiments, a method of inhibiting metastasis to one or more lymph nodes is provided. In some embodiments, the taxane is paclitaxel. In some embodiments, the taxane in the nanoparticle in the composition is administered by intravenous administration.

In some embodiments, there is provided a method of inhibiting pancreatic cancer tumor metastasis in an individual, comprising administering to the individual an effective amount of a composition comprising nanoparticles comprising a taxane and an albumin, and wherein the individual exhibits a less desirable degree of responsiveness to a gemcitabine-based therapy. In some embodiments, at least about 10% (including for example at least about any of 20%, 30%, 40%, 60%, 70%, 80%, 90%, or 100%) metastasis is inhibited. In some embodiments, a method of inhibiting metastasis to one or more lymph nodes is provided. In some embodiments, the taxane is paclitaxel. In some embodiments, the taxane in the nanoparticle in the composition is administered by intravenous administration.

In some embodiments, there is provided a method of inhibiting pancreatic cancer tumor metastasis in an individual, comprising administering to the individual an effective amount of a composition comprising nanoparticles comprising a taxane and an albumin, and wherein the individual has recurrent pancreatic cancer (for example, the individual develops pancreatic cancer after about any of about 2, 3, 4, 5, 6, 7, 8, 9, 10, 11, 12, 24, or 36 months upon the cessation of a gemcitabine-based therapy). In some embodiments, at least about 10% (including for example at least about any of 20%, 30%, 40%, 60%, 70%, 80%, 90%, or 100%) metastasis is inhibited. In some embodiments, a method of inhibiting metastasis to one or more lymph nodes is provided. In some embodiments, the taxane is paclitaxel. In some embodiments, the taxane in the nanoparticle in the composition is administered by intravenous administration.

In some embodiments, there is provided a method of inhibiting pancreatic cancer tumor metastasis in an individual, comprising administering to the individual an effective amount of a composition comprising nanoparticles comprising a taxane and an albumin, and wherein a gemcitabine-based therapy has stopped (for example, for at least 1, 2, 3, 4, 5, 6, 7, 8, 9, or 10 months) when initiating the administration of the effective amount of the composition comprising nanoparticles comprising a taxane and an albumin to the individual. In some embodiments, at least about 10% (including for example at least about any of 20%, 30%, 40%, 60%, 70%, 80%, 90%, or 100%) metastasis is inhibited. In some embodiments, a method of inhibiting metastasis to one or more lymph nodes is provided. In some embodiments, the taxane is paclitaxel. In some embodiments, the taxane in the nanoparticle in the composition is administered by intravenous administration.

In some embodiments, there is provided a method of reducing (such as eradiating) pre-existing pancreatic cancer tumor metastasis (such as metastasis to the lymph node) in an individual, comprising administering to the individual an effective amount of a composition comprising nanoparticles comprising a taxane and an albumin, wherein the individual has progressed on gemcitabine-based therapy. In some embodiments, at least about 10% (including for example at least about any of 20%, 30%, 40%, 60%, 70%, 80%, 90%, or 100%) metastasis is reduced. In some embodiments, method of reducing metastasis to lymph node is provided. In some embodiments, the taxane is paclitaxel. In some embodiments, the taxane in the nanoparticle in the composition is administered by intravenous administration.

In some embodiments, there is provided a method of reducing (such as eradiating) pre-existing pancreatic cancer tumor metastasis (such as metastasis to the lymph node) in an individual, comprising administering to the individual an effective amount of a composition comprising nanoparticles comprising a taxane and an albumin, and wherein the individual is resistant or refractory to a gemcitabine-based therapy. In some embodiments, at least about 10% (including for example at least about any of 20%, 30%, 40%, 60%, 70%, 80%, 90%, or 100%) metastasis is reduced. In some embodiments, method of reducing metastasis to lymph node is provided. In some embodiments, the taxane is paclitaxel. In some embodiments, the taxane in the nanoparticle in the composition is administered by intravenous administration.

In some embodiments, there is provided a method of reducing (such as eradiating) pre-existing pancreatic cancer tumor metastasis (such as metastasis to the lymph node) in an individual, comprising administering to the individual an effective amount of a composition comprising nanoparticles comprising a taxane and an albumin, and wherein the individual has failed to respond to a gemcitabine-based therapy. In some embodiments, at least about 10% (including for example at least about any of 20%, 30%, 40%, 60%, 70%, 80%, 90%, or 100%) metastasis is reduced. In some embodiments, method of reducing metastasis to lymph node is provided. In some embodiments, the taxane is paclitaxel. In some embodiments, the taxane in the nanoparticle in the composition is administered by intravenous administration.

In some embodiments, there is provided a method of reducing (such as eradiating) pre-existing pancreatic cancer tumor metastasis (such as metastasis to the lymph node) in an individual, comprising administering to the individual an effective amount of a composition comprising nanoparticles comprising a taxane and an albumin, and wherein the individual exhibits a less desirable degree of responsiveness to a gemcitabine-based therapy. In some embodiments, at least about 10% (including for example at least about any of 20%, 30%, 40%, 60%, 70%, 80%, 90%, or 100%) metastasis is reduced. In some embodiments, method of reducing metastasis to lymph node is provided. In some embodiments, the taxane is paclitaxel. In some embodiments, the taxane in the nanoparticle in the composition is administered by intravenous administration. In some embodiments, at least about 10% (including for example at least about any of 20%, 30%, 40%, 60%, 70%, 80%, 90%, or 100%) metastasis is reduced. In some embodiments, method of reducing metastasis to lymph node is provided. In some embodiments, the taxane is paclitaxel. In some embodiments, the taxane in the nanoparticle in the composition is administered by intravenous administration.

In some embodiments, there is provided a method of reducing (such as eradiating) pre-existing pancreatic cancer tumor metastasis (such as metastasis to the lymph node) in an individual, comprising administering to the individual an effective amount of a composition comprising nanoparticles comprising a taxane and an albumin, and wherein the individual has recurrent pancreatic cancer (for example, the individual develops pancreatic cancer after about any of about 2, 3, 4, 5, 6, 7, 8, 9, 10, 11, 12, 24, or 36 months upon the cessation of a gemcitabine-based therapy). In some embodiments, at least about 10% (including for example at least about any of 20%, 30%, 40%, 60%, 70%, 80%, 90%, or 100%) metastasis is reduced. In some embodiments, method of reducing metastasis to lymph node is provided. In some embodiments, the taxane is paclitaxel. In some embodiments, the taxane in the nanoparticle in the composition is administered by intravenous administration.

In some embodiments, there is provided a method of reducing (such as eradiating) pre-existing pancreatic cancer tumor metastasis (such as metastasis to the lymph node) in an individual, comprising administering to the individual an effective amount of a composition comprising nanoparticles comprising a taxane and an albumin, and wherein a gemcitabine-based therapy has stopped (for example for at least 1, 2, 3, 4, 5, 6, 7, 8, 9, or 10 months) when initiating the administration of the effective amount of the composition comprising nanoparticles comprising a taxane and an albumin to the individual. In some embodiments, at least about 10% (including for example at least about any of 20%, 30%, 40%, 60%, 70%, 80%, 90%, or 100%) metastasis is reduced. In some embodiments, method of reducing metastasis to lymph node is provided. In some embodiments, the taxane is paclitaxel. In some embodiments, the taxane in the nanoparticle in the composition is administered by intravenous administration.

In some embodiments, there is provided a method of reducing incidence or burden of preexisting pancreatic cancer tumor metastasis (such as metastasis to the lymph node) in an individual, comprising administering to the individual an effective amount of a composition comprising nanoparticles comprising a taxane and an albumin, wherein the individual has progressed on gemcitabine-based therapy. In some embodiments, the taxane is paclitaxel. In some embodiments, the taxane in the nanoparticle in the composition is administered by intravenous administration.

In some embodiments, there is provided a method of reducing incidence or burden of preexisting pancreatic cancer tumor metastasis (such as metastasis to the lymph node) in an individual, comprising administering to the individual an effective amount of a composition comprising nanoparticles comprising a taxane and an albumin, and wherein the individual is resistant or refractory to a gemcitabine-based therapy. In some embodiments, the taxane is paclitaxel. In some embodiments, the taxane in the nanoparticle in the composition is administered by intravenous administration.

In some embodiments, there is provided a method of reducing incidence or burden of preexisting pancreatic cancer tumor metastasis (such as metastasis to the lymph node) in an individual, comprising administering to the individual an effective amount of a composition comprising nanoparticles comprising a taxane and an albumin, and wherein the individual has failed to respond to a gemcitabine-based therapy. In some embodiments, the taxane is paclitaxel. In some embodiments, the taxane in the nanoparticle in the composition is administered by intravenous administration.

In some embodiments, there is provided a method of reducing incidence or burden of preexisting pancreatic cancer tumor metastasis (such as metastasis to the lymph node) in an individual, comprising administering to the individual an effective amount of a composition comprising nanoparticles comprising a taxane and an albumin, and wherein the individual exhibits a less desirable degree of responsiveness to a gemcitabine-based therapy. In some embodiments, the taxane is paclitaxel. In some embodiments, the taxane in the nanoparticle in the composition is administered by intravenous administration.

In some embodiments, there is provided a method of reducing incidence or burden of preexisting pancreatic cancer tumor metastasis (such as metastasis to the lymph node) in an individual, comprising administering to the individual an effective amount of a composition comprising nanoparticles comprising a taxane and an albumin, and wherein the individual has recurrent pancreatic cancer (for example, the individual develops pancreatic cancer after about any of about 2, 3, 4, 5, 6, 7, 8, 9, 10, 11, 12, 24, or 36 months upon the cessation of a gemcitabine-based therapy). In some embodiments, the taxane is paclitaxel. In some embodiments, the taxane in the nanoparticle in the composition is administered by intravenous administration.

In some embodiments, there is provided a method of reducing incidence or burden of preexisting pancreatic cancer tumor metastasis (such as metastasis to the lymph node) in an individual, comprising administering to the individual an effective amount of a composition comprising nanoparticles comprising a taxane and an albumin, and wherein a gemcitabine-based therapy has stopped (for example, for at least 1, 2, 3, 4, 5, 6, 7, 8, 9, or 10 months) when initiating the administration of the effective amount of the composition comprising nanoparticles comprising a taxane and an albumin to the individual. In some embodiments, the taxane in the nanoparticle in the composition is administered by intravenous administration.

In some embodiments, there is provided a method of reducing pancreatic cancer tumor size in an individual, comprising administering to the individual an effective amount of a composition comprising nanoparticles comprising a taxane and an albumin, wherein the individual has progressed on gemcitabine-based therapy. In some embodiments, the tumor size is reduced at least about 10% (including for example at least about any of 20%, 30%, 40%, 60%, 70%, 80%, 90%, or 100%). In some embodiments, the taxane is paclitaxel. In some embodiments, the taxane in the nanoparticle in the composition is administered by intravenous administration. In some embodiments, the individual has non-metastatic pancreatic cancer. In some embodiments, the individual has primary pancreatic cancer.

In some embodiments, there is provided a method of reducing pancreatic cancer tumor size in an individual, comprising administering to the individual an effective amount of a composition comprising nanoparticles comprising a taxane and an albumin, and wherein the individual is resistant or refractory to a gemcitabine-based therapy. In some embodiments, the tumor size is reduced at least about 10% (including for example at least about any of 20%, 30%, 40%, 60%, 70%, 80%, 90%, or 100%). In some embodiments, the taxane is paclitaxel. In some embodiments, the taxane in the nanoparticle in the composition is administered by intravenous administration. In some embodiments, the individual has non-metastatic pancreatic cancer. In some embodiments, the individual has primary pancreatic cancer.

In some embodiments, there is provided a method of reducing pancreatic cancer tumor size in an individual, comprising administering to the individual an effective amount of a composition comprising nanoparticles comprising a taxane and an albumin, and wherein the individual has failed to respond to a gemcitabine-based therapy. In some embodiments, the tumor size is reduced at least about 10% (including for example at least about any of 20%, 30%, 40%, 60%, 70%, 80%, 90%, or 100%). In some embodiments, the taxane is paclitaxel. In some embodiments, the taxane in the nanoparticle in the composition is administered by intravenous administration. In some embodiments, the individual has non-metastatic pancreatic cancer. In some embodiments, the individual has primary pancreatic cancer.

In some embodiments, there is provided a method of reducing pancreatic cancer tumor size in an individual, comprising administering to the individual an effective amount of a composition comprising nanoparticles comprising a taxane and an albumin and wherein the individual exhibits a less desirable degree of responsiveness to a gemcitabine-based therapy. In some embodiments, the tumor size is reduced at least about 10% (including for example at least about any of 20%, 30%, 40%, 60%, 70%, 80%, 90%, or 100%). In some embodiments, the taxane is paclitaxel. In some embodiments, the taxane in the nanoparticle in the composition is administered by intravenous administration. In some embodiments, the individual has non-metastatic pancreatic cancer. In some embodiments, the individual has primary pancreatic cancer.

In some embodiments, there is provided a method of reducing pancreatic cancer tumor size in an individual, comprising administering to the individual an effective amount of a composition comprising nanoparticles comprising a taxane and an albumin, and wherein the individual has recurrent pancreatic cancer (for example, the individual develops pancreatic cancer after about any of about 2, 3, 4, 5, 6, 7, 8, 9, 10, 11, 12, 24, or 36 months upon the cessation of a a gemcitabine-based therapy). In some embodiments, the tumor size is reduced at least about 10% (including for example at least about any of 20%, 30%, 40%, 60%, 70%, 80%, 90%, or 100%). In some embodiments, the taxane is paclitaxel. In some embodiments, the taxane in the nanoparticle in the composition is administered by intravenous administration. In some embodiments, the individual has non-metastatic pancreatic cancer. In some embodiments, the individual has primary pancreatic cancer.

In some embodiments, there is provided a method of reducing pancreatic cancer tumor size in an individual, comprising administering to the individual an effective amount of a composition comprising nanoparticles comprising a taxane and an albumin, and wherein a gemcitabine-based therapy has stopped (for example for at least 1, 2, 3, 4, 5, 6, 7, 8, 9, or 10 months) when initiating the administration of the effective amount of the composition comprising nanoparticles comprising a taxane and an albumin to the individual. In some embodiments, the tumor size is reduced at least about 10% (including for example at least about any of 20%, 30%, 40%, 60%, 70%, 80%, 90%, or 100%). In some embodiments, the taxane is paclitaxel. In some embodiments, the taxane in the nanoparticle in the composition is administered by intravenous administration. In some embodiments, the individual has non-metastatic pancreatic cancer. In some embodiments, the individual has primary pancreatic cancer.

In some embodiments, there is provided a method of prolonging time to disease progression of pancreatic cancer (e.g., progression-free survival) in an individual, comprising administering to the individual an effective amount of a composition comprising nanoparticles comprising a taxane and an albumin, wherein the individual has progressed on gemcitabine-based therapy. In some embodiments, the method prolongs the time to disease progression by at least any of 1, 2, 3, 4, 5, 6, 7, 8, 9, 10, 11, 12 weeks. In some embodiments, the method prolongs the time to disease progression by at least any of 1.0, 1.2, 1.4, 1.6, 1.8, 2.0, 2.2, 2.4, 2.6, 2.8, 3.0, 3.2, 3.4, 3.6, 3.8, 4.0, 4.2, 4.4, 4.6, 4.8, 5.0, 5.2, 5.4, 5.6, 5.8, 6.0, 6.2, 6.4, 6.6, 6.8, 7.0, 7.2, 7.4, 7.6, 7.8, 8.0, 8.2, 8.4, 8.6, 8.8, 9.0, 9.2, 9.4, 9.6, 9.8, 10.0, 10.2, 10.4, 10.6, 10.8, 11.0, 11.2, 11.4, 11.6, 11.8, 12.0, 13, 14, 15, 16, 17, 18, 19, 20, 21, 22, 23, 24, 30, 36, 42, 48, 54, 60, 66, or 72 months. In some embodiments, the taxane is paclitaxel. In some embodiments, the taxane in the nanoparticle in the composition is administered by intravenous administration.

In some embodiments, there is provided a method of prolonging overall survival of an individual having pancreatic cancer, comprising administering to the individual an effective amount of a composition comprising nanoparticles comprising a taxane and an albumin, wherein the individual has progressed on gemcitabine-based therapy. In some embodiments, the method prolongs the survival of the individual by at least any of 1.0, 1.2, 1.4, 1.6, 1.8, 2.0, 2.2, 2.4, 2.6, 2.8, 3.0, 3.2, 3.4, 3.6, 3.8, 4.0, 4.2, 4.4, 4.6, 4.8, 5.0, 5.2, 5.4, 5.6, 5.8, 6.0, 6.2, 6.4, 6.6, 6.8, 7.0, 7.2, 7.4, 7.6, 7.8, 8.0, 8.2, 8.4, 8.6, 8.8, 9.0, 9.2, 9.4, 9.6, 9.8, 10.0, 10.2, 10.4, 10.6, 10.8, 11.0, 11.2, 11.4, 11.6, 11.8, 12.0, 13, 14, 15, 16, 17, 18, 19, 20, 21, 22, 23, 24, 30, 36, 42, 48, 54, 60, 66, or 72 months. In some embodiments, the taxane is paclitaxel. In some embodiments, the taxane in the nanoparticle in the composition is administered by intravenous administration.

In some embodiments, there is provided a method of disrupting (such as destroying) pancreatic cancer stroma of an individual having pancreatic cancer, comprising administering to the individual an effective amount of a composition comprising nanoparticles comprising a taxane and an albumin, wherein the individual has progressed on gemcitabine-based therapy. In some embodiments, the pancreatic cancer stroma is disrupted or destroyed by at least about 10% (including for example at least about any of 20%, 30%, 40%, 60%, 70%, 80%, 90%, or 100%). In some embodiments, the taxane is paclitaxel. In some embodiments, the taxane in the nanoparticle in the composition is administered by intravenous administration. In some embodiments, the individual has non-metastatic pancreatic cancer. In some embodiments, the individual has primary pancreatic cancer.

In some embodiments, there is provided a method of disrupting (such as destroying) pancreatic cancer stroma of an individual having pancreatic cancer, comprising administering to the individual an effective amount of a composition comprising nanoparticles comprising a taxane and an albumin, and wherein the individual is resistant or refractory to a gemcitabine-based therapy. In some embodiments, the pancreatic cancer stroma is disrupted or destroyed by at least about 10% (including for example at least about any of 20%, 30%, 40%, 60%, 70%, 80%, 90%, or 100%). In some embodiments, the taxane is paclitaxel. In some embodiments, the taxane in the nanoparticle in the composition is administered by intravenous administration. In some embodiments, the individual has non-metastatic pancreatic cancer. In some embodiments, the individual has primary pancreatic cancer.

In some embodiments, there is provided a method of disrupting (such as destroying) pancreatic cancer stroma of an individual having pancreatic cancer, comprising administering to the individual an effective amount of a composition comprising nanoparticles comprising a taxane and an albumin, and wherein the individual has failed to respond to a gemcitabine-based therapy. In some embodiments, the pancreatic cancer stroma is disrupted or destroyed by at least about 10% (including for example at least about any of 20%, 30%, 40%, 60%, 70%, 80%, 90%, or 100%). In some embodiments, the taxane is paclitaxel. In some embodiments, the taxane in the nanoparticle in the composition is administered by intravenous administration. In some embodiments, the individual has non-metastatic pancreatic cancer. In some embodiments, the individual has primary pancreatic cancer.

In some embodiments, there is provided a method of disrupting (such as destroying) pancreatic cancer stroma of an individual having pancreatic cancer, comprising administering to the individual an effective amount of a composition comprising nanoparticles comprising a taxane and an albumin, and wherein the individual exhibits a less desirable degree of responsiveness to a gemcitabine-based therapy. In some embodiments, the pancreatic cancer stroma is disrupted or destroyed by at least about 10% (including for example at least about any of 20%, 30%, 40%, 60%, 70%, 80%, 90%, or 100%). In some embodiments, the taxane is paclitaxel. In some embodiments, the taxane in the nanoparticle in the composition is administered by intravenous administration. In some embodiments, the individual has non-metastatic pancreatic cancer. In some embodiments, the individual has primary pancreatic cancer.

In some embodiments, there is provided a method of disrupting (such as destroying) pancreatic cancer stroma of an individual having pancreatic cancer, comprising administering to the individual an effective amount of a composition comprising nanoparticles comprising a taxane and an albumin, and wherein the individual has recurrent pancreatic cancer (for example, the individual develops pancreatic cancer after about any of about 2, 3, 4, 5, 6, 7, 8, 9, 10, 11, 12, 24, or 36 months upon the cessation of a gemcitabine-based therapy). In some embodiments, the pancreatic cancer stroma is disrupted or destroyed by at least about 10% (including for example at least about any of 20%, 30%, 40%, 60%, 70%, 80%, 90%, or 100%). In some embodiments, the taxane is paclitaxel. In some embodiments, the taxane in the nanoparticle in the composition is administered by intravenous administration. In some embodiments, the individual has non-metastatic pancreatic cancer. In some embodiments, the individual has primary pancreatic cancer.

In some embodiments, there is provided a method of disrupting (such as destroying) pancreatic cancer stroma of an individual having pancreatic cancer, comprising administering to the individual an effective amount of a composition comprising nanoparticles comprising a taxane and an albumin, and wherein a gemcitabine-based therapy has stopped (for example for at least 1, 2, 3, 4, 5, 6, 7, 8, 9, or 10 months) when initiating the administration of the effective amount of the composition comprising nanoparticles comprising a taxane and an albumin to the individual. In some embodiments, the pancreatic cancer stroma is disrupted or destroyed by at least about 10% (including for example at least about any of 20%, 30%, 40%, 60%, 70%, 80%, 90%, or 100%). In some embodiments, the taxane is paclitaxel. In some embodiments, the taxane in the nanoparticle in the composition is administered by intravenous administration. In some embodiments, the individual has non-metastatic pancreatic cancer. In some embodiments, the individual has primary pancreatic cancer.

In some embodiments, there is provided a method of improving one or more clinical benefits of an individual having pancreatic cancer, comprising administering to the individual an effective amount of a composition comprising nanoparticles comprising a taxane and an albumin, wherein the individual has progressed on gemcitabine-based therapy. Clinical benefits includes, but are not limited to, improved/better quality of life, improved/better symptom control of pancreatic cancer, and increased weight gain. In some embodiments, the individual has improved quality of life, improved symptom control and increased weight gain. In some embodiments, the taxane is paclitaxel. In some embodiments, the taxane in the nanoparticle in the composition is administered by intravenous administration.

In some embodiments, there is provided a method of alleviating one or more symptoms in an individual having pancreatic cancer, comprising administering to the individual an effective amount of a composition comprising nanoparticles comprising a taxane and an albumin, wherein the individual has progressed on gemcitabine-based therapy. In some embodiments, the taxane in the nanoparticle in the composition is administered by intravenous administration.

In some embodiments, there is provided a method of treating pancreatic cancer in an individual comprising administering to the individual an effective amount of a composition comprising ABRAXANE®, wherein the individual has progressed on gemcitabine-based therapy and wherein the ABRAXANE® is administered weekly or weekly for three out of four weeks at a dose ranging from about 80 mg/m$^2$ to about 150 mg/m$^2$ (for example, about 100 mg/m$^2$). In some embodiments, the ABRAXANE® is administered by intravenous administration. In some embodiments, the individual has non-metastatic pancreatic cancer. In some embodiments, the individual has primary pancreatic cancer.

In some embodiments, there is provided a method of treating pancreatic cancer in an individual comprising administering to the individual an effective amount of a composition comprising ABRAXANE®, wherein the ABRAXANE® is administered weekly or weekly for three out of four weeks at a dose ranging from about 80 mg/m$^2$ to about 150 mg/m$^2$ (for example, about 100 mg/m$^2$) and wherein the individual is resistant or refractory to a gemcitabine-based therapy. In some embodiments, the ABRAXANE® is administered by intravenous administration. In some embodiments, the individual has non-metastatic pancreatic cancer. In some embodiments, the individual has primary pancreatic cancer.

In some embodiments, there is provided a method of treating pancreatic cancer in an individual comprising administering to the individual an effective amount of a composition comprising ABRAXANE®, wherein the ABRAXANE® is administered weekly or weekly for three out of four weeks at a dose ranging from about 80 mg/m$^2$ to about 150 mg/m$^2$ (for example, about 100 mg/m$^2$) and wherein the individual has failed to respond to a gemcitabine-based therapy. In some embodiments, the ABRAXANE® is administered by intravenous administration. In some embodiments, the individual has non-metastatic pancreatic cancer. In some embodiments, the individual has primary pancreatic cancer.

In some embodiments, there is provided a method of treating pancreatic cancer in an individual comprising administering to the individual an effective amount of a composition comprising ABRAXANE®, wherein the ABRAXANE® is administered weekly or weekly for three out of four weeks at a dose ranging from about 80 mg/m$^2$ to about 150 mg/m$^2$ (for example, about 100 mg/m$^2$) and wherein the individual exhibits a less desirable degree of responsiveness to a gemcitabine-based therapy. In some embodiments, the ABRAXANE® is administered by intravenous administration. In some embodiments, the individual has non-metastatic pancreatic cancer. In some embodiments, the individual has primary pancreatic cancer.

In some embodiments, there is provided a method of treating pancreatic cancer in an individual comprising administering to the individual an effective amount of a composition comprising ABRAXANE®, wherein the ABRAXANE® is administered weekly or weekly for three out of four weeks at a dose ranging from about 80 mg/m$^2$ to about 150 mg/m$^2$ (for example, about 100 mg/m$^2$) and wherein the individual has recurrent pancreatic cancer (for example, the individual develops pancreatic cancer after about any of about 2, 3, 4, 5, 6, 7, 8, 9, 10, 11, 12, 24, or 36 months upon the cessation of a gemcitabine-based therapy). In some embodiments, the ABRAXANE® is administered by intravenous administration. In some embodiments, the individual has non-metastatic pancreatic cancer. In some embodiments, the individual has primary pancreatic cancer.

In some embodiments, there is provided a method of treating pancreatic cancer in an individual comprising administering to the individual an effective amount of a composition comprising ABRAXANE®, wherein the ABRAXANE® is administered weekly or weekly for three out of four weeks at a dose ranging from about 80 mg/m$^2$ to about 150 mg/m$^2$ (for example, about 100 mg/m$^2$) and wherein a gemcitabine-based therapy has stopped (for example for at least 1, 2, 3, 4, 5, 6, 7, 8, 9, or 10 months) when initiating the administration of the effective amount of the composition comprising ABRAXANE® to the individual. In some embodiments, the ABRAXANE® is administered by intravenous administration. In some embodiments, the individual has non-metastatic pancreatic cancer. In some embodiments, the individual has primary pancreatic cancer.

In some embodiments, there is provided a method of treating pancreatic cancer in an individual comprising administering to the individual an effective amount of a composition comprising ABRAXANE®, wherein the individual has progressed on gemcitabine-based therapy and wherein the ABRAXANE® is administered once every three weeks at a dose ranging from about 200 mg/m$^2$ to about 300 mg/m$^2$ (for example, about 260 mg/m$^2$). In some embodiments, the ABRAXANE® is administered by intravenous administration. In some embodiments, the individual has non-metastatic pancreatic cancer. In some embodiments, the individual has primary pancreatic cancer.

In some embodiments, there is provided a method of treating pancreatic cancer in an individual comprising administering to the individual an effective amount of a composition comprising ABRAXANE®, wherein the ABRAXANE® is administered once every three weeks at a dose ranging from about 200 mg/m$^2$ to about 300 mg/m$^2$ (for example, about 260 mg/m$^2$) and wherein the individual is resistant or refractory to a gemcitabine-based therapy. In some embodiments, the ABRAXANE® is administered by intravenous administration. In some embodiments, the individual has non-metastatic pancreatic cancer. In some embodiments, the individual has primary pancreatic cancer.

In some embodiments, there is provided a method of treating pancreatic cancer in an individual comprising administering to the individual an effective amount of a composition comprising ABRAXANE®, wherein the ABRAXANE® is administered once every three weeks at a dose ranging from about 200 mg/m$^2$ to about 300 mg/m$^2$ (for example, about 260 mg/m$^2$), and wherein the individual has failed to respond to a gemcitabine-based therapy. In some embodiments, the ABRAXANE® is administered by intravenous administration. In some embodiments, the individual has non-metastatic pancreatic cancer. In some embodiments, the individual has primary pancreatic cancer.

In some embodiments, there is provided a method of treating pancreatic cancer in an individual comprising administering to the individual an effective amount of a composition comprising ABRAXANE®, wherein the ABRAXANE® is administered once every three weeks at a dose ranging from about 200 mg/m$^2$ to about 300 mg/m$^2$ (for example, about 260 mg/m$^2$), and wherein the individual exhibits a less desirable degree of responsiveness to a gemcitabine-based therapy. In some embodiments, the ABRAXANE® is administered by intravenous administration. In some embodiments, the individual has non-metastatic pancreatic cancer. In some embodiments, the individual has primary pancreatic cancer.

In some embodiments, there is provided a method of treating pancreatic cancer in an individual comprising administering to the individual an effective amount of a composition comprising ABRAXANE®, wherein the ABRAXANE® is administered once every three weeks at a dose ranging from about 200 mg/m$^2$ to about 300 mg/m$^2$ (for example, about 260 mg/m$^2$) and wherein the individual has recurrent pancreatic cancer (for example, the individual develops pancreatic cancer after about any of about 2, 3, 4, 5, 6, 7, 8, 9, 10, 11, 12, 24, or 36 months upon the cessation of a gemcitabine-based therapy). In some embodiments, the ABRAXANE® is administered by intravenous administration. In some embodiments, the individual has non-metastatic pancreatic cancer. In some embodiments, the individual has primary pancreatic cancer.

In some embodiments, there is provided a method of treating pancreatic cancer in an individual comprising administering to the individual an effective amount of a composition comprising ABRAXANE®, wherein the ABRAXANE® is administered once every three weeks at a dose ranging from about 200 mg/m$^2$ to about 300 mg/m$^2$ (for example, about 260 mg/m$^2$) and wherein a gemcitabine-based therapy has stopped (for example for at least 1, 2, 3, 4, 5, 6, 7, 8, 9, or 10 months) when initiating the administration of the effective amount of the composition comprising ABRAXANE® to the individual. In some embodiments, the ABRAXANE® is administered by intravenous administration. In some embodiments, the individual has non-metastatic pancreatic cancer. In some embodiments, the individual has primary pancreatic cancer.

In some embodiments, there is provided a method of treating pancreatic cancer in an individual comprising administering to the individual an effective amount of a composition comprising ABRAXANE®, wherein the individual has progressed on gemcitabine-based therapy and wherein the ABRAXANE® is administered weekly or weekly for three out of four weeks at a dose of about 150 mg/m$^2$. In some embodiments, the ABRAXANE® is administered by intravenous administration. In some embodiments, the individual has non-metastatic pancreatic cancer. In some embodiments, the individual has primary pancreatic cancer.

In some embodiments, there is provided a method of treating pancreatic cancer in an individual comprising administering to the individual an effective amount of a composition comprising ABRAXANE®, wherein the ABRAXANE® is administered weekly or weekly for three out of four weeks at a dose of about 150 mg/m$^2$ and wherein the individual is resistant or refractory to a gemcitabine-based therapy. In some embodiments, the ABRAXANE® is administered by intravenous administration. In some embodiments, the individual has non-metastatic pancreatic cancer. In some embodiments, the individual has primary pancreatic cancer.

In some embodiments, there is provided a method of treating pancreatic cancer in an individual comprising administering to the individual an effective amount of a composition comprising ABRAXANE®, wherein the ABRAXANE® is administered weekly or weekly for three out of four weeks at a dose of about 150 mg/m$^2$ and wherein the individual has failed to respond to a gemcitabine-based therapy. In some embodiments, the ABRAXANE® is administered by intravenous administration. In some embodiments, the individual has non-metastatic pancreatic cancer. In some embodiments, the individual has primary pancreatic cancer.

In some embodiments, there is provided a method of treating pancreatic cancer in an individual comprising administering to the individual an effective amount of a composition comprising ABRAXANE®, wherein the ABRAXANE® is administered weekly or weekly for three out of four weeks at a dose of about 150 mg/m$^2$ and wherein the individual exhibits a less desirable degree of responsiveness to a gemcitabine-based therapy. In some embodiments, the ABRAXANE® is administered by intravenous administration. In some embodiments, the individual has non-metastatic pancreatic cancer. In some embodiments, the individual has primary pancreatic cancer.

In some embodiments, there is provided a method of treating pancreatic cancer in an individual comprising administering to the individual an effective amount of a composition comprising ABRAXANE®, wherein the ABRAXANE® is administered weekly or weekly for three out of four weeks at a dose of about 150 mg/m$^2$ and wherein the individual has recurrent pancreatic cancer (for example, the individual develops pancreatic cancer after about any of about 2, 3, 4, 5, 6, 7, 8, 9, 10, 11, 12, 24, or 36 months upon the cessation of a gemcitabine-based therapy). In some embodiments, the ABRAXANE® is administered by intravenous administration. In some embodiments, the individual has non-metastatic pancreatic cancer. In some embodiments, the individual has primary pancreatic cancer.

In some embodiments, there is provided a method of treating pancreatic cancer in an individual comprising administering to the individual an effective amount of a composition comprising ABRAXANE®, wherein the ABRAXANE® is administered weekly or weekly for three out of four weeks at a dose of about 150 mg/m$^2$ and wherein a gemcitabine-based therapy has stopped (for example for at least 1, 2, 3, 4, 5, 6, 7, 8, 9, or 10 months) when initiating the administration of the effective amount of the composition comprising ABRAXANE® to the individual. In some embodiments, the ABRAXANE® is administered by intravenous administration. In some embodiments, the individual has non-metastatic pancreatic cancer. In some embodiments, the individual has primary pancreatic cancer.

In some embodiments, there is provided a method of treating pancreatic cancer in an individual comprising administering to the individual an effective amount of a composition comprising ABRAXANE®, wherein the individual has progressed on gemcitabine-based therapy and wherein the ABRAXANE® is administered once every three weeks at a dose of about 260 mg/m$^2$. In some embodiments, the ABRAXANE® is administered by intravenous administration. In some embodiments, the individual has non-metastatic pancreatic cancer. In some embodiments, the individual has primary pancreatic cancer.

In some embodiments, there is provided a method of treating pancreatic cancer in an individual comprising administering to the individual an effective amount of a composition comprising ABRAXANE®, wherein the ABRAXANE® is administered once every three weeks at a dose of about 260 mg/m$^2$ and wherein the individual is resistant or refractory to a gemcitabine-based therapy. In some embodiments, the ABRAXANE® is administered by intravenous administration. In some embodiments, the individual has non-metastatic pancreatic cancer. In some embodiments, the individual has primary pancreatic cancer.

In some embodiments, there is provided a method of treating pancreatic cancer in an individual comprising administering to the individual an effective amount of a composition comprising ABRAXANE®, wherein the ABRAXANE® is administered once every three weeks at a dose of about 260 mg/m² and wherein the individual has failed to respond to a gemcitabine-based therapy. In some embodiments, the ABRAXANE® is administered by intravenous administration. In some embodiments, the individual has non-metastatic pancreatic cancer. In some embodiments, the individual has primary pancreatic cancer.

In some embodiments, there is provided a method of treating pancreatic cancer in an individual comprising administering to the individual an effective amount of a composition comprising ABRAXANE®, wherein the ABRAXANE® is administered once every three weeks at a dose of about 260 mg/m² and wherein the individual exhibits a less desirable degree of responsiveness to a gemcitabine-based therapy. In some embodiments, the ABRAXANE® is administered by intravenous administration. In some embodiments, the individual has non-metastatic pancreatic cancer. In some embodiments, the individual has primary pancreatic cancer.

In some embodiments, there is provided a method of treating pancreatic cancer in an individual comprising administering to the individual an effective amount of a composition comprising ABRAXANE®, wherein the ABRAXANE® is administered once every three weeks at a dose of about 260 mg/m² and wherein the individual has recurrent pancreatic cancer (for example, the individual develops pancreatic cancer after about any of about 2, 3, 4, 5, 6, 7, 8, 9, 10, 11, 12, 24, or 36 months upon the cessation of a gemcitabine-based therapy). In some embodiments, the ABRAXANE® is administered by intravenous administration. In some embodiments, the individual has non-metastatic pancreatic cancer. In some embodiments, the individual has primary pancreatic cancer.

In some embodiments, there is provided a method of treating pancreatic cancer in an individual comprising administering to the individual an effective amount of a composition comprising ABRAXANE®, wherein the ABRAXANE® is administered once every three weeks at a dose of about 260 mg/m² and wherein a gemcitabine-based therapy has stopped (for example for at least 1, 2, 3, 4, 5, 6, 7, 8, 9, or 10 months) when initiating the administration of the effective amount of the composition comprising ABRAXANE® to the individual. In some embodiments, the ABRAXANE® is administered by intravenous administration. In some embodiments, the individual has non-metastatic pancreatic cancer. In some embodiments, the individual has primary pancreatic cancer.

It is understood that any of the embodiments described in this section apply to the embodiments provided in the section "methods of combination therapy." For example, in some embodiments, there is provided a method of alleviating one of more symptoms in an individual having pancreatic cancer, comprising administering to the individual: a) an effective amount of a composition comprising nanoparticles comprising taxane and an albumin, and b) an effective amount of another agent, wherein the other agent is not gemcitabine, wherein the individual has progressed on gemcitabine-based therapy, and wherein the nanoparticle composition and the other agent are administered concurrently.

Methods of Combination Therapy

The methods of administering the composition comprising nanoparticles comprising a taxane and an albumin in some embodiments are carried out in conjunction with the administration of another agent in an individual. In some embodiments, the individual has not been previously treated for pancreatic cancer. In some embodiments, the individual has been previously treated for pancreatic cancer.

The methods of administering the composition comprising nanoparticles comprising a taxane and an albumin in some embodiments are carried out in conjunction with the administration of another agent; for example, in an individual who has been previously treated for pancreatic cancer.

In some embodiments, there is provided a method of treating pancreatic cancer in an individual in need thereof, comprising administering to the individual (a) an effective amount of a composition comprising nanoparticles comprising taxane and albumin; and (b) an effective amount of another agent, wherein the individual has progressed on a prior therapy (for example progressed after any of about 3, 6, 9, or 12 months upon initiation of the prior therapy). In some embodiments, the prior therapy is gemcitabine-based therapy, erlotinib-based therapy, or 5-FU-based therapy. In some embodiments, the nanoparticles comprise paclitaxel coated with albumin. In some embodiments, the average particle size of the nanoparticles in the composition is no greater than about 200 nm (such as less than about 200 nm). In some embodiments, the composition comprises Nab-paclitaxel (ABRAXANE®). In some embodiments, the composition is the Nab-paclitaxel (ABRAXANE®). In some embodiments, the nanoparticle composition and the other agent have synergistic effect on treating pancreatic cancer. In some embodiments, the other agent sensitizes the pancreatic cancer cells to the treatment with the nanoparticle composition. In some embodiments, the individual has non-metastatic pancreatic cancer. In some embodiments, the individual has primary pancreatic cancer.

In some embodiments, there is provided a method of treating pancreatic cancer in an individual in need thereof, comprising administering to the individual (a) an effective amount of a composition comprising nanoparticles comprising taxane and albumin; and (b) an effective amount of another agent, and wherein the individual is resistant or refractory to a prior therapy. In some embodiments, the prior therapy is gemcitabine-based therapy, erlotinib-based therapy, or 5-FU-based therapy. In some embodiments, the nanoparticles comprise paclitaxel coated with albumin. In some embodiments, the average particle size of the nanoparticles in the composition is no greater than about 200 nm (such as less than about 200 nm). In some embodiments, the composition comprises Nab-paclitaxel (ABRAXANE®). In some embodiments, the composition is the Nab-paclitaxel (ABRAXANE®). In some embodiments, the nanoparticle composition and the other agent have synergistic effect on treating pancreatic cancer. In some embodiments, the other agent sensitizes the pancreatic cancer cells to the treatment with the nanoparticle composition. In some embodiments, the individual has non-metastatic pancreatic cancer. In some embodiments, the individual has primary pancreatic cancer.

In some embodiments, there is provided a method of treating pancreatic cancer in an individual in need thereof, comprising administering to the individual (a) an effective amount of a composition comprising nanoparticles comprising taxane and albumin; and (b) an effective amount of another agent, and wherein the individual has failed to respond to a prior therapy. In some embodiments, the prior therapy is gemcitabine-based therapy, erlotinib-based therapy, or 5-FU-based therapy. In some embodiments, the nanoparticles comprise paclitaxel coated with albumin. In some embodiments, the average particle size of the nanoparticles in the composition is no greater than about 200 nm (such as less than about 200 nm). In some embodiments, the composition comprises Nab-paclitaxel (ABRAXANE®). In some embodiments, the composition is the Nab-paclitaxel (ABRAXANE®). In some embodiments, the nanoparticle composition and the other agent have synergistic effect on treating pancreatic cancer. In some embodiments, the other agent sensitizes the pancreatic cancer cells to the treatment with the nanoparticle composition. In some embodiments, the individual has non-metastatic pancreatic cancer. In some embodiments, the individual has primary pancreatic cancer.

In some embodiments, there is provided a method of treating pancreatic cancer in an individual in need thereof, comprising administering to the individual (a) an effective amount of a composition comprising nanoparticles comprising taxane and albumin; and (b) an effective amount of another agent, and wherein the individual exhibits a less desirable degree of responsiveness to a prior therapy. In some embodiments, the prior therapy is gemcitabine-based therapy, erlotinib-based therapy, or 5-FU-based therapy. In some embodiments, the nanoparticles comprise paclitaxel coated with albumin. In some embodiments, the average particle size of the nanoparticles in the composition is no greater than about 200 nm (such as less than about 200 nm). In some embodiments, the composition comprises Nab-paclitaxel (ABRAXANE®). In some embodiments, the composition is the Nab-paclitaxel (ABRAXANE®). In some embodiments, the nanoparticle composition and the other agent have synergistic effect on treating pancreatic cancer. In some embodiments, the other agent sensitizes the pancreatic cancer cells to the treatment with the nanoparticle composition. In some embodiments, the individual has non-metastatic pancreatic cancer. In some embodiments, the individual has primary pancreatic cancer.

In some embodiments, there is provided a method of treating pancreatic cancer in an individual in need thereof, comprising administering to the individual (a) an effective amount of a composition comprising nanoparticles comprising taxane and albumin; and (b) an effective amount of another agent, and wherein the individual has recurrent pancreatic cancer (for example, the individual develops pancreatic cancer after about any of about 2, 3, 4, 5, 6, 7, 8, 9, 10, 11, 12, 24, or 36 months upon the cessation of a prior therapy). In some embodiments, the prior therapy is gemcitabine-based therapy, erlotinib-based therapy, or 5-FU-based therapy. In some embodiments, the nanoparticles comprise paclitaxel coated with albumin. In some embodiments, the average particle size of the nanoparticles in the composition is no greater than about 200 nm (such as less than about 200 nm). In some embodiments, the composition comprises Nab-paclitaxel (ABRAXANE®). In some embodiments, the composition is the Nab-paclitaxel (ABRAXANE®). In some embodiments, the nanoparticle composition and the other agent have synergistic effect on treating pancreatic cancer. In some embodiments, the other agent sensitizes the pancreatic cancer cells to the treatment with the nanoparticle composition. In some embodiments, the individual has non-metastatic pancreatic cancer. In some embodiments, the individual has primary pancreatic cancer.

In some embodiments, there is provided a method of treating pancreatic cancer in an individual in need thereof, comprising administering to the individual (a) an effective amount of a composition comprising nanoparticles comprising taxane and albumin; and (b) an effective amount of another agent, and wherein a prior therapy has stopped (for example for at least 1, 2, 3, 4, 5, 6, 7, 8, 9, or 10 months) when administering the effective amount of the composition comprising nanoparticles comprising taxane and albumin and the effective amount of the another agent to the individual. In some embodiments, the prior therapy is gemcitabine-based therapy, erlotinib-based therapy, or 5-FU-based therapy. In some embodiments, the nanoparticles comprise paclitaxel coated with albumin. In some embodiments, the average particle size of the nanoparticles in the composition is no greater than about 200 nm (such as less than about 200 nm). In some embodiments, the composition comprises Nab-paclitaxel (ABRAXANE®). In some embodiments, the composition is the Nab-paclitaxel (ABRAXANE®). In some embodiments, the nanoparticle composition and the other agent have synergistic effect on treating pancreatic cancer. In some embodiments, the other agent sensitizes the pancreatic cancer cells to the treatment with the nanoparticle composition. In some embodiments, the individual has non-metastatic pancreatic cancer. In some embodiments, the individual has primary pancreatic cancer.

In some embodiments, levels of serum CA 19-9 in the individual administered with the nanoparticle composition and the other agent of the present invention decrease significantly. In some embodiments, the levels of serum CA 19-9 are decreased by at least about 20% (including for example at least about any of about 20%, 30%, 40%, 50%, 52%, 53%, 55%, 57%, 59%, 60%, 70%, 80%, 90%, or 100%) in comparison to the levels of serum CA 19-9 prior to the therapy. In some embodiments, the levels of serum CA 19-9 are decreased by at least about 50% in comparison to the levels of serum CA 19-9 prior to the therapy.

In some embodiments, the other agent is not gemcitabine. In some embodiments, the other agent is not a platinum-based agent (such as carboplatin or cisplatin). In some embodiments, the method does not comprise administration of an inhibitor of the hedgehog signaling pathway (a hedgehog inhibitor).

In some embodiments, the other agent is an antimetabolite agent, a tyrosine kinase inhibitor (e.g., an EGFR inhibitor), a matrix metalloproteinase inhibitor, a topoisomerase inhibitor, a proteasome inhibitor, a platinum-based agent, a therapeutic antibody, a farnesyltransferase inhibitor, an anti-angiogenic agent, and a macrolide.

In some embodiments, the chemotherapeutic agent is any of (and in some embodiments selected from the group consisting of) selected from the group consisting of vandetanib (e.g., Zactima™), 5-fluororuracil (e.g., CARAC® or EFUDEX®), erlotinib (e.g., TARCEVA®), gefitinib (IRESSA®), marimastat, cisplatin, carboplatin, satraplatin, irinotecan (e.g., CAMTOSAR®), tipifarnib (e.g., ZARNESTRA™), oxaliplatin (e.g., ELOXATIN®), pemetrexed (e.g., ALIMTA®), exatecan, capecitabine (e.g., XELODA®), raltitrexed (e.g., TOMUDEX®), cetuximab (ERBITUX®), bevacizumab (e.g., AVASTIN®), bortezomib (e.g., VELCADE®), rapamycin, or gemcitabine. In some embodiments, the chemotherapeutic agent is any of (and in some embodiments selected from the group consisting of) selected from the group consisting of 5-fluororuracil (e.g., CARAC® or EFUDEX®), erlotinib (e.g., TARCEVA®), gefitinib (IRESSA®), marimastat, irinotecan (e.g., CAMTOSAR®), tipifarnib (e.g., ZARNESTRA™), pemetrexed (e.g., ALIMTA®), exatecan, capecitabine (e.g., XELODA®), raltitrexed (e.g., TOMUDEX®), cetuximab (ERBITUX®), bevacizumab (e.g., AVASTIN®), bortezomib (e.g., VELCADE®), rapamycin, or gemcitabine.

In some embodiments, the other chemotherapeutic agent is an antimetabolite agent. An antimetabolic agent is an agent which is structurally similar to a metabolite, but cannot be used by the body in a productive manner. Many antimetabolite agents interfere with production of nucleic acids, RNA and DNA. For example, the antimetabolite can be a nucleoside analog, which includes, but is not limited to, 5-fluororuracil (e.g., CARAC® or EFUDEX®), gemcitabine (GEMZAR®), pemetrexed (e.g., ALIMTA®), raltitrexed (e.g., TOMUDEX®), and capecitabine (e.g., XELODA®). Thus, in some embodiments, there is provided a method of treating pancreatic cancer in an individual in need thereof, comprising administering to the individual (a) an effective amount of a composition comprising nanoparticles comprising taxane and albumin; and (b) an effective amount of an antimetabolite agent, wherein the individual has progressed on gemcitabine-based therapy. In some embodiments, the individual has non-metastatic pancreatic cancer. In some embodiments, the individual has primary pancreatic cancer. In some embodiments, the antimetabolite is 5-fluorouracil, pemetrexed, raltitrexed, gemcitabine, or capecitabine. In some embodiments, the antimetabolite agent is not gemcitabine.

In some embodiments, there is provided a method of treating pancreatic cancer in an individual in need thereof, comprising administering to the individual (a) an effective amount of a composition comprising nanoparticles comprising taxane and albumin; and (b) an effective amount of an antimetabolite agent, and wherein the individual is resistant or refractory to a gemcitabine-based therapy. In some embodiments, the individual has non-metastatic pancreatic cancer. In some embodiments, the individual has primary pancreatic cancer. In some embodiments, the antimetabolite is 5-fluorouracil, pemetrexed, raltitrexed, gemcitabine, or capecitabine. In some embodiments, the antimetabolite agent is not gemcitabine.

In some embodiments, there is provided a method of treating pancreatic cancer in an individual in need thereof, comprising administering to the individual (a) an effective amount of a composition comprising nanoparticles comprising taxane and albumin; and (b) an effective amount of an antimetabolite agent, and wherein the individual has recurrent pancreatic cancer (for example, the individual develops pancreatic cancer after about any of about 2, 3, 4, 5, 6, 7, 8, 9, 10, 11, 12, 24, or 36 months upon the cessation of a gemcitabine-based therapy). In some embodiments, the individual has non-metastatic pancreatic cancer. In some embodiments, the individual has primary pancreatic cancer. In some embodiments, the antimetabolite is 5-fluorouracil, pemetrexed, raltitrexed, gemcitabine, or capecitabine. In some embodiments, the antimetabolite agent is not gemcitabine.

In some embodiments, there is provided a method of treating pancreatic cancer in an individual in need thereof, comprising administering to the individual (a) an effective amount of a composition comprising nanoparticles comprising taxane and albumin; and (b) an effective amount of an antimetabolite agent, and wherein a gemcitabine-based therapy has stopped (for example for at least 1, 2, 3, 4, 5, 6, 7, 8, 9, or 10 months) when administering the effective amount of the composition comprising nanoparticles comprising taxane and albumin and the effective amount of the antimetabolite agent to the individual. In some embodiments, the individual has non-metastatic pancreatic cancer. In some embodiments, the individual has primary pancreatic cancer. In some embodiments, the antimetabolite is 5-fluorouracil, pemetrexed, raltitrexed, gemcitabine, or capecitabine. In some embodiments, the antimetabolite agent is not gemcitabine.

In some embodiments, the other chemotherapeutic agent is a tyrosine kinase (e.g., EGFR) inhibitor. Suitable tyrosine kinase inhibitors include, but are not limited to, vandetanib (e.g., Zactima™), erlotinib (e.g., TARCEVA®) and gefitinib (IRESSA®). Thus, in some embodiments, there is provided a method of treating pancreatic cancer in an individual in need thereof, comprising administering to the individual (a) an effective amount of a composition comprising nanoparticles comprising taxane and albumin; and (b) an effective amount of a tyrosine kinase inhibitor, wherein the individual has progressed on gemcitabine-based therapy. In some embodiments, the individual has non-metastatic pancreatic cancer. In some embodiments, the individual has primary pancreatic cancer. In some embodiments, the tyrosine kinase inhibitors are vandetanib, erlotinib, or gefitinib.

In some embodiments, there is provided a method of treating pancreatic cancer in an individual in need thereof, comprising administering to the individual (a) an effective amount of a composition comprising nanoparticles comprising taxane and albumin; and (b) an effective amount of a tyrosine kinase inhibitor, and wherein the individual is resistant or refractory to a gemcitabine-based therapy. In some embodiments, the individual has non-metastatic pancreatic cancer. In some embodiments, the individual has primary pancreatic cancer. In some embodiments, the tyrosine kinase inhibitors are vandetanib, erlotinib, or gefitinib.

In some embodiments, there is provided a method of treating pancreatic cancer in an individual in need thereof, comprising administering to the individual (a) an effective amount of a composition comprising nanoparticles comprising taxane and albumin; and (b) an effective amount of a tyrosine kinase inhibitor, and wherein the individual has recurrent pancreatic cancer (for example, the individual develops pancreatic cancer after about any of about 2, 3, 4, 5, 6, 7, 8, 9, 10, 11, 12, 24, or 36 months upon the cessation of a gemcitabine-based therapy). In some embodiments, the individual has non-metastatic pancreatic cancer. In some embodiments, the individual has primary pancreatic cancer. In some embodiments, the tyrosine kinase inhibitors are vandetanib, erlotinib, or gefitinib.

In some embodiments, there is provided a method of treating pancreatic cancer in an individual in need thereof, comprising administering to the individual (a) an effective amount of a composition comprising nanoparticles comprising taxane and albumin; and (b) an effective amount of a tyrosine kinase inhibitor, and wherein a gemcitabine-based therapy has stopped (for example for at least 1, 2, 3, 4, 5, 6, 7, 8, 9, or 10 months) when administering the effective amount of the composition comprising nanoparticles comprising taxane and albumin and the effective amount of the tyrosine kinase inhibitor to the individual. In some embodiments, the individual has non-metastatic pancreatic cancer. In some embodiments, the individual has primary pancreatic cancer. In some embodiments, the tyrosine kinase inhibitors are vandetanib, erlotinib, or gefitinib.

In some embodiments, the other chemotherapeutic agent is a matrix metalloproteinase inhibitor. Suitable matrix metalloproteinase inhibitors include, but are not limited to, marimastat. Thus, in some embodiments, there is provided a method of treating pancreatic cancer in an individual in need thereof, comprising administering to the individual (a) an effective amount of a composition comprising nanoparticles comprising taxane and albumin; and (b) an effective amount of a matrix metalloproteinase inhibitor, wherein the individual has progressed on gemcitabine-based therapy. In some embodiments, the individual has non-metastatic pancreatic cancer. In some embodiments, the individual has primary pancreatic cancer. In some embodiments, the matrix metalloproteinase inhibitor is marimastat.

In some embodiments, there is provided a method of treating pancreatic cancer in an individual in need thereof, comprising administering to the individual (a) an effective amount of a composition comprising nanoparticles comprising taxane and albumin; and (b) an effective amount of a matrix metalloproteinase inhibitor, wherein the individual is resistant or refractory to a gemcitabine-based therapy. In some embodiments, the individual has non-metastatic pancreatic cancer. In some embodiments, the individual has primary pancreatic cancer. In some embodiments, the matrix metalloproteinase inhibitor is marimastat.

In some embodiments, there is provided a method of treating pancreatic cancer in an individual in need thereof, comprising administering to the individual (a) an effective amount of a composition comprising nanoparticles comprising taxane and albumin; and (b) an effective amount of a matrix metalloproteinase inhibitor, wherein the individual has recurrent pancreatic cancer (for example, the individual develops pancreatic cancer after about any of about 2, 3, 4, 5, 6, 7, 8, 9, 10, 11, 12, 24, or 36 months upon the cessation of a gemcitabine-based therapy). In some embodiments, the individual has non-metastatic pancreatic cancer. In some embodiments, the individual has primary pancreatic cancer. In some embodiments, the matrix metalloproteinase inhibitor is marimastat.

In some embodiments, there is provided a method of treating pancreatic cancer in an individual in need thereof, comprising administering to the individual (a) an effective amount of a composition comprising nanoparticles comprising taxane and albumin; and (b) an effective amount of a matrix metalloproteinase inhibitor, wherein a gemcitabine-based therapy has stopped (for example for at least 1, 2, 3, 4, 5, 6, 7, 8, 9, or 10 months) when administering the effective amount of the composition comprising nanoparticles comprising taxane and albumin and the effective amount of the matrix metalloproteinase inhibitor to the individual. In some embodiments, the individual has non-metastatic pancreatic cancer. In some embodiments, the individual has primary pancreatic cancer. In some embodiments, the matrix metalloproteinase inhibitor is marimastat.

In some embodiments, the other chemotherapeutic agent is a topoisomerase inhibitor. Suitable topoisomerase inhibitors include, but are not limited to, irinotecan (e.g., CAMTOSAR®). Thus, in some embodiments, there is provided a method of treating pancreatic cancer in an individual in need thereof, comprising administering to the individual (a) an effective amount of a composition comprising nanoparticles comprising taxane and albumin; and (b) an effective amount of a topoisomerase inhibitor, wherein the individual has progressed on gemcitabine-based therapy. In some embodiments, the individual has non-metastatic pancreatic cancer. In some embodiments, the individual has primary pancreatic cancer. In some embodiments, the topoisomerase inhibitor is irinotecan.

In some embodiments, there is provided a method of treating pancreatic cancer in an individual in need thereof, comprising administering to the individual (a) an effective amount of a composition comprising nanoparticles comprising taxane and albumin; and (b) an effective amount of a topoisomerase inhibitor, wherein the individual is resistant or refractory to a gemcitabine-based therapy. In some embodiments, the individual has non-metastatic pancreatic cancer. In some embodiments, the individual has primary pancreatic cancer. In some embodiments, the topoisomerase inhibitor is irinotecan.

In some embodiments, there is provided a method of treating pancreatic cancer in an individual in need thereof, comprising administering to the individual (a) an effective amount of a composition comprising nanoparticles comprising taxane and albumin; and (b) an effective amount of a topoisomerase inhibitor, wherein the individual has recurrent pancreatic cancer (for example, the individual develops pancreatic cancer after about any of about 2, 3, 4, 5, 6, 7, 8, 9, 10, 11, 12, 24, or 36 months upon the cessation of a gemcitabine-based therapy). In some embodiments, the individual has non-metastatic pancreatic cancer. In some embodiments, the individual has primary pancreatic cancer. In some embodiments, the topoisomerase inhibitor is irinotecan.

In some embodiments, there is provided a method of treating pancreatic cancer in an individual in need thereof, comprising administering to the individual (a) an effective amount of a composition comprising nanoparticles comprising taxane and albumin; and (b) an effective amount of a topoisomerase inhibitor, wherein a gemcitabine-based therapy has stopped (for example for at least 1, 2, 3, 4, 5, 6, 7, 8, 9, or 10 months) when administering the effective amount of the composition comprising nanoparticles comprising taxane and albumin and the effective amount of the topoisomerase inhibitor to the individual. In some embodiments, the individual has non-metastatic pancreatic cancer. In some embodiments, the individual has primary pancreatic cancer. In some embodiments, the topoisomerase inhibitor is irinotecan.

In some embodiments, the other chemotherapeutic agent is a proteasome inhibitor. Suitable proteasome inhibitors include, but are not limited to, bortezomib (e.g., VELCADE®). Thus, in some embodiments, there is provided a method of treating pancreatic cancer in an individual in need thereof, comprising administering to the individual (a) an effective amount of a composition comprising nanoparticles comprising taxane and albumin; and (b) an effective amount of a proteasome inhibitor, wherein the individual has progressed on gemcitabine-based therapy. In some embodiments, the individual has non-metastatic pancreatic cancer. In some embodiments, the individual has primary pancreatic cancer. In some embodiments, the proteasome inhibitor is bortezomib.

In some embodiments, there is provided a method of treating pancreatic cancer in an individual in need thereof, comprising administering to the individual (a) an effective amount of a composition comprising nanoparticles comprising taxane and albumin; and (b) an effective amount of a proteasome inhibitor, wherein the individual is resistant or refractory to a gemcitabine-based therapy. In some embodiments, the individual has non-metastatic pancreatic cancer. In some embodiments, the individual has primary pancreatic cancer. In some embodiments, the proteasome inhibitor is bortezomib.

In some embodiments, there is provided a method of treating pancreatic cancer in an individual in need thereof, comprising administering to the individual (a) an effective amount of a composition comprising nanoparticles comprising taxane and albumin; and (b) an effective amount of a proteasome inhibitor, wherein the individual has recurrent pancreatic cancer (for example, the individual develops pancreatic cancer after about any of about 2, 3, 4, 5, 6, 7, 8, 9, 10, 11, 12, 24, or 36 months upon the cessation of a gemcitabine-based therapy). In some embodiments, the individual has non-metastatic pancreatic cancer. In some embodiments, the individual has primary pancreatic cancer. In some embodiments, the proteasome inhibitor is bortezomib.

In some embodiments, there is provided a method of treating pancreatic cancer in an individual in need thereof, comprising administering to the individual (a) an effective amount of a composition comprising nanoparticles comprising taxane and albumin; and (b) an effective amount of a proteasome inhibitor, wherein a gemcitabine-based therapy has stopped (for example for at least 1, 2, 3, 4, 5, 6, 7, 8, 9, or 10 months) when administering the effective amount of the composition comprising nanoparticles comprising taxane and albumin and the effective amount of the proteasome inhibitor to the individual. In some embodiments, the individual has non-metastatic pancreatic cancer. In some embodiments, the individual has primary pancreatic cancer. In some embodiments, the proteasome inhibitor is bortezomib.

In some embodiments, the other chemotherapeutic agent is a platinum-based agent. Suitable platinum-based agents include, but are not limited to carboplatin, cisplatin, oxaliplatin (e.g., ELOXATIN®), and satraplatin. Thus, in some embodiments, there is provided a method of treating pancreatic cancer in an individual in need thereof, comprising administering to the individual (a) an effective amount of a composition comprising nanoparticles comprising taxane and albumin; and (b) an effective amount of a platinum-based agent, and wherein the individual has progressed on gemcitabine-based therapy. In some embodiments, the individual has non-metastatic pancreatic cancer. In some embodiments, the individual has primary pancreatic cancer. In some embodiments, the platinum-based agent is carboplatin, cisplatin, oxaliplatin, or satraplatin. In some embodiments, the platinum-based agent is not carboplatin, cisplatin, oxaliplatin, or satraplatin.

In some embodiments, there is provided a method of treating pancreatic cancer in an individual in need thereof, comprising administering to the individual (a) an effective amount of a composition comprising nanoparticles comprising taxane and albumin; and (b) an effective amount of a platinum-based agent, and wherein the individual is resistant or refractory to a gemcitabine-based therapy. In some embodiments, the individual has non-metastatic pancreatic cancer. In some embodiments, the individual has primary pancreatic cancer. In some embodiments, the platinum-based agent is carboplatin, cisplatin, oxaliplatin, or satraplatin. In some embodiments, the platinum-based agent is not carboplatin, cisplatin, oxaliplatin, or satraplatin.

In some embodiments, there is provided a method of treating pancreatic cancer in an individual in need thereof, comprising administering to the individual (a) an effective amount of a composition comprising nanoparticles comprising taxane and albumin; and (b) an effective amount of a platinum-based agent, and wherein the individual has recurrent pancreatic cancer (for example, the individual develops pancreatic cancer after about any of about 2, 3, 4, 5, 6, 7, 8, 9, 10, 11, 12, 24, or 36 months upon the cessation of a gemcitabine-based therapy). In some embodiments, the individual has non-metastatic pancreatic cancer. In some embodiments, the individual has primary pancreatic cancer. In some embodiments, the platinum-based agent is carboplatin, cisplatin, oxaliplatin, or satraplatin. In some embodiments, the platinum-based agent is not carboplatin, cisplatin, oxaliplatin, or satraplatin.

In some embodiments, there is provided a method of treating pancreatic cancer in an individual in need thereof, comprising administering to the individual (a) an effective amount of a composition comprising nanoparticles comprising taxane and albumin; and (b) an effective amount of a platinum-based agent, and wherein a gemcitabine-based therapy has stopped (for example for at least 1, 2, 3, 4, 5, 6, 7, 8, 9, or 10 months) when administering the effective amount of the composition comprising nanoparticles comprising taxane and albumin and the effective amount of the platinum-based agent to the individual. In some embodiments, the individual has non-metastatic pancreatic cancer. In some embodiments, the individual has primary pancreatic cancer. In some embodiments, the platinum-based agent is carboplatin, cisplatin, oxaliplatin, or satraplatin. In some embodiments, the platinum-based agent is not carboplatin, cisplatin, oxaliplatin, or satraplatin.

In some embodiments, the other chemotherapeutic agent is a therapeutic antibody. Suitable therapeutic antibodies include, but are not limited to, anti-VEGF antibody (such as bevacizumab (e.g., AVASTIN®)) and anti-HER2 antibody (such as cetuximab (e.g., ERBITUX®)). Thus, in some embodiments, there is provided a method of treating pancreatic cancer in an individual in need thereof, comprising administering to the individual (a) an effective amount of a composition comprising nanoparticles comprising taxane and albumin; and (b) an effective amount of a therapeutic antibody, wherein the individual has progressed on gemcitabine-based therapy. In some embodiments, the individual has non-metastatic pancreatic cancer. In some embodiments, the individual has primary pancreatic cancer. In some embodiments, the therapeutic antibody is bevacizumab or cetuximab.

in some embodiments, there is provided a method of treating pancreatic cancer in an individual in need thereof, comprising administering to the individual (a) an effective amount of a composition comprising nanoparticles comprising taxane and albumin; and (b) an effective amount of a therapeutic antibody, wherein the individual is resistant or refractory to a gemcitabine-based therapy. In some embodiments, the individual has non-metastatic pancreatic cancer. In some embodiments, the individual has primary pancreatic cancer. In some embodiments, the therapeutic antibody is bevacizumab or cetuximab.

In some embodiments, there is provided a method of treating pancreatic cancer in an individual in need thereof, comprising administering to the individual (a) an effective amount of a composition comprising nanoparticles comprising taxane and albumin; and (b) an effective amount of a therapeutic antibody, wherein the individual has recurrent pancreatic cancer (for example, the individual develops pancreatic cancer after about any of about 2, 3, 4, 5, 6, 7, 8, 9, 10, 11, 12, 24, or 36 months upon the cessation of a gemcitabine-based therapy). In some embodiments, the individual has non-metastatic pancreatic cancer. In some embodiments, the individual has primary pancreatic cancer. In some embodiments, the therapeutic antibody is bevacizumab or cetuximab.

In some embodiments, there is provided a method of treating pancreatic cancer in an individual in need thereof, comprising administering to the individual (a) an effective amount of a composition comprising nanoparticles comprising taxane and albumin; and (b) an effective amount of a therapeutic antibody, wherein a gemcitabine-based therapy has stopped (for example for at least 1, 2, 3, 4, 5, 6, 7, 8, 9, or 10 months) when administering the effective amount of the composition comprising nanoparticles comprising taxane and albumin and the effective amount of the therapeutic antibody, to the individual. In some embodiments, the individual has non-metastatic pancreatic cancer. In some embodiments, the individual has primary pancreatic cancer. In some embodiments, the therapeutic antibody is bevacizumab or cetuximab.

In some embodiments, the other chemotherapeutic agent is a farnesyltransferase inhibitor. Suitable farnesyltransferase inhibitors include, but are not limited to, tipifarnib (e.g., ZARNESTRA™). Thus, in some embodiments, there is provided a method of treating pancreatic cancer in an individual in need thereof, comprising administering to the individual (a) an effective amount of a composition comprising nanoparticles comprising taxane and albumin; and (b) an effective amount of a farnesyltransferase inhibitor, wherein the individual has progressed on gemcitabine-based therapy. In some embodiments, the individual has non-metastatic pancreatic cancer. In some embodiments, the individual has primary pancreatic cancer. In some embodiments, the farnesyltransferase inhibitor is tipifarnib.

In some embodiments, there is provided a method of treating pancreatic cancer in an individual in need thereof, comprising administering to the individual (a) an effective amount of a composition comprising nanoparticles comprising taxane and albumin; and (b) an effective amount of a farnesyltransferase inhibitor, wherein the individual is resistant or refractory to a gemcitabine-based therapy. In some embodiments, the individual has non-metastatic pancreatic cancer. In some embodiments, the individual has primary pancreatic cancer. In some embodiments, the farnesyltransferase inhibitor is tipifarnib.

In some embodiments, there is provided a method of treating pancreatic cancer in an individual in need thereof, comprising administering to the individual (a) an effective amount of a composition comprising nanoparticles comprising taxane and albumin; and (b) an effective amount of a farnesyltransferase inhibitor, wherein the individual has recurrent pancreatic cancer (for example, the individual develops pancreatic cancer after about any of about 2, 3, 4, 5, 6, 7, 8, 9, 10, 11, 12, 24, or 36 months upon the cessation of a gemcitabine-based therapy). In some embodiments, the individual has non-metastatic pancreatic cancer. In some embodiments, the individual has primary pancreatic cancer. In some embodiments, the farnesyltransferase inhibitor is tipifarnib.

In some embodiments, there is provided a method of treating pancreatic cancer in an individual in need thereof, comprising administering to the individual (a) an effective amount of a composition comprising nanoparticles comprising taxane and albumin; and (b) an effective amount of a farnesyltransferase inhibitor, wherein a gemcitabine-based therapy has stopped (for example for at least 1, 2, 3, 4, 5, 6, 7, 8, 9, or 10 months) when administering the effective amount of the composition comprising nanoparticles comprising taxane and albumin and the effective amount of the farnesyltransferase inhibitor to the individual. In some embodiments, the individual has non-metastatic pancreatic cancer. In some embodiments, the individual has primary pancreatic cancer. In some embodiments, the farnesyltransferase inhibitor is tipifarnib.

In some embodiments, the other chemotherapeutic agent is an inhibitor of the hedgehog signaling pathway (a hedgehog inhibitor). Suitable hedgehog inhibitors include, but are not limited to, vismodegib and cyclopamide. Thus, in some embodiments, there is provided a method of treating pancreatic cancer in an individual in need thereof, comprising administering to the individual (a) an effective amount of a composition comprising nanoparticles comprising taxane and albumin; and (b) an effective amount of a hedgehog inhibitor, wherein the individual has progressed on gemcitabine-based therapy. In some embodiments, the individual has non-metastatic pancreatic cancer. In some embodiments, the individual has primary pancreatic cancer. In some embodiments, the hedgehog inhibitor is vismodegib. In some embodiments, the hedgehog inhibitor is cyclopamide.

In some embodiments, there is provided a method of treating pancreatic cancer in an individual in need thereof, comprising administering to the individual (a) an effective amount of a composition comprising nanoparticles comprising taxane and albumin; and (b) an effective amount of a hedgehog inhibitor, wherein the individual is resistant or refractory to a gemcitabine-based therapy. In some embodiments, the individual has non-metastatic pancreatic cancer. In some embodiments, the individual has primary pancreatic cancer. In some embodiments, the hedgehog inhibitor is vismodegib. In some embodiments, the hedgehog inhibitor is cyclopamide.

In some embodiments, there is provided a method of treating pancreatic cancer in an individual in need thereof, comprising administering to the individual (a) an effective amount of a composition comprising nanoparticles comprising taxane and albumin; and (b) an effective amount of a hedgehog inhibitor, wherein the individual has recurrent pancreatic cancer (for example, the individual develops pancreatic cancer after about any of about 2, 3, 4, 5, 6, 7, 8, 9, 10, 11, 12, 24, or 36 months upon the cessation of a gemcitabine-based therapy). In some embodiments, the individual has non-metastatic pancreatic cancer. In some embodiments, the individual has primary pancreatic cancer. In some embodiments, the hedgehog inhibitor is vismodegib. In some embodiments, the hedgehog inhibitor is cyclopamide.

In some embodiments, there is provided a method of treating pancreatic cancer in an individual in need thereof, comprising administering to the individual (a) an effective amount of a composition comprising nanoparticles comprising taxane and albumin; and (b) an effective amount of a hedgehog inhibitor, wherein a gemcitabine-based therapy has stopped (for example for at least 1, 2, 3, 4, 5, 6, 7, 8, 9, or 10 months) when administering the effective amount of the composition comprising nanoparticles comprising taxane and albumin and the effective amount of the hedgehog inhibitor to the individual. In some embodiments, the individual has non-metastatic pancreatic cancer. In some embodiments, the individual has primary pancreatic cancer. In some embodiments, the hedgehog inhibitor is vismodegib. In some embodiments, the hedgehog inhibitor is cyclopamide.

In some embodiments, the other chemotherapeutic agent is an anti-angiogenic agent. The anti-angiogenic agent can be naturally occurring or non-naturally occurring. In some embodiments, the chemotherapeutic agent is a synthetic antiangiogenic peptide. In some embodiments, the antiangiogenic agent is other than an anti-VEGF antibody (such as bevacizumab (e.g., AVASTIN®)) Thus, in some embodiments, there is provided a method of treating pancreatic cancer in an individual in need thereof, comprising administering to the individual (a) an effective amount of a composition comprising nanoparticles comprising taxane and albumin; and (b) an effective amount of an anti-angiogenic agent, wherein the individual has progressed on gemcitabine-based therapy. In some embodiments, the individual has non-metastatic pancreatic cancer. In some embodiments, the individual has primary pancreatic cancer.

In some embodiments, there is provided a method of treating pancreatic cancer in an individual in need thereof, comprising administering to the individual (a) an effective amount of a composition comprising nanoparticles comprising taxane and albumin; and (b) an effective amount of an anti-angiogenic agent, wherein the individual is resistant or refractory to a gemcitabine-based therapy. In some embodiments, the individual has non-metastatic pancreatic cancer. In some embodiments, the individual has primary pancreatic cancer.

In some embodiments, there is provided a method of treating pancreatic cancer in an individual in need thereof, comprising administering to the individual (a) an effective amount of a composition comprising nanoparticles comprising taxane and albumin; and (b) an effective amount of an anti-angiogenic agent, wherein the individual has recurrent pancreatic cancer (for example, the individual develops pancreatic cancer after about any of about 2, 3, 4, 5, 6, 7, 8, 9, 10, 11, 12, 24, or 36 months upon the cessation of a gemcitabine-based therapy). In some embodiments, the individual has non-metastatic pancreatic cancer. In some embodiments, the individual has primary pancreatic cancer.

In some embodiments, there is provided a method of treating pancreatic cancer in an individual in need thereof, comprising administering to the individual (a) an effective amount of a composition comprising nanoparticles comprising taxane and albumin; and (b) an effective amount of an anti-angiogenic agent, wherein a gemcitabine-based therapy has stopped (for example for at least 1, 2, 3, 4, 5, 6, 7, 8, 9, or 10 months) when administering the effective amount of the composition comprising nanoparticles comprising taxane and albumin and the effective amount of the anti-angiogenic agent to the individual. In some embodiments, the individual has non-metastatic pancreatic cancer. In some embodiments, the individual has primary pancreatic cancer.

In some embodiments, the other chemotherapeutic agent is a macrolide such as rapamycin. Thus, in some embodiments, there is provided a method of treating pancreatic cancer in an individual in need thereof, comprising administering to the individual (a) an effective amount of a composition comprising nanoparticles comprising taxane and albumin; and (b) an effective amount of a macrolide, wherein the individual has progressed on gemcitabine-based therapy. In some embodiments, the individual has non-metastatic pancreatic cancer. In some embodiments, the individual has primary pancreatic cancer. In some embodiments, the macrolide is rapamycin.

In some embodiments, there is provided a method of treating pancreatic cancer in an individual in need thereof, comprising administering to the individual (a) an effective amount of a composition comprising nanoparticles comprising taxane and albumin; and (b) an effective amount of a macrolide, wherein the individual is resistant or refractory to a gemcitabine-based therapy. In some embodiments, the individual has non-metastatic pancreatic cancer. In some embodiments, the individual has primary pancreatic cancer. In some embodiments, the macrolide is rapamycin.

In some embodiments, there is provided a method of treating pancreatic cancer in an individual in need thereof, comprising administering to the individual (a) an effective amount of a composition comprising nanoparticles comprising taxane and albumin; and (b) an effective amount of a macrolide, wherein the individual has recurrent pancreatic cancer (for example, the individual develops pancreatic cancer after about any of about 2, 3, 4, 5, 6, 7, 8, 9, 10, 11, 12, 24, or 36 months upon the cessation of a gemcitabine-based therapy). In some embodiments, the individual has non-metastatic pancreatic cancer. In some embodiments, the individual has primary pancreatic cancer. In some embodiments, the macrolide is rapamycin.

In some embodiments, there is provided a method of treating pancreatic cancer in an individual in need thereof, comprising administering to the individual (a) an effective amount of a composition comprising nanoparticles comprising taxane and albumin; and (b) an effective amount of a macrolide, wherein a gemcitabine-based therapy has stopped (for example for at least 1, 2, 3, 4, 5, 6, 7, 8, 9, or 10 months) when administering the effective amount of the composition comprising nanoparticles comprising taxane and albumin and the effective amount of the macrolide to the individual. In some embodiments, the individual has non-metastatic pancreatic cancer. In some embodiments, the individual has primary pancreatic cancer. In some embodiments, the macrolide is rapamycin.

The other agents described herein can be the agents themselves, pharmaceutically acceptable salts thereof, and pharmaceutically acceptable esters thereof, as well as stereoisomers, enantiomers, racemic mixtures, and the like. The other agent or agents as described can be administered as well as a pharmaceutical composition containing the agent(s), wherein the pharmaceutical composition comprises a pharmaceutically acceptable carrier vehicle, or the like.

In some embodiments, two or more chemotherapeutic agents are administered in addition to the taxane in the nanoparticle composition. These two or more chemotherapeutic agents may (but not necessarily) belong to different classes of chemotherapeutic agents. Examples of these combinations are provided herein. Other combinations are also contemplated.

Thus, for example, in some embodiments, there is provided a method of treating pancreatic cancer in an individual, comprising administering to the individual a) an effective amount of a composition comprising nanoparticles comprising a taxane and an albumin, b) an effective amount of 5-fluorouracil, and c) an effective amount of erlotinib, wherein the individual has progressed on gemcitabine-based therapy. In some embodiments, the individual has non-metastatic pancreatic cancer. In some embodiments, the individual has primary pancreatic cancer. In some embodiments, the individual is resistant or refractory to the prior therapy. In some embodiments, the individual has recurrent pancreatic cancer (for example, the individual develops pancreatic cancer after about any of about 2, 3, 4, 5, 6, 7, 8, 9, 10, 11, 12, 24, or 36 months upon the cessation of the prior therapy). In some embodiments, the prior therapy has stopped (for example for at least 1, 2, 3, 4, 5, 6, 7, 8, 9, or 10 months) when initiating the methods of the present invention.

In some embodiments, there is provided a method of treating pancreatic cancer in an individual in need thereof, comprising administering to the individual (a) an effective amount of a composition comprising nanoparticles comprising a taxane (such as paclitaxel) and an albumin, and (b) an effective amount of a VEGFR/EFGR inhibitor.

In some embodiments, there is provided a method of treating pancreatic cancer in an individual in need thereof, comprising administering to the individual (a) an effective amount of a composition comprising nanoparticles comprising a taxane (such as paclitaxel) and an albumin, and (b) an effective amount of vandetanib.

In some embodiments, there is provided a method of treating pancreatic cancer in an individual in need thereof, comprising administering to the individual (a) an effective amount of a composition comprising nanoparticles comprising a taxane (such as paclitaxel) coated with albumin, and (b) an effective amount of a VEGFR/EFGR inhibitor.

In some embodiments, there is provided a method of treating pancreatic cancer in an individual in need thereof, comprising administering to the individual (a) an effective amount of a composition comprising nanoparticles comprising a taxane (such as paclitaxel) coated with albumin, and (b) an effective amount of vandetanib.

In some embodiments, there is provided a method of treating pancreatic cancer in an individual in need thereof, comprising administering to the individual (a) an effective amount of a composition comprising nanoparticles comprising a taxane (such as paclitaxel) coated with albumin, and (b) an effective amount of a VEGFR/EFGR inhibitor; wherein the nanoparticles of the composition have an average diameter of no greater than about 200 nm (such as less than about 200 nm).

In some embodiments, there is provided a method of treating pancreatic cancer in an individual in need thereof, comprising administering to the individual (a) an effective amount of a composition comprising nanoparticles comprising a taxane (such as paclitaxel) coated with albumin, and (b) an effective amount of vandetanib; wherein the nanoparticles of the composition have an average diameter of no greater than about 200 nm (such as less than about 200 nm).

In some embodiments, there is provided a method of treating pancreatic cancer in an individual in need thereof, comprising administering to the individual (a) an effective amount of ABRAXANE®, and (b) an effective amount of a VEGFR/EFGR inhibitor. In some embodiments, there is provided a method of treating pancreatic cancer in an individual in need thereof, comprising (a) intravenously administering to the individual an effective amount of ABRAXANE®, and (b) orally administering to the individual an effective amount of a VEGFR/EFGR inhibitor.

In some embodiments, there is provided a method of treating pancreatic cancer in an individual in need thereof, comprising administering to the individual (a) an effective amount of ABRAXANE®, and (b) an effective amount of vandetanib. In some embodiments, there is provided a method of treating pancreatic cancer in an individual in need thereof, comprising (a) intravenously administering to the individual an effective amount of ABRAXANE®, and (b) orally administering an effective amount of vandetanib.

In some embodiments, there is provided a method of treating pancreatic cancer in an individual in need thereof, comprising administering to the individual (a) an effective amount of ABRAXANE, and (b) an effective amount of vandetanib; wherein the ABRAXANE® is administered (for example weekly or weekly for three out of four weeks) at a dose ranging from about 80 mg/m$^2$ to about 150 mg/m$^2$ (for example about 100 mg/m$^2$) and wherein the vandetanib is administered daily at a dose ranging from about 100 mg to about 300 mg (such as about 300 mg). In some embodiments, there is provided a method of treating pancreatic cancer in an individual in need thereof, comprising (a) intravenously administering to the individual an effective amount of ABRAXANE, and (b) orally administering to the individual an effective amount of vandetanib; wherein the ABRAXANE® is administered (for example weekly or weekly for three out of four weeks) at a dose ranging from about 80 mg/m$^2$ to about 150 mg/m$^2$ (for example about 100 mg/m$^2$) and wherein the vandetanib is administered daily at a dose ranging from about 100 mg to about 300 mg (such as about 300 mg).

In some embodiments, there is provided a method of treating pancreatic cancer in an individual in need thereof, comprising administering to the individual (a) an effective amount of ABRAXANE®, and (b) an effective amount of vandetanib; wherein the ABRAXANE is administered (for example once every three weeks) at a dose of about 200 mg/m$^2$ to about 300 mg/m$^2$ (for example about 260 mg/m$^2$) and wherein the vandetanib is administered daily at a dose ranging from about 100 mg to about 300 mg (for example about 300 mg). In some embodiments, there is provided a method of treating pancreatic cancer in an individual in need thereof, comprising (a) intravenously administering to the individual an effective amount of ABRAXANE®, and (b) orally administering to the individual an effective amount of vandetanib; wherein the ABRAXANE is administered (for example once every three weeks) at a dose of about 200 mg/m$^2$ to about 300 mg/m$^2$ (for example about 260 mg/m$^2$) and wherein the vandetanib is administered daily at a dose ranging from about 100 mg to about 300 mg (for example about 300 mg).

In some embodiments, the nanoparticle composition and the VEGFR/EGFR inhibitor (such as vandetanib) are administered simultaneously or sequentially. In some embodiments, the nanoparticle composition and the VEGFR/EGFR inhibitor (such as vandetanib) are administered concurrently. In some embodiments, at least one (including for example 2, 3, 4, 5, 6, or more) treatment cycles of the treatment comprises the administration of both the nanoparticle composition and the VEGFR/EGFR inhibitor (such as vandetanib).

The combination therapy methods with the nanoparticle composition and the VEGFR/EGFR are useful for treating individuals having pancreatic cancer, including individuals who have been previously treated for pancreatic cancer and individuals who have not been previously treated for pancreatic cancer. In some embodiments, the individual has not previously been treated for pancreatic cancer. In some embodiments, the individual has previously been treated for pancreatic cancer. In some embodiments, the individual has progressed on a prior therapy (such as a gemcitabine-based therapy). In some embodiments, the individual is resistant or refractory to the prior therapy. In some embodiments, the individual is unsuitable to continue with the prior therapy (for example due to failure to respond and/or due to toxicity). In some embodiments, the individual has recurrent pancreatic disease after the prior therapy. In some embodiments, the individual is non-responsive to the prior therapy. In some embodiments, the individual exhibits a less desirable degree of responsiveness to the prior therapy. In some embodiments, the individual exhibits enhanced responsiveness to the prior therapy.

Also provided are pharmaceutical compositions comprising nanoparticles comprising a taxane and an albumin (such as human serum albumin) for use in any of the methods of treating pancreatic cancer described herein.

It is understood that any of the methods of treating pancreatic cancer described herein (such as above section "Methods of Treating pancreatic cancer") apply to and include description of combination therapies. In some embodiments, a lower amount of each pharmaceutically active compound is used as part of a combination therapy compared to the amount generally used for individual therapy. In some embodiments, the same or greater therapeutic benefit is achieved using a combination therapy than by using any of the individual compounds alone. In some embodiments, the same or greater therapeutic benefit is achieved using a smaller amount (e.g., a lower dose or a less frequent dosing schedule) of a pharmaceutically active compound in a combination therapy than the amount generally used for individual therapy. For example, the use of a small amount of pharmaceutically active compound may result in a reduction in the number, severity, frequency, or duration of one or more side-effects associated with the compound.

In some embodiments of the method of any of the above, the method of treating pancreatic cancer in an individual in need thereof comprises administering to the individual an effective amount of a composition comprising nanoparticles comprising a taxane and an albumin, wherein the individual has progressed on gemcitabine-based therapy. In some embodiments, the progression is within less than about 12 months. In some embodiments, the gemcitabine-based therapy further comprises erlotinib. In some embodiments, the gemcitabine-based therapy is monotherapy.

In some embodiments of the method of any of the above, the method of treating pancreatic cancer in an individual in need thereof comprises administering to the individual (a) an effective amount of a composition comprising nanoparticles comprising taxane and albumin; and (b) an effective amount of another agent, wherein the individual has progressed on gemcitabine-based therapy. In some embodiments, the nanoparticle composition and the other agent can be administered simultaneously or sequentially. In some embodiments, the nanoparticle composition and the other agent are administered concurrently. In some embodiments, the other agent is selected from the group consisting of vandetanib, 5-fluororuracil, erlotinib, gefitnib, marimastat, irinotecan, tipifarnib, pemetrexed, exatecan, capecitabine, raltitrexed, cetuximab, bevacizumab, bortezomib, rapamycin, and gemcitabine. In some embodiments, the other agent is vandetanib and the individual has not received previous treatment for pancreatic cancer.

In some embodiments of the method of any of the above, the pancreatic cancer is exocrine pancreatic cancer or endocrine pancreatic cancer. In some embodiments, the exocrine pancreatic cancer is pancreatic ductal carcinoma. In some embodiments, the pancreatic cancer is locally advanced pancreatic cancer, unresectable pancreatic cancer, or metastatic pancreatic ductal carcinoma.

In some embodiments of the method of any of the above, the composition comprising nanoparticles comprising taxane and albumin is administered parenterally. In some embodiments, the composition comprising nanoparticles comprising taxane and albumin is administered intravenously or intraarterially.

In some embodiments of the method of any of the above, the taxane is paclitaxel. In some embodiments, the nanoparticles in the composition have an average diameter of no greater than about 200 nm. In some embodiments, the nanoparticles in the composition have an average diameter of less than about 200 nm. In some embodiments, the taxane in the nanoparticles is coated with albumin.

In some embodiments of the method of any of the above, the individual is human.

In some embodiments of the method of any of the above, the levels of serum CA19-9 (carbohydrate antigen 19-9) in the individual are decreased by at least about 50% in comparison to the levels of serum CA19-9 prior to the treatment.

The dosing regimens for the methods described herein are further provided below.

Dosing and Method of Administering the Nanoparticle Compositions

The dose of the taxane nanoparticle compositions administered to an individual (such as a human) may vary with the particular composition, the mode of administration, and the type of pancreatic cancer being treated. In some embodiments, the amount of the composition is effective to result in an objective response (such as a partial response, a complete response, or stable disease). In some embodiments, the amount of the taxane nanoparticle composition is sufficient to result in a complete response in the individual. In some embodiments, the amount of the taxane nanoparticle composition is sufficient to result in a partial response in the individual. In some embodiments, the amount of the taxane nanoparticle composition is sufficient to result in stable disease (i.e., pancreatic cancer) in the individual. In some embodiments, the amount of the taxane nanoparticle composition administered (for example when administered alone) is sufficient to produce an overall response rate of more than about any of 25%, 30%, 32%, 35%, 36%, 37%, 38%, 39%, 40%, 50%, 60%, 65%, or 70% among a population of individuals treated with the taxane nanoparticle composition. Responses of an individual to the treatment of the methods described herein can be determined, for example, based on RECIST levels.

In some embodiments, the amount of the composition is sufficient to prolong progress-free survival of the individual. In some embodiments, the amount of the composition is sufficient to prolong overall survival of the individual. In some embodiments, the amount of the composition (for example when administered along) is sufficient to produce clinical benefits of more than about any of 25%, 30%, 32%, 35%, 36%, 37%, 38%, 39%, 40%, 50%, 60%, 65%, or 70% among a population of individuals treated with the taxane nanoparticle composition.

In some embodiments, the amount of the composition, first therapy, second therapy, or combination therapy is an amount sufficient to decrease the size of a tumor, decrease the number of cancer cells, or decrease the growth rate of a tumor by at least about any of 10%, 20%, 30%, 40%, 50%, 60%, 70%, 80%, 90%, 95% or 100% compared to the corresponding tumor size, number of pancreatic cancer cells, or tumor growth rate in the same subject prior to treatment or compared to the corresponding activity in other subjects not receiving the treatment. Standard methods can be used to measure the magnitude of this effect, such as in vitro assays with purified enzyme, cell-based assays, animal models, or human testing.

In some embodiments, the amount of the taxane (e.g., paclitaxel) in the composition is below the level that induces a toxicological effect (i.e., an effect above a clinically acceptable level of toxicity) or is at a level where a potential side effect can be controlled or tolerated when the composition is administered to the individual.

In some embodiments, the amount of the composition is close to a maximum tolerated dose (MTD) of the composition following the same dosing regime. In some embodiments, the amount of the composition is more than about any of 80%, 90%, 95%, or 98% of the MTD.

In some embodiments, the amount of a taxane (e.g., paclitaxel) in the composition is included in any of the following ranges: about 0.1 mg to about 500 mg, about 0.1 mg to about 2.5 mg, about 0.5 to about 5 mg, about 5 to about 10 mg, about 10 to about 15 mg, about 15 to about 20 mg, about 20 to about 25 mg, about 20 to about 50 mg, about 25 to about 50 mg, about 50 to about 75 mg, about 50 to about 100 mg, about 75 to about 100 mg, about 100 to about 125 mg, about 125 to about 150 mg, about 150 to about 175 mg, about 175 to about 200 mg, about 200 to about 225 mg, about 225 to about 250 mg, about 250 to about 300 mg, about 300 to about 350 mg, about 350 to about 400 mg, about 400 to about 450 mg, or about 450 to about 500 mg. In some embodiments, the amount of a taxane (e.g., paclitaxel) in the effective amount of the composition (e.g., a unit dosage form) is in the range of about 5 mg to about 500 mg, such as about 30 mg to about 300 mg or about 50 mg to about 200 mg. In some embodiments, the concentration of the taxane (e.g., paclitaxel) in the composition is dilute (about 0.1 mg/ml) or concentrated (about 100 mg/ml), including for example any of about 0.1 to about 50 mg/ml, about 0.1 to about 20 mg/ml, about 1 to about 10 mg/ml, about 2 mg/ml to about 8 mg/ml, about 4 to about 6 mg/ml, or about 5 mg/ml. In some embodiments, the concentration of the taxane (e.g., paclitaxel) is at least about any of 0.5 mg/ml, 1.3 mg/ml, 1.5 mg/ml, 2 mg/ml, 3 mg/ml, 4 mg/ml, 5 mg/ml, 6 mg/ml, 7 mg/ml, 8 mg/ml, 9 mg/ml, 10 mg/ml, 15 mg/ml, 20 mg/ml, 25 mg/ml, 30 mg/ml, 40 mg/ml, or 50 mg/ml.

Exemplary effective amounts of a taxane (e.g., paclitaxel) in the nanoparticle composition include, but are not limited to, at least about any of 25 mg/m$^2$, 30 mg/m$^2$, 50 mg/m$^2$, 60 mg/m$^2$, 75 mg/m$^2$, 80 mg/m$^2$, 90 mg/m$^2$, 100 mg/m$^2$, 120 mg/m$^2$, 125 mg/m$^2$, 150 mg/m$^2$, 160 mg/m$^2$, 175 mg/m$^2$, 180 mg/m$^2$, 200 mg/m$^2$, 210 mg/m$^2$, 220 mg/m$^2$, 250 mg/m$^2$, 260 mg/m$^2$, 300 mg/m$^2$, 350 mg/m$^2$, 400 mg/m$^2$, 500 mg/m$^2$, 540 mg/m$^2$, 750 mg/m$^2$, 1000 mg/m$^2$, or 1080 mg/m$^2$ of a taxane (e.g., paclitaxel). In various embodiments, the composition includes less than about any of 350 mg/m$^2$, 300 mg/m$^2$, 250 mg/m$^2$, 200 mg/m$^2$, 150 mg/m$^2$, 120 mg/m$^2$, 100 mg/m$^2$, 90 mg/m$^2$, 50 mg/m$^2$, or 30 mg/m$^2$ of a taxane (e.g., paclitaxel). In some embodiments, the amount of the taxane (e.g., paclitaxel) per administration is less than about any of 25 mg/m$^2$, 22 mg/m$^2$, 20 mg/m$^2$, 18 mg/m$^2$, 15 mg/m$^2$, 14 mg/m$^2$, 13 mg/m$^2$, 12 mg/m$^2$, 11 mg/m$^2$, 10 mg/m$^2$, 9 mg/m$^2$, 8 mg/m$^2$, 7 mg/m$^2$, 6 mg/m$^2$, 5 mg/m$^2$, 4 mg/m$^2$, 3 mg/m$^2$, 2 mg/m$^2$, or 1 mg/m$^2$. In some embodiments, the effective amount of a taxane (e.g., paclitaxel) in the composition is included in any of the following ranges: about 1 to about 5 mg/m$^2$, about 5 to about 10 mg/m$^2$, about 10 to about 25 mg/m$^2$, about 25 to about 50 mg/m$^2$, about 50 to about 75 mg/m$^2$, about 75 to about 100 mg/m$^2$, about 100 to about 125 mg/m$^2$, about 125 to about 150 mg/m$^2$, about 150 to about 175 mg/m$^2$, about 175 to about 200 mg/m$^2$, about 200 to about 225 mg/m$^2$, about 225 to about 250 mg/m$^2$, about 250 to about 300 mg/m$^2$, about 300 to about 350 mg/m$^2$, or about 350 to about 400 mg/m$^2$. In some embodiments, the effective amount of a taxane (e.g., paclitaxel) in the composition is about 5 to about 300 mg/m$^2$, such as about 100 to about 150 mg/m$^2$, about 120 mg/m$^2$, about 130 mg/m$^2$, or about 140 mg/m$^2$. In some embodiments, the effective amount of a taxane (e.g., paclitaxel) in the composition is about 100 mg/m$^2$.

In some embodiments of any of the above aspects, the effective amount of a taxane (e.g., paclitaxel) in the composition includes at least about any of 1 mg/kg, 2.5 mg/kg, 3.5 mg/kg, 5 mg/kg, 6.5 mg/kg, 7.5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 55 mg/kg, or 60 mg/kg. In various embodiments, the effective amount of a taxane (e.g., paclitaxel) in the composition includes less than about any of 350 mg/kg, 300 mg/kg, 250 mg/kg, 200 mg/kg, 150 mg/kg, 100 mg/kg, 50 mg/kg, 25 mg/kg, 20 mg/kg, 10 mg/kg, 7.5 mg/kg, 6.5 mg/kg, 5 mg/kg, 3.5 mg/kg, 2.5 mg/kg, or 1 mg/kg of a taxane (e.g., paclitaxel).

In some embodiments, the effective amount of paclitaxel in the composition is at least about any of 2 mg/kg, 2.5 mg/kg, 2.7 mg/kg, 5 mg/kg, 6.5 mg/kg, 7.5 mg/kg, or 10 mg/kg administered on days 1, 8, and 15 on a 28-day cycle. In some embodiments, the effective amount of paclitaxel in the composition is about 2.7 mg/kg administered on days 1, 8, and 15 on a 28-day cycle. In some embodiments, the composition is administered intravenously over 30 minutes.

Exemplary dosing frequencies for the administration of the nanoparticle compositions include, but are not limited to, daily, every two days, every three days, every four days, every five days, every six days, weekly without break, three out of four weeks, once every three weeks, once every two weeks, or two out of three weeks. In some embodiments, the composition is administered about once every 2 weeks, once every 3 weeks, once every 4 weeks, once every 6 weeks, or once every 8 weeks. In some embodiments, the composition is administered at least about any of 1×, 2×, 3×, 4×, 5×, 6×, or 7× (i.e., daily) a week. In some embodiments, the intervals between each administration are less than about any of 6 months, 3 months, 1 month, 28 days, 20 days, 15, days, 14 days, 13 days, 12 days, 11 days, 10 days, 9 days, 8 days, 7 days, 6 days, 5 days, 4 days, 3 days, 2 days, or 1 day. In some embodiments, the intervals between each administration are more than about any of 1 month, 2 months, 3 months, 4 months, 5 months, 6 months, 8 months, or 12 months. In some embodiments, there is no break in the dosing schedule. In some embodiments, the interval between each administration is no more than about a week.

In some embodiments, the dosing frequency is once every two days for one time, two times, three times, four times, five times, six times, seven times, eight times, nine times, ten times, and eleven times. In some embodiments, the dosing frequency is once every two days for five times. In some embodiments, the taxane (e.g., paclitaxel) is administered over a period of at least ten days, wherein the interval between each administration is no more than about two days, and wherein the dose of the taxane (e.g., paclitaxel) at each administration is about 0.25 mg/m$^2$ to about 250 mg/m$^2$, about 0.25 mg/m$^2$ to about 150 mg/m$^2$, about 0.25 mg/m$^2$ to about 75 mg/m$^2$, such as about 0.25 mg/m$^2$ to about 25 mg/m$^2$, or about 25 mg/m$^2$ to about 50 mg/m$^2$.

In some embodiments, the taxane (e.g., paclitaxel) is administered on days 1, 8, and 15 on a 28-day cycle, wherein the dose of the taxane (e.g., paclitaxel) at each administration is about 100 mg/m$^2$, 125 mg/m$^2$, 150 mg/m$^2$, 175 mg/m$^2$, or 200 mg/m$^2$. In some embodiments, the taxane (e.g., paclitaxel) is administered intravenously over 30 minutes on days 1, 8, and 15 on a 28-day cycle, wherein the dose of the taxane (e.g., paclitaxel) at each administration is about 100 mg/m$^2$, 125 mg/m$^2$, 150 mg/m$^2$, 175 mg/m$^2$, or 200 mg/m$^2$. In some embodiments, the taxane is paclitaxel.

The administration of the composition can be extended over an extended period of time, such as from about a month up to about seven years. In some embodiments, the composition is administered over a period of at least about any of 2, 3, 4, 5, 6, 7, 8, 9, 10, 11, 12, 18, 24, 30, 36, 48, 60, 72, or 84 months.

In some embodiments, the dosage of a taxane (e.g., paclitaxel) in a nanoparticle composition can be in the range of 5-400 mg/m$^2$ when given on a 3 week schedule, or 5-250 mg/m$^2$ (such as 80-150 mg/m$^2$, for example 100-120 mg/m$^2$) when given on a weekly schedule. For example, the amount of a taxane (e.g., paclitaxel) is about 60 to about 300 mg/m$^2$ (e.g., about 260 mg/m$^2$) on a four week schedule.

Other exemplary dosing schedules for the administration of the nanoparticle composition (e.g., paclitaxel/albumin nanoparticle composition) include, but are not limited to, 100 mg/m$^2$, weekly, without break; 75 mg/m$^2$ weekly, 3 out of 4 weeks; 100 mg/m$^2$, weekly, 3 out of 4 weeks; 125 mg/m$^2$, weekly, 3 out of 4 weeks; 125 mg/m$^2$, weekly, 2 out of 3 weeks; 130 mg/m$^2$, weekly, without break; 175 mg/m$^2$, once every 2 weeks; 260 mg/m$^2$, once every 2 weeks; 260 mg/m$^2$, once every 3 weeks; 180-300 mg/m$^2$, every three weeks; 60-175 mg/m$^2$, weekly, without break; 20-150 mg/m$^2$ twice a week; and 150-250 mg/m$^2$ twice a week. The dosing frequency of the composition may be adjusted over the course of the treatment based on the judgment of the administering physician.

In some embodiments, the individual is treated for at least about any of one, two, three, four, five, six, seven, eight, nine, or ten treatment cycles.

The compositions described herein allow infusion of the composition to an individual over an infusion time that is shorter than about 24 hours. For example, in some embodiments, the composition is administered over an infusion period of less than about any of 24 hours, 12 hours, 8 hours, 5 hours, 3 hours, 2 hours, 1 hour, 30 minutes, 20 minutes, or 10 minutes. In some embodiments, the composition is administered over an infusion period of about 30 minutes.

Other exemplary dose of the taxane (in some embodiments paclitaxel) in the nanoparticle composition include, but is not limited to, about any of 50 mg/m$^2$, 60 mg/m$^2$, 75 mg/m$^2$, 80 mg/m$^2$, 90 mg/m$^2$, 100 mg/m$^2$, 120 mg/m$^2$, 160 mg/m$^2$, 175 mg/m$^2$, 200 mg/m$^2$, 210 mg/m$^2$, 220 mg/mrn$^2$, 260 mg/m$^2$, and 300 mg/m$^2$. For example, the dosage of paclitaxel in a nanoparticle composition can be in the range of about 100-400 mg/m$^2$ when given on a 3 week schedule, or about 50-250 mg/m$^2$ when given on a weekly schedule.

The nanoparticle compositions can be administered to an individual (such as human) via various routes, including, for example, intravenous, intra-arterial, intraperitoneal, intrapulmonary, oral, inhalation, intravesicular, intramuscular, intra-tracheal, subcutaneous, intraocular, intrathecal, transmucosal, and transdermal. In some embodiments, sustained continuous release formulation of the composition may be used. In some embodiments, the composition is administered intravenously. In some embodiments, the composition is administered intraarterially. In some embodiments, the composition is administered intraperitoneally.

Modes of Administration of Combination Therapies

The dosing regimens described in the section above apply to both monotherapy and combination therapy settings. The modes of administration for combination therapy methods are further described below.

In some embodiments, the nanoparticle composition and the other agent (including the specific chemotherapeutic agents described herein) are administered simultaneously. When the drugs are administered simultaneously, the drug in the nanoparticles and the other agent may be contained in the same composition (e.g., a composition comprising both the nanoparticles and the other agent) or in separate compositions (e.g., the nanoparticles are contained in one composition and the other agent is contained in another composition).

In some embodiments, the nanoparticle composition and the other agent are administered sequentially. Either the nanoparticle composition or the other agent may be administered first. The nanoparticle composition and the other agent are contained in separate compositions, which may be contained in the same or different packages.

In some embodiments, the administration of the nanoparticle composition and the other agent are concurrent, i.e., the administration period of the nanoparticle composition and that of the other agent overlap with each other. In some embodiments, the nanoparticle composition is administered for at least one cycle (for example, at least any of 2, 3, or 4 cycles) prior to the administration of the other agent. In some embodiments, the other agent is administered for at least any of one, two, three, or four weeks. In some embodiments, the administrations of the nanoparticle composition and the other agent are initiated at about the same time (for example, within any one of 1, 2, 3, 4, 5, 6, or 7 days). In some embodiments, the administrations of the nanoparticle composition and the other agent are terminated at about the same time (for example, within any one of 1, 2, 3, 4, 5, 6, or 7 days). In some embodiments, the administration of the other agent continues (for example for about any one of 1, 2, 3, 4, 5, 6, 7, 8, 9, 10, 11, or 12 months) after the termination of the administration of the nanoparticle composition. In some embodiments, the administration of the other agent is initiated after (for example after about any one of 1, 2, 3, 4, 5, 6, 7, 8, 9, 10, 11, or we months) the initiation of the administration of the nanoparticle composition. In some embodiments, the administrations of the nanoparticle composition and the other agent are initiated and terminated at about the same time. In some embodiments, the administrations of the nanoparticle composition and the other agent are initiated at about the same time and the administration of the other agent continues (for example for about any one of 1, 2, 3, 4, 5, 6, 7, 8, 9, 10, 11, or 12 months) after the termination of the administration of the nanoparticle composition. In some embodiments, the administration of the nanoparticle composition and the other agent stop at about the same time and the administration of the other agent is initiated after (for example after about any one of 1, 2, 3, 4, 5, 6, 7, 8, 9, 10, 11, or we months) the initiation of the administration of the nanoparticle composition.

In some embodiments, the administration of the nanoparticle composition and the other agent are non-concurrent. For example, in some embodiments, the administration of the nanoparticle composition is terminated before the other agent is administered. In some embodiments, the administration of the other agent is terminated before the nanoparticle composition is administered. The time period between these two non-concurrent administrations can range from about two to eight weeks, such as about four weeks.

The dosing frequency of the drug-containing nanoparticle composition and the other agent may be adjusted over the course of the treatment, based on the judgment of the administering physician. When administered separately, the drug-containing nanoparticle composition and the other agent can be administered at different dosing frequency or intervals. For example, the drug-containing nanoparticle composition can be administered weekly, while a chemotherapeutic agent can be administered more or less frequently. In some embodiments, sustained continuous release formulation of the drug-containing nanoparticle and/or chemotherapeutic agent may be used. Various formulations and devices for achieving sustained release are known in the art. A combination of the administration configurations described herein can also be used.

The nanoparticle composition and the other agent can be administered using the same route of administration or different routes of administration. In some embodiments (for both simultaneous and sequential administrations), the taxane in the nanoparticle composition and the other agent are administered at a predetermined ratio. For example, in some embodiments, the ratio by weight of the taxane in the nanoparticle composition and the other agent is about 1 to 1. In some embodiments, the weight ratio may be between about 0.001 to about 1 and about 1000 to about 1, or between about 0.01 to about 1 and 100 to about 1. In some embodiments, the ratio by weight of the taxane in the nanoparticle composition and the other agent is less than about any of 100:1, 50:1, 30:1, 10:1, 9:1, 8:1, 7:1, 6:1, 5:1, 4:1, 3:1, 2:1, and 1:1 In some embodiments, the ratio by weight of the taxane in the nanoparticle composition and the other agent is more than about any of 1:1, 2:1, 3:1, 4:1, 5:1, 6:1, 7:1, 8:1, 9:1, 30:1, 50:1, 100:1. Other ratios are contemplated.

The doses required for the taxane and/or the other agent may (but not necessarily) be lower than what is normally required when each agent is administered alone. Thus, in some embodiments, a subtherapeutic amount of the drug in the nanoparticle composition and/or the other agent is administered. "Subtherapeutic amount" or "subtherapeutic level" refer to an amount that is less than the therapeutic amount, that is, less than the amount normally used when the drug in the nanoparticle composition and/or the other agent are administered alone. The reduction may be reflected in terms of the amount administered at a given administration and/or the amount administered over a given period of time (reduced frequency).

In some embodiments, enough chemotherapeutic agent is administered so as to allow reduction of the normal dose of the drug in the nanoparticle composition required to effect the same degree of treatment by at least about any of 5%, 10%, 20%, 30%, 50%, 60%, 70%, 80%, 90%, or more. In some embodiments, enough drug in the nanoparticle composition is administered so as to allow reduction of the normal dose of the other agent required to effect the same degree of treatment by at least about any of 5%, 10%, 20%, 30%, 50%, 60%, 70%, 80%, 90%, or more.

In some embodiments, the dose of both the taxane in the nanoparticle composition and the other agent are reduced as compared to the corresponding normal dose of each when administered alone. In some embodiments, both the taxane in the nanoparticle composition and the other agent are administered at a subtherapeutic, i.e., reduced, level. In some embodiments, the dose of the nanoparticle composition and/or the other agent is substantially less than the established maximum toxic dose (MTD). For example, the dose of the nanoparticle composition and/or the other agent is less than about 50%, 40%, 30%, 20%, or 10% of the MTD.

A combination of the administration configurations described herein can be used. The combination therapy methods described herein may be performed alone or in conjunction with another therapy, such as chemotherapy, radiation therapy, surgery, hormone therapy, gene therapy, immunotherapy, chemoimmunotherapy, hepatic artery-based therapy, cryotherapy, ultrasound therapy, liver transplantation, local ablative therapy, radiofrequency ablation therapy, photodynamic therapy, and the like. Additionally, a person having a greater risk of developing the pancreatic cancer may receive treatments to inhibit or and/or delay the development of the disease.

The other agent described herein can be administered to an individual (such as human) via various routes, such as parenterally, including intravenous, intra-arterial, intraperitoneal, intrapulmonary, oral, inhalation, intravesicular, intramuscular, intra-tracheal, subcutaneous, intraocular, intrathecal, or transdermal. In some embodiments, the other agent is administrated intravenously. In some embodiments, the nanoparticle composition is administered orally.

The dosing frequency of the other agent can be the same or different from that of the nanoparticle composition. Exemplary frequencies are provided above. As further example, the other agent can be administered three times a day, two times a day, daily, 6 times a week, 5 times a week, 4 times a week, 3 times a week, two times a week, weekly. In some embodiments, the other agent is administered twice daily or three times daily. Exemplary amounts of the other agent include, but are not limited to, any of the following ranges: about 0.5 to about 5 mg, about 5 to about 10 mg, about 10 to about 15 mg, about 15 to about 20 mg, about 20 to about 25 mg, about 20 to about 50 mg, about 25 to about 50 mg, about 50 to about 75 mg, about 50 to about 100 mg, about 75 to about 100 mg, about 100 to about 125 mg, about 125 to about 150 mg, about 150 to about 175 mg, about 175 to about 200 mg, about 200 to about 225 mg, about 225 to about 250 mg, about 250 to about 300 mg, about 300 to about 350 mg, about 350 to about 400 mg, about 400 to about 450 mg, or about 450 to about 500 mg. For example, the other agent can be administered at a dose of about 1 mg/kg to about 200 mg/kg (including for example about 1 mg/kg to about 20 mg/kg, about 20 mg/kg to about 40 mg/kg, about 40 mg/kg to about 60 mg/kg, about 60 mg/kg to about 80 mg/kg, about 80 mg/kg to about 100 mg/kg, about 100 mg/kg to about 120 mg/kg, about 120 mg/kg to about 140 mg/kg, about 140 mg/kg to about 200 mg/kg).

In some embodiments the other agent is vandetanib. In some embodiments, the effective amount of vandetanib about 100 mg, about 100 mg to about 200 mg, about 200 mg, about 200 mg to about 300 mg, about 300 mg. In some embodiments, the vandetanib is administered orally. In some embodiments, the vandetanib is administered daily. In some embodiments, the vandetanib is administered daily for three weeks of a 28 day cycle.

In some embodiments, the effective amount of taxane in the nanoparticle composition is between about 45 mg/m$^2$ to about 350 mg/m$^2$ and the effective amount of the other agent is about 1 mg/kg to about 200 mg/kg (including for example about 1 mg/kg to about 20 mg/kg, about 20 mg/kg to about 40 mg/kg, about 40 mg/kg to about 60 mg/kg, about 60 mg/kg to about 80 mg/kg, about 80 mg/kg to about 100 mg/kg, about 100 mg/kg to about 120 mg/kg, about 120 mg/kg to about 140 mg/kg, about 140 mg/kg to about 200 mg/kg). In some embodiments, the effective amount of taxane in the nanoparticle composition is between about 80 mg/m$^2$ to about 350 mg/m$^2$ and the effective amount of the other agent is about 1 mg/kg to about 200 mg/kg (including for example about 1 mg/kg to about 20 mg/kg, about 20 mg/kg to about 40 mg/kg, about 40 mg/kg to about 60 mg/kg, about 60 mg/kg to about 80 mg/kg, about 80 mg/kg to about 100 mg/kg, about 100 mg/kg to about 120 mg/kg, about 120 mg/kg to about 140 mg/kg, about 140 mg/kg to about 200 mg/kg). In some embodiments, the effective amount of taxane in the nanoparticle composition is between about 80 mg/m$^2$ to about 300 mg/m$^2$ and the effective amount of the other agent is about 1 mg/kg to about 200 mg/kg (including for example about 1 mg/kg to about 20 mg/kg, about 20 mg/kg to about 40 mg/kg, about 40 mg/kg to about 60 mg/kg, about 60 mg/kg to about 80 mg/kg, about 80 mg/kg to about 100 mg/kg, about 100 mg/kg to about 120 mg/kg, about 120 mg/kg to about 140 mg/kg, about 140 mg/kg to about 200 mg/kg). In some embodiments, the effective amount of taxane in the nanoparticle composition is between about 150 mg/m$^2$ to about 350 mg/m$^2$ and the effective amount of the other agent is about 1 mg/kg to about 200 mg/kg (including for example about 1 mg/kg to about 20 mg/kg, about 20 mg/kg to about 40 mg/kg, about 40 mg/kg to about 60 mg/kg, about 60 mg/kg to about 80 mg/kg, about 80 mg/kg to about 100 mg/kg, about 100 mg/kg to about 120 mg/kg, about 120 mg/kg to about 140 mg/kg, about 140 mg/kg to about 200 mg/kg). In some embodiments, the effective amount of taxane in the nanoparticle composition is between about 80 mg/m$^2$ to about 150 mg/m$^2$ and the effective amount of the other agent is about 1 mg/kg to about 200 mg/kg (including for example about 1 mg/kg to about 20 mg/kg, about 20 mg/kg to about 40 mg/kg, about 40 mg/kg to about 60 mg/kg, about 60 mg/kg to about 80 mg/kg, about 80 mg/kg to about 100 mg/kg, about 100 mg/kg to about 120 mg/kg, about 120 mg/kg to about 140 mg/kg, about 140 mg/kg to about 200 mg/kg). In some embodiments, the effective amount of taxane (e.g., paclitaxel) in the nanoparticle composition is about 100 mg/m². In some embodiments, the effective amount of taxane in the nanoparticle composition is between about 170 mg/m² to about 200 mg/m² and the effective amount of the other agent is about 1 mg/kg to about 200 mg/kg (including for example about 1 mg/kg to about 20 mg/kg, about 20 mg/kg to about 40 mg/kg, about 40 mg/kg to about 60 mg/kg, about 60 mg/kg to about 80 mg/kg, about 80 mg/kg to about 100 mg/kg, about 100 mg/kg to about 120 mg/kg, about 120 mg/kg to about 140 mg/kg, about 140 mg/kg to about 200 mg/kg). In some embodiments, the effective amount of taxane in the nanoparticle composition is between about 200 mg/m² to about 350 mg/m² and the effective amount of the other agent is about 1 mg/kg to about 200 mg/kg (including for example about 1 mg/kg to about 20 mg/kg, about 20 mg/kg to about 40 mg/kg, about 40 mg/kg to about 60 mg/kg, about 60 mg/kg to about 80 mg/kg, about 80 mg/kg to about 100 mg/kg, about 100 mg/kg to about 120 mg/kg, about 120 mg/kg to about 140 mg/kg, about 140 mg/kg to about 200 mg/kg). In some embodiments, the effective amount of taxane (e.g., paclitaxel) in the nanoparticle composition is about 260 mg/m². In some embodiments of any of the above methods, the effective amount of the other agent is about 20-30 mg/kg, about 30-40 mg/kg, about 40-50 mg/kg, about 50-60 mg/kg, about 60-70 mg/kg, about 70-80 mg/kg, about 80-100 mg/kg, or about 100-120 mg/kg.

In some embodiments, the effective amount of taxane (e.g., paclitaxel) in the nanoparticle composition is between about 30 to about 300 mg/m² and the effective amount of the other agent is between about 100 to about 5000 mg/m². In some embodiments, the effective amount of taxane (e.g., paclitaxel) in the nanoparticle composition is about any of 30, 50, 75, 100, 125, 150, 175, 200, 225, 250, 275, or 300 mg/m² and the effective amount of the other agent is about any of 100, 200, 300, 400, 500, 600, 700, 800, 900, 1000, 1250, 1500, 1750, 2000, 2250, 2500, 2750, 3000, 3250, 3500, 3750, 4000, 4250, 4500, 4750, or 5000 mg/m². In some embodiments, the nanoparticle composition is about 30 to about 300 mg/m² and the effective amount of the other agent is about 100 to about 5000 mg/m², wherein the nanoparticle composition and the other agent are both administered weekly to the individual who has been previously treated for pancreatic cancer. In some embodiments, the nanoparticle composition is about 30 to about 300 mg/m² and the effective amount of the other agent is about 100 to about 5000 mg/m², wherein the nanoparticle composition and the other agent are both administered at a frequency of less than weekly to the individual who has been previously treated for pancreatic cancer. In some embodiments, the nanoparticle composition is about 30 to about 300 mg/m² and the effective amount of the other agent is about 100 to about 5000 mg/m², wherein the nanoparticle composition and the other agent are both administered intravenously over 30 minutes on days 1, 8, and 15 on a 28-day cycle to the individual who has been previously treated for pancreatic cancer (e.g., the individual who has progressed on gemcitabine-based therapy).

In some embodiments, the appropriate doses of other agents are approximately those already employed in clinical therapies wherein the other agent are administered alone or in combination with other agents.

Nanoparticle Compositions

The nanoparticle compositions described herein comprise nanoparticles comprising (in various embodiments consisting essentially of) a taxane (such as paclitaxel) and an albumin (such as human serum albumin). Nanoparticles of poorly water soluble drugs (such as taxane) have been disclosed in, for example, U.S. Pat. Nos. 5,916,596; 6,506,405; 6,749,868, and 6,537,579; 7,820,788, and US Pat. Pub. Nos. 2006/0263434, and 2007/0082838; PCT Patent Application WO08/137148, each of which is incorporated by reference in their entirety.

In some embodiments, the composition comprises nanoparticles with an average or mean diameter of no greater than about 1000 nanometers (nm), such as no greater than about any of 900, 800, 700, 600, 500, 400, 300, 200, and 100 nm. In some embodiments, the average or mean diameters of the nanoparticles is no greater than about 200 nm. In some embodiments, the average or mean diameters of the nanoparticles is no greater than about 150 nm. In some embodiments, the average or mean diameters of the nanoparticles is no greater than about 100 nm. In some embodiments, the average or mean diameter of the nanoparticles is about 20 to about 400 nm. In some embodiments, the average or mean diameter of the nanoparticles is about 40 to about 200 nm. In some embodiments, the nanoparticles are sterile-filterable.

In some embodiments, the nanoparticles in the composition described herein have an average diameter of no greater than about 200 nm, including for example no greater than about any one of 190, 180, 170, 160, 150, 140, 130, 120, 110, 100, 90, 80, 70, or 60 nm. In some embodiments, at least about 50% (for example at least about any one of 60%, 70%, 80%, 90%, 95%, or 99%) of the nanoparticles in the composition have a diameter of no greater than about 200 nm, including for example no greater than about any one of 190, 180, 170, 160, 150, 140, 130, 120, 110, 100, 90, 80, 70, or 60 nm. In some embodiments, at least about 50% (for example at least any one of 60%, 70%, 80%, 90%, 95%, or 99%) of the nanoparticles in the composition fall within the range of about 20 to about 400 nm, including for example about 20 to about 200 nm, about 40 to about 200 nm, about 30 to about 180 nm, and any one of about 40 to about 150, about 50 to about 120, and about 60 to about 100 nm.

In some embodiments, the albumin has sulfhydral groups that can form disulfide bonds. In some embodiments, at least about 5% (including for example at least about any one of 10%, 15%, 20%, 25%, 30%, 40%, 50%, 60%, 70%, 80%, or 90%) of the albumin in the nanoparticle portion of the composition are crosslinked (for example crosslinked through one or more disulfide bonds).

In some embodiments, the nanoparticles comprise the taxane (such as paclitaxel) coated with an albumin (e.g., human serum albumin). In some embodiments, the composition comprises taxane in both nanoparticle and non-nanoparticle forms, wherein at least about any one of 50%, 60%, 70%, 80%, 90%, 95%, or 99% of the taxane in the composition are in nanoparticle form. In some embodiments, the taxane in the nanoparticles constitutes more than about any one of 50%, 60%, 70%, 80%, 90%, 95%, or 99% of the nanoparticles by weight. In some embodiments, the nanoparticles have a non-polymeric matrix. In some embodiments, the nanoparticles comprise a core of taxane that is substantially free of polymeric materials (such as polymeric matrix).

In some embodiments, the composition comprises albumin in both nanoparticle and non-nanoparticle portions of the composition, wherein at least about any one of 50%, 60%, 70%, 80%, 90%, 95%, or 99% of the albumin in the composition are in non-nanoparticle portion of the composition.

In some embodiments, the weight ratio of albumin (such as human serum albumin) and taxane in the nanoparticle composition is about 18:1 or less, such as about 15:1 or less, for example about 10:1 or less. In some embodiments, the weight ratio of albumin (such as human serum albumin) and taxane in the composition falls within the range of any one of about 1:1 to about 18:1, about 2:1 to about 15:1, about 3:1 to about 13:1, about 4:1 to about 12:1, about 5:1 to about 10:1. In some embodiments, the weight ratio of albumin and taxane in the nanoparticle portion of the composition is about any one of 1:2, 1:3, 1:4, 1:5, 1:10, 1:15, or less. In some embodiments, the weight ratio of the albumin (such as human serum albumin) and the taxane in the composition is any one of the following: about 1:1 to about 18:1, about 1:1 to about 15:1, about 1:1 to about 12:1, about 1:1 to about 10:1, about 1:1 to about 9:1, about 1:1 to about 8:1, about 1:1 to about 7:1, about 1:1 to about 6:1, about 1:1 to about 5:1, about 1:1 to about 4:1, about 1:1 to about 3:1, about 1:1 to about 2:1, about 1:1 to about 1:1.

In some embodiments, the nanoparticle composition comprises one or more of the above characteristics.

The nanoparticles described herein may be present in a dry formulation (such as lyophilized composition) or suspended in a biocompatible medium. Suitable biocompatible media include, but are not limited to, water, buffered aqueous media, saline, buffered saline, optionally buffered solutions of amino acids, optionally buffered solutions of proteins, optionally buffered solutions of sugars, optionally buffered solutions of vitamins, optionally buffered solutions of synthetic polymers, lipid-containing emulsions, and the like.

In some embodiments, the pharmaceutically acceptable carrier comprises human serum albumin. Human serum albumin (HSA) is a highly soluble globular protein of $M_r$ 65K and consists of 585 amino acids. HSA is the most abundant protein in the plasma and accounts for 70-80% of the colloid osmotic pressure of human plasma. The amino acid sequence of HSA contains a total of 17 disulphide bridges, one free thiol (Cys 34), and a single tryptophan (Trp 214). Intravenous use of HSA solution has been indicated for the prevention and treatment of hypovolumic shock (see, e.g., Tullis, *JAMA*, 237, 355-360, 460-463, (1977)) and Houser et al., *Surgery, Gynecology and Obstetrics*, 150, 811-816 (1980)) and in conjunction with exchange transfusion in the treatment of neonatal hyperbilirubinemia (see, e.g., Finlayson, *Seminars in Thrombosis and Hemostasis*, 6, 85-120, (1980)). Other albumins are contemplated, such as bovine serum albumin. Use of such non-human albumins could be appropriate, for example, in the context of use of these compositions in non-human mammals, such as the veterinary (including domestic pets and agricultural context).

Human serum albumin (HSA) has multiple hydrophobic binding sites (a total of eight for fatty acids, an endogenous ligand of HSA) and binds a diverse set of taxanes, especially neutral and negatively charged hydrophobic compounds (Goodman et al., *The Pharmacological Basis of Therapeutics*, 9$^{th}$ ed, McGraw-Hill New York (1996)). Two high affinity binding sites have been proposed in subdomains IIA and IIIA of HSA, which are highly elongated hydrophobic pockets with charged lysine and arginine residues near the surface which function as attachment points for polar ligand features (see, e.g., Fehske et al., *Biochem. Pharmcol.*, 30, 687-92 (198a), Vorum, *Dan. Med. Bull.*, 46, 379-99 (1999), Kragh-Hansen, *Dan. Med. Bull.*, 1441, 131-40 (1990), Curry et al., *Nat. Struct. Biol.*, 5, 827-35 (1998), Sugio et al., *Protein. Eng.*, 12, 439-46 (1999), He et al., *Nature*, 358, 209-15 (199b), and Carter et al., *Adv. Protein. Chem.*, 45, 153-203 (1994)). Paclitaxel and propofol have been shown to bind HSA (see, e.g., Paal et al., *Eur. J. Biochem.*, 268(7), 2187-91 (200a), Purcell et al., *Biochim. Biophys. Acta*, 1478(a), 61-8 (2000), Altmayer et al., *Arzneimittelforschung*, 45, 1053-6 (1995), and Garrido et al., *Rev. Esp. Anestestiol. Reanim.*, 41, 308-12 (1994)). In addition, docetaxel has been shown to bind to human plasma proteins (see, e.g., Urien et al., *Invest. New Drugs*, 14(b), 147-51 (1996)).

The albumin (such as human serum albumin) in the composition generally serves as a carrier for the taxane, i.e., the albumin in the composition makes the taxane more readily suspendable in an aqueous medium or helps maintain the suspension as compared to compositions not comprising an albumin. This can avoid the use of toxic solvents (or surfactants) for solubilizing the taxane, and thereby can reduce one or more side effects of administration of the taxane into an individual (such as a human). Thus, in some embodiments, the composition described herein is substantially free (such as free) of surfactants, such as Cremophor (including Cremophor EL® (BASF)). In some embodiments, the nanoparticle composition is substantially free (such as free) of surfactants. A composition is "substantially free of Cremophor" or "substantially free of surfactant" if the amount of Cremophor or surfactant in the composition is not sufficient to cause one or more side effect(s) in an individual when the nanoparticle composition is administered to the individual. In some embodiments, the nanoparticle composition contains less than about any one of 20%, 15%, 10%, 7.5%, 5%, 2.5%, or 1% organic solvent or surfactant.

The amount of albumin in the composition described herein will vary depending on other components in the composition. In some embodiments, the composition comprises an albumin in an amount that is sufficient to stabilize the taxane in an aqueous suspension, for example, in the form of a stable colloidal suspension (such as a stable suspension of nanoparticles). In some embodiments, the albumin is in an amount that reduces the sedimentation rate of the taxane in an aqueous medium. For particle-containing compositions, the amount of the albumin also depends on the size and density of nanoparticles of the taxane.

A taxane is "stabilized" in an aqueous suspension if it remains suspended in an aqueous medium (such as without visible precipitation or sedimentation) for an extended period of time, such as for at least about any of 0.1, 0.2, 0.25, 0.5, 1, 2, 3, 4, 5, 6, 7, 8, 9, 10, 11, 12, 24, 36, 48, 60, or 72 hours. The suspension is generally, but not necessarily, suitable for administration to an individual (such as human). Stability of the suspension is generally (but not necessarily) evaluated at a storage temperature (such as room temperature (such as 20-25° C.) or refrigerated conditions (such as 4° C.)). For example, a suspension is stable at a storage temperature if it exhibits no flocculation or particle agglomeration visible to the naked eye or when viewed under the optical microscope at 1000 times, at about fifteen minutes after preparation of the suspension. Stability can also be evaluated under accelerated testing conditions, such as at a temperature that is higher than about 40° C.

In some embodiments, the albumin is present in an amount that is sufficient to stabilize the taxane in an aqueous suspension at a certain concentration. For example, the concentration of the taxane in the composition is about 0.1 to about 100 mg/ml, including for example any of about 0.1 to about 50 mg/ml, about 0.1 to about 20 mg/ml, about 1 to about 10 mg/ml, about 2 mg/ml to about 8 mg/ml, about 4 to about 6 mg/ml, about 5 mg/ml. In some embodiments, the concentration of the taxane is at least about any of 1.3 mg/ml, 1.5 mg/ml, 2 mg/ml, 3 mg/ml, 4 mg/ml, 5 mg/ml, 6 mg/ml, 7 mg/ml, 8 mg/ml, 9 mg/ml, 10 mg/ml, 15 mg/ml, 20 mg/ml, 25 mg/ml, 30 mg/ml, 40 mg/ml, and 50 mg/ml. In some embodiments, the albumin is present in an amount that avoids use of surfactants (such as Cremophor), so that the composition is free or substantially free of surfactant (such as Cremophor).

In some embodiments, the composition, in liquid form, comprises from about 0.1% to about 50% (w/v) (e.g. about 0.5% (w/v), about 5% (w/v), about 10% (w/v), about 15% (w/v), about 20% (w/v), about 30% (w/v), about 40% (w/v), or about 50% (w/v)) of albumin. In some embodiments, the composition, in liquid form, comprises about 0.5% to about 5% (w/v) of albumin.

In some embodiments, the weight ratio of albumin, e.g., albumin, to the taxane in the nanoparticle composition is such that a sufficient amount of taxane binds to, or is transported by, the cell. While the weight ratio of albumin to taxane will have to be optimized for different albumin and taxane combinations, generally the weight ratio of albumin, e.g., albumin, to taxane (w/w) is about 0.01:1 to about 100:1, about 0.02:1 to about 50:1, about 0.05:1 to about 20:1, about 0.1:1 to about 20:1, about 1:1 to about 18:1, about 2:1 to about 15:1, about 3:1 to about 12:1, about 4:1 to about 10:1, about 5:1 to about 9:1, or about 9:1. In some embodiments, the albumin to taxane weight ratio is about any of 18:1 or less, 15:1 or less, 14:1 or less, 13:1 or less, 12:1 or less, 11:1 or less, 10:1 or less, 9:1 or less, 8:1 or less, 7:1 or less, 6:1 or less, 5:1 or less, 4:1 or less, and 3:1 or less. In some embodiments, the weight ratio of the albumin (such as human serum albumin) and the taxane in the composition is any one of the following: about 1:1 to about 18:1, about 1:1 to about 15:1, about 1:1 to about 12:1, about 1:1 to about 10:1, about 1:1 to about 9:1, about 1:1 to about 8:1, about 1:1 to about 7:1, about 1:1 to about 6:1, about 1:1 to about 5:1, about 1:1 to about 4:1, about 1:1 to about 3:1, about 1:1 to about 2:1, about 1:1 to about 1:1.

In some embodiments, the albumin allows the composition to be administered to an individual (such as human) without significant side effects. In some embodiments, the albumin (such as human serum albumin) is in an amount that is effective to reduce one or more side effects of administration of the taxane to a human. The term "reducing one or more side effects of administration of the taxane" refers to reduction, alleviation, elimination, or avoidance of one or more undesirable effects caused by the taxane, as well as side effects caused by delivery vehicles (such as solvents that render the taxanes suitable for injection) used to deliver the taxane. Such side effects include, for example, myelosuppression, neurotoxicity, hypersensitivity, inflammation, venous irritation, phlebitis, pain, skin irritation, peripheral neuropathy, neutropenic fever, anaphylactic reaction, venous thrombosis, extravasation, and combinations thereof. These side effects, however, are merely exemplary and other side effects, or combination of side effects, associated with taxanes can be reduced.

In some embodiments, the nanoparticle composition comprises ABRAXANE® (Nab-paclitaxel). In some embodiments, the nanoparticle composition is ABRAXANE® (Nab-paclitaxel). ABRAXANE® is a formulation of paclitaxel stabilized by human albumin USP, which can be dispersed in directly injectable physiological solution. When dispersed in a suitable aqueous medium such as 0.9% sodium chloride injection or 5% dextrose injection, ABRAXANE® forms a stable colloidal suspension of paclitaxel. The mean particle size of the nanoparticles in the colloidal suspension is about 130 nanometers. Since HSA is freely soluble in water, ABRAXANE® can be reconstituted in a wide range of concentrations ranging from dilute (0.1 mg/ml paclitaxel) to concentrated (20 mg/ml paclitaxel), including for example about 2 mg/ml to about 8 mg/ml, about 5 mg/ml.

Methods of making nanoparticle compositions are known in the art. For example, nanoparticles containing taxanes (such as paclitaxel) and albumin (such as human serum albumin) can be prepared under conditions of high shear forces (e.g., sonication, high pressure homogenization, or the like). These methods are disclosed in, for example, U.S. Pat. Nos. 5,916,596; 6,506,405; 6,749,868; 6,537,579, 7,820,788, and also in U.S. Pat. Pub. Nos. 2007/0082838, 2006/0263434 and PCT Application WO08/137148.

Briefly, the taxane (such as paclitaxel) is dissolved in an organic solvent, and the solution can be added to an albumin solution. The mixture is subjected to high pressure homogenization. The organic solvent can then be removed by evaporation. The dispersion obtained can be further lyophilized. Suitable organic solvent include, for example, ketones, esters, ethers, chlorinated solvents, and other solvents known in the art. For example, the organic solvent can be methylene chloride or chloroform/ethanol (for example with a ratio of 1:9, 1:8, 1:7, 1:6, 1:5, 1:4, 1:3, 1:2, 1:1, 2:1, 3:1, 4:1, 5:1, 6:1, 7:1, 8:1, or 9:1.

Other Components in the Nanoparticle Compositions

The nanoparticles described herein can be present in a composition that include other agents, excipients, or stabilizers. For example, to increase stability by increasing the negative zeta potential of nanoparticles, certain negatively charged components may be added. Such negatively charged components include, but are not limited to bile salts of bile acids consisting of glycocholic acid, cholic acid, chenodeoxycholic acid, taurocholic acid, glycochenodeoxycholic acid, taurochenodeoxycholic acid, litocholic acid, ursodeoxycholic acid, dehydrocholic acid and others; phospholipids including lecithin (egg yolk) based phospholipids which include the following phosphatidylcholines: palmitoyloleoylphosphatidylcholine, palmitoyllinoleoylphosphatidylcholine, stearoyllinoleoylphosphatidylcholine stearoyloleoylphosphatidylcholine, stearoylarachidoylphosphatidylcholine, and dipalmitoylphosphatidylcholine. Other phospholipids including L-α-dimyristoylphosphatidylcholine (DMPC), dioleoylphosphatidylcholine (DOPC), distearyolphosphatidylcholine (DSPC), hydrogenated soy phosphatidylcholine (HSPC), and other related compounds. Negatively charged surfactants or emulsifiers are also suitable as additives, e.g., sodium cholesteryl sulfate and the like.

In some embodiments, the composition is suitable for administration to a human. In some embodiments, the composition is suitable for administration to a mammal such as, in the veterinary context, domestic pets and agricultural animals. There are a wide variety of suitable formulations of the nanoparticle composition (see, e.g., U.S. Pat. Nos. 5,916,596; 6,096,331; 7,820,788). The following formulations and methods are merely exemplary and are in no way limiting. Formulations suitable for oral administration can consist of (a) liquid solutions, such as an effective amount of the compound dissolved in diluents, such as water, saline, or orange juice, (b) capsules, sachets or tablets, each containing a predetermined amount of the active ingredient, as solids or granules, (c) suspensions in an appropriate liquid, and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

Examples of suitable carriers, excipients, and diluents include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline solution, syrup, methylcellulose, methyl- and propylhydroxybenzoates, talc, magnesium stearate, and mineral oil. The formulations can additionally include lubricating agents, wetting agents, emulsifying and suspending agents, preserving agents, sweetening agents or flavoring agents.

Formulations suitable for parenteral administration include aqueous and non-aqueous, isotonic sterile injection solutions, which can contain anti-oxidants, buffers, bacteriostats, and solutes that render the formulation compatible with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described. Injectable formulations are preferred.

In some embodiments, the composition is formulated to have a pH range of about 4.5 to about 9.0, including for example pH ranges of any of about 5.0 to about 8.0, about 6.5 to about 7.5, and about 6.5 to about 7.0. In some embodiments, the pH of the composition is formulated to no less than about 6, including for example no less than about any of 6.5, 7, or 8 (such as about 8). The composition can also be made to be isotonic with blood by the addition of a suitable tonicity modifier, such as glycerol.

Kits, Medicines, and Compositions

The invention also provides kits, medicines, compositions, and unit dosage forms for use in any of the methods described herein.

Kits of the invention include one or more containers comprising taxane-containing nanoparticle compositions (or unit dosage forms and/or articles of manufacture) and/or another agent (such as the agents described herein), and in some embodiments, further comprise instructions for use in accordance with any of the methods described herein. The kit may further comprise a description of selection an individual suitable or treatment. Instructions supplied in the kits of the invention are typically written instructions on a label or package insert (e.g., a paper sheet included in the kit), but machine-readable instructions (e.g., instructions carried on a magnetic or optical storage disk) are also acceptable.

For example, in some embodiments, the kit comprises a) a composition comprising nanoparticles comprising a taxane and an albumin (such as human serum albumin), and b) instructions for administering the nanoparticle composition for treatment of pancreatic cancer in an individual who has been previously treated for pancreatic cancer (e.g., who has progressed on prior therapy). In some embodiments, the kit comprises a) a composition comprising nanoparticles comprising a taxane and an albumin (such as human serum albumin), and b) instructions for administering the nanoparticle composition for treatment of pancreatic cancer in an individual who has progressed on gemcitabine-based therapy (e.g., gemcitabine monotherapy or gemcitabine combination therapy with gemcitabine and erlotinib, gemcitabine and capecitabine, or gemcitabine and 5-FU). In some embodiments, the kit comprises a) a composition comprising nanoparticles comprising a taxane and an albumin (such as human serum albumin), b) an effective amount of another agent, and c) instructions for administering the nanoparticle composition and the other agents for treatment of pancreatic cancer in an individual who has been previously treated for pancreatic cancer (e.g., who has progressed on prior therapy). In some embodiments, the kit comprises a) a composition comprising nanoparticles comprising a taxane and an albumin (such as human serum albumin), b) an effective amount of another agent, and c) instructions for administering the nanoparticle composition and the other agents for treatment of pancreatic cancer in an individual who has progressed on gemcitabine-based therapy (e.g., gemcitabine monotherapy or gemcitabine combination therapy with gemcitabine and erlotinib, gemcitabine and capecitabine, or gemcitabine and 5-FU). In some embodiments, the prior therapy comprises administration of gemcitabine ("a gemcitabine-based therapy"). The nanoparticles and the other agents can be present in separate containers or in a single container. For example, the kit may comprise one distinct composition or two or more compositions wherein one composition comprises nanoparticles and one composition comprises another agent.

In some embodiments, the kit comprises a) a composition comprising nanoparticles comprising a taxane and an albumin (such as human serum albumin), b) an effective amount of a VEGFR/EGFR inhibitor (such as vandetanib), and c) instructions for administering the nanoparticle composition and the VEGFR/EGFR inhibitor (such as vandetanib) for the treatment of pancreatic cancer in an individual. The nanoparticles and the VEGFR/EGFR inhibitor (such as vandetanib) are present in separate containers or in a single container. For example, the kit may comprise one distinct composition or two or more compositions wherein one composition comprises nanoparticles and the VEGFR/EGFR inhibitor (such as vandetanib).

The kits of the invention are in suitable packaging. Suitable packaging include, but is not limited to, vials, bottles, jars, flexible packaging (e.g., sealed Mylar or plastic bags), and the like. Kits may optionally provide additional components such as buffers and interpretative information. The present application thus also provides articles of manufacture, which include vials (such as sealed vials), bottles, jars, flexible packaging, and the like.

The instructions relating to the use of the nanoparticle compositions generally include information as to dosage, dosing schedule, and route of administration for the intended treatment. The containers may be unit doses, bulk packages (e.g., multi-dose packages) or sub-unit doses. For example, kits may be provided that contain sufficient dosages of the taxane (such as taxane) as disclosed herein to provide effective treatment of an individual for an extended period, such as any of a week, 8 days, 9 days, 10 days, 11 days, 12 days, 13 days, 2 weeks, 3 weeks, 4 weeks, 6 weeks, 8 weeks, 3 months, 4 months, 5 months, 7 months, 8 months, 9 months, 10 months, 11 months, 12 months, or more. Kits may also include multiple unit doses of the taxane and pharmaceutical compositions and instructions for use and packaged in quantities sufficient for storage and use in pharmacies, for example, hospital pharmacies and compounding pharmacies.

Also provided are medicines, compositions, and unit dosage forms useful for the methods described herein. In some embodiments, there is provided a medicine (or composition) for use in treating pancreatic cancer in an individual who has progressed on gemcitabine-based therapy, comprising nanoparticles comprising a taxane and an albumin (such as human serum albumin). In some embodiments, there is provided a medicine (or composition) for use in treating pancreatic cancer in an individual wherein the individual is resistant or refractory to a gemcitabine-based therapy comprising nanoparticles comprising a taxane and an albumin (such as human serum albumin). In some embodiments, there is provided a medicine (or composition) for use in treating pancreatic cancer in an individual wherein the individual has recurrent pancreatic cancer (for example, the individual develops pancreatic cancer after about any of about 2, 3, 4, 5, 6, 7, 8, 9, 10, 11, 12, 24, or 36 months upon the cessation of a gemcitabine-based therapy) comprising nanoparticles comprising a taxane and an albumin (such as human serum albumin). In some embodiments, there is provided a medicine (or composition) for use in treating pancreatic cancer in an individual wherein a gemcitabine-based therapy has stopped (for example for at least 1, 2, 3, 4, 5, 6, 7, 8, 9, or 10 months) when initiating the treatment with the medicine comprising nanoparticles comprising a taxane and an albumin (such as human serum albumin). In some embodiments, there is provided a medicine (or composition or a unit dosage form) for use in treating pancreatic cancer in conjunction with another agent in an individual who has progressed on gemcitabine-based therapy, comprising nanoparticles comprising a taxane and an albumin (such as human serum albumin). In some embodiments, there is provided a medicine (or composition or a unit dosage form) for use in treating pancreatic cancer in conjunction with another agent in an individual wherein the individual is resistant or refractory to a gemcitabine-based therapy comprising nanoparticles comprising a taxane and an albumin (such as human serum albumin). In some embodiments, there is provided a medicine (or composition or a unit dosage form) for use in treating pancreatic cancer in conjunction with another agent in an individual wherein the individual has recurrent pancreatic cancer (for example, the individual develops pancreatic cancer after about any of about 2, 3, 4, 5, 6, 7, 8, 9, 10, 11, 12, 24, or 36 months upon the cessation of a gemcitabine-based therapy) comprising nanoparticles comprising a taxane and an albumin (such as human serum albumin). In some embodiments, there is provided a medicine (or composition or a unit dosage form) for use in treating pancreatic cancer in conjunction with another agent in an individual wherein a gemcitabine-based therapy has stopped (for example for at least 1, 2, 3, 4, 5, 6, 7, 8, 9, or 10 months) when initiating the treatment with the medicine comprising nanoparticles comprising a taxane and an albumin (such as human serum albumin). In some embodiments, there is provided a medicine (or composition or a unit dosage form) for use in treating pancreatic cancer, comprising nanoparticles comprising a taxane and an albumin (such as human serum albumin) and another agent. In some embodiments, the other agent is not gemcitabine.

In some embodiments, there is provided a medicine (or composition or a unit dosage form) for use in treating pancreatic cancer, comprising nanoparticles comprising a taxane and an albumin (such as human serum albumin) and a VEGFR/EGFR inhibitor (such as vandetanib).

The examples, which are intended to be purely exemplary of the invention and should therefore not be considered to limit the invention in any way, also describe and detail aspects and embodiments of the invention discussed above. The foregoing examples and detailed description are offered by way of illustration and not by way of limitation. All publications, patent applications, and patents cited in this specification are herein incorporated by reference as if each individual publication, patent application, or patent were specifically and individually indicated to be incorporated by reference. In particular, all publications cited herein are expressly incorporated herein by reference for the purpose of describing and disclosing compositions and methodologies which might be used in connection with the invention. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

EXAMPLES

Example 1

A Phase II Trial of Nab-Paclitaxel in Patients with Advanced Pancreatic Cancer Who have Progressed on Gemcitabine-Based Therapy This example demonstrates that Nab-paclitaxel was well tolerated and provided clinical benefit in patients who had progressed on gemcitabine-based therapy.

Materials and Methods

In the Phase II open-label trial, patients with locally advanced, unresectable or metastatic pancreatic ductal carcinoma (ECOG PS 0-2) who progressed within 6 months of gemcitabine-based therapy received nab-paclitaxel at 100 mg/m$^2$ intravenously over 30 minutes on days 1, 8 and 15 on a 28-day cycle. The patients were at least 18 years of age with good organ function. The contrast CT (Computed Tomography) was evaluated at baseline and every 2 cycles. The primary endpoint was 6-month overall survival (OS). The secondary endpoints were response rate by RECIST (Response Evaluation Criteria In Solid Tumors) criteria, progression-free survival (PFS), safety and tolerability, and toxicity profile. The CA19-9 levels were measured at baseline and every 2 cycles. SPARC immunohistochemistry on available pre-treatment tumor specimens was also performed.

Results

Out of 20 patients accrued, 1 patient never received study therapy and was excluded from analysis. The median age was 61 years, 9 (47%) were male, 18 (95%) had stage IV disease, and 15 (79%) had an ECOG PS (Performance Status) of 0-1. The 6-month OS (overall survival) was 58% (95% CI 33%-76%) and the median OS was 7.3 months (95% CI 2.8-13.3). The median PFS (Progression-free survival) was 1.6 months (95% CI 1.5-3.4). One patient had a confirmed partial response (PR) and 6 (32%) had stable disease (SD) as their best response. The remaining 12 patients (63%) had progressive disease (PD) on or before the first response assessment. Five patients were alive with a median follow-up of 12.7 months (range 9.6-16.3), including one with SD on cycle 15 of therapy. After 2 cycles, the median CA 19-9 levels decreased by 52% in patients who had SD or PR, versus an 18% drop in the patients with PD. Correlative studies with SPARC expression are also performed. Non-hematological toxicities were generally mild with grade 1 or 2 nausea, anorexia, hypocalcemia and vomiting occurring in 63%, 47%, 37% and 26% of patients respectively. Grade 3 or 4 neutropenia, neutropenic fever and anemia occurred in 32%, 11% of patients, respectively. There were no cases of grade 3 or 5 neuropathy. Tables 1-6 provides detailed experimental data and results.

TABLE 1

Patient Characteristics (N = 19)

|  | N | % |
|---|---|---|
| Age (years) |  |  |
| Median (Range) | 61 (24-80) |  |
| Sex |  |  |
| Female | 10 | 52.6 |
| Male | 9 | 47.4 |
| Stage |  |  |
| III | 1 | 5.3 |
| IV | 18 | 94.7 |
| Performance Status |  |  |
| 0 | 3 | 15.8 |
| 1 | 12 | 63.2 |
| 2 | 4 | 21.1 |
| Other therapies |  |  |
| Prior adjuvant chemoradiation | 5 | 26.3 |
| Any post-study chemotherapy | 11 | 57.9 |
| Status at the time of report |  |  |
| Deceased | 15 | 78.9 |
| Active, on study | 1 | 5.3 |
| Alive, off study | 3 | 15.8 |

TABLE 2

Best response by RECIST criteria (N = 19)

|  | N (%) | 95% CI |
|---|---|---|
| Partial response (PR) | 1 (5.3) | 0.1-26 |
| Stable disease (SD) | 6 (31.6) | 12.6-56.6 |
| Clinical benefit (PR + SD) | 7 (36.8) | 16.3-61.6 |
| Progressive disease (PD) | 12 (63.2) | 38.4-83.7 |

TABLE 3

Survival (N = 19, Events = 17, Deaths = 11)

| Time point (months) | Progression-free Survival (95% CI) | Overall Survival (95% CI) |
|---|---|---|
| 3 | 31.6% (12.9-52.2) | 73.7% (47.9-88.1) |
| 6 | 15.8% (3.9-34.9) | 57.9% (33.2-76.3) |
| 9 | 5.3% (0.4-21.4) | 47.4% (24.4-67.3) |
| 12 | 5.3 (0.4-21.4) | 36.8% (16.5-57.5) |
| Median | 1.6 months (1.5 to 3.4) | 7.3 months (2.8 to 15.8) |

TABLE 4

Correlation between CA19-9 after 2 cycles and response (N = 19)

|  | N | No. of pts with >50% decrease in CA19-9* |
|---|---|---|
| PR + SF | 7 | 4 (57.1%) |
| PD | 12 | 2 (16.6%) |

TABLE 5

Correlation between CA19-9 after 2 cycles and survival (N = 19)

|  | N | PFS (95% CI) | OS (95% CI) |
|---|---|---|---|
| <50% decrease | 13 | 1.6 months (9.5-1.9) | 6.9 months (1.9-13.3) |
| ≥50% decrease | 6 | 2.7 months (1.4-NA) | 13.8 months (2.8-NA) |
| p value |  |  | 0.244 |

TABLE 6

Adverse events (N = 19, Cycles = 72)

|  | Grade 1-2, N (%) | Grade 3-4, N (%) |
|---|---|---|
| Hematological |  |  |
| Neutropenia | 8 (42.1) | 5 (26.3) |
| Anemia | 11 (57.9) | 2 (10.5) |
| Thrombocytopenia | 1 (5.2) | 0 |
| Neutropenic fever | 0 | 2 (10.5) |
| Non-hematological |  |  |
| Fatigue | 12 (63.1) | 0 |
| Nausea | 12 (63.1) | 0 |
| Aloplecia | 12 (63.1) | 0 |
| Anorexia | 9 (47.4) | 0 |
| Hypocalcemia | 7 (36.8) | (1 (5.2) |
| Vomiting | 5 (26.3) | 0 |
| Neuropathy | 3 (15.8) | 0 |

Conclusion

Nab-paclitaxel was well tolerated in patients with advanced pancreatic cancer who had progressed on gemcitabine-based therapy. 37% of patients treated in this phase II trial derived clinical benefit (partial response or disease stabilization) and 21% remained on therapy for at least 6 months suggesting that Nab-paclitaxel has antitumor activity in this setting. There was a trend towards CA 19-9 being a predictor of clinical benefit, PFS and OS, but this did not reach statistical significance. Other studies have suggested that SPARC expression is associated with a higher response rate to Nab-paclitaxel (Von Hoff et al., *J. Clin. Oncol.* 27(155):4525 (2009)). The correlation of SPARC expression with response or survival is under further examination.

Example 2

A Phase I Study of Two Different Schedules of Nab-Paclitaxel with Ascending Doses of Vandetanib with Expansion in Patients with Pancreatic Cancer This Example reports a Phase I study of two different schedules of Nab-paclitaxel with ascending doses of vandetanib with expansion in patients with pancreatic cancer. A primary objective was to determine the maximum tolerated dose (MTD) of the combination of Nab-paclitaxel and vandetanib. A secondary objective was to assess preliminary efficacy in patients with pancreatic cancer.

Materials and Methods

Patients were randomized to one of two cohorts. Doses of Nab-paclitaxel for Cohort A were fixed at 100 mg/m$^2$ Nab-paclitaxel intravenously weekly for three weeks on a 28 day cycle. Doses of Nab-paclitaxel for Cohort B were fixed at 260 mg/m$^2$ Nab-paclitaxel intravenously on a three week schedule. Vandetanib was administered to patients at doses of 100 mg, 200 mg, or 300 mg by mouth daily for each cohort. A 3+3 design was used. Expansion at the maximum tolerated dose (MTD) to 15 patients was planned for both cohorts. Cohort A expansion was restricted to pancreatic cancer patients who failed gemcitabine-based therapy. Two single nucleotide polymorphisms, SPARC rs1059829 and SPARC rs3210714, were evaluated by PCR-RFLP in twenty five patients.

Results

One indication of dose limiting toxicity (DLT) was reported at each dose level in cohort A including grade 3 rashes in two patients and grade 4 neutropenia in one patient (Table 7). No indications of DLTs were recorded for patients in cohort B. The MTD was 100 mg/m$^2$ for Nab-paclitaxel administered intravenously weekly for three out of four weeks combined with 300 mg vandetanib administered daily (cohort A). The MTD was 260 mg/m$^2$ for Nab-paclitaxel administered intravenously every three weeks in combination with 300 mg vandetanib administered daily (cohort B). Twenty-nine patients with pancreatic cancer were treated: nine from cohort A (dose escalation), fifteen from cohort A (dose expansion) and five from cohort B. The median age of patients was 62. There were sixteen males, and thirteen females. The median number of prior treatments for Cohort A was two (range 1-4). Twenty-two patients with pancreatic cancer were evaluable for response: six (27.5%) of these patients were partial responders (PR), ten (45%) showed stable disease (SD) and six showed (27.5%) disease progression. The median progression free survival (PFS) was 5.3 months (95% CI: 3.7-7.3) and the median overall survival (OS) was 8.2 month (95% CI: 6.2-11.5). No statistically significant association was found between SNPs in SPARC and clinical outcome. Table 7 provides a summary of grade 3 and grade 4 adverse events.

TABLE 7

Adverse events

| Grade 3 or 4 Toxicity | Cohort A % | Cohort B % |
| --- | --- | --- |
| Neutropenia | 31 | 48 |
| Diarrhea | 13 | 12 |
| Leukopenia | 10 | 16 |
| Acneiform Rash | 15 | 8 |
| Fatigue | 10 | 4 |
| Hypertension | 5 | 12 |
| Prolonged QTC | 5 | 8 |
| Thombosis | 8 | 4 |
| Joint Pain | 5 | 4 |
| Muscle Pain | 5 | 4 |
| Anorexia | 5 | 0 |
| Dyspnea | 5 | 0 |
| Nausea | 5 | 0 |
| Pruritus | 5 | 0 |

Conclusion

Both schedules of Nab-paclitaxel with vandetanib are safe and well tolerated. The MTD for both cohorts is the maximum planned dose.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

What is claimed is:

1. A method of treating pancreatic cancer in an individual in need thereof, comprising administering to the individual an effective amount of a composition comprising nanoparticles comprising paclitaxel coated with an albumin, wherein the nanoparticles in the composition have an average diameter of no greater than about 200 nm, wherein the individual has progressed on a gemcitabine-based therapy, wherein the gemcitabine-based therapy has stopped for at least 6 months when initiating administration of the effective amount of the nanoparticle composition, and wherein the weight ratio of albumin and paclitaxel in the nanoparticle composition is about 9:1 or less.

2. A method of treating resistant or recurrent pancreatic cancer in an individual in need thereof, comprising administering to the individual an effective amount of a composition comprising nanoparticles comprising paclitaxel coated with an albumin, wherein the nanoparticles in the composition have an average diameter of no greater than about 200 nm, wherein the individual has progressed on a gemcitabine-based therapy, wherein the gemcitabine-based therapy has stopped for at least 6 months when initiating administration of the effective amount of the nanoparticle composition, and wherein the weight ratio of albumin and paclitaxel in the nanoparticle composition is about 9:1 or less.

3. A method of treating refractory pancreatic cancer in an individual in need thereof, comprising administering to the individual an effective amount of a composition comprising nanoparticles comprising paclitaxel coated with an albumin, wherein the nanoparticles in the composition have an average diameter of no greater than about 200 nm, wherein the individual has progressed on a gemcitabine-based therapy, wherein the gemcitabine-based therapy has stopped for at least 6 months when initiating administration of the effective amount of the nanoparticle composition, and wherein the weight ratio of albumin and paclitaxel in the nanoparticle composition is about 9:1 or less.

4. The method of claim 2, wherein the progression is within less than about 12 months.

5. The method of claim 2, further comprising administering to the individual an effective amount of another agent.

6. The method of claim 5, wherein the other agent is selected from the group consisting of 5-fluorouracil, erlotinib, gefitinib, marimastat, irinotecan, tipifarnib, pemetrexed, exatecan, capecitabine, raltitrexed, cetuximab, bevacizumab, bortezomib, rapamycin, vandetanib, and gemcitabine.

7. The method of claim 2, wherein the pancreatic cancer is exocrine pancreatic cancer or endocrine pancreatic cancer.

8. The method of claim 7, wherein the exocrine pancreatic cancer is pancreatic ductal carcinoma.

9. The method of claim 2, wherein the individual is human.

10. The method of claim 1, wherein the weight ratio of albumin and paclitaxel in the nanoparticle composition is about 9:1.

11. The method of claim 1, wherein the albumin is human albumin.

12. The method of claim 1, wherein the dose of paclitaxel in the nanoparticle composition is about 50 mg/m$^2$ to about 300 mg/m$^2$.

13. The method of claim 1, wherein the dose of paclitaxel in the nanoparticle composition is about 260 mg/m$^2$.

14. The method of claim 2, wherein the weight ratio of albumin and paclitaxel in the nanoparticle composition is about 9:1.

15. The method of claim 2, wherein the albumin is human albumin.

16. The method of claim 2, wherein the dose of paclitaxel in the nanoparticle composition is about 50 mg/m$^2$ to about 300 mg/m$^2$.

17. The method of claim 2, wherein the dose of paclitaxel in the nanoparticle composition is about 260 mg/m$^2$.

18. The method of claim 3, wherein the weight ratio of albumin and paclitaxel in the nanoparticle composition is about 9:1.

19. The method of claim 3, wherein the albumin is human albumin.

20. The method of claim 3, wherein the dose of paclitaxel in the nanoparticle composition is about 50 mg/m$^2$ to about 300 mg/m$^2$.

21. The method of claim 3, wherein the dose of paclitaxel in the nanoparticle composition is about 260 mg/m$^2$.

22. The method of claim 1, wherein the progression is within less than about 12 months.

23. The method of claim 1, further comprising administering to the individual an effective amount of another agent.

24. The method of claim 3, further comprising administering to the individual an effective amount of another agent.

25. The method of claim 6, wherein the other agent is gemcitabine.

26. The method of claim 23, wherein the other agent is gemcitabine.

27. The method of claim 24, wherein the other agent is gemcitabine.

28. The method of claim 25, wherein the nanoparticle composition and gemcitabine are administered sequentially to the individual.

29. The method of claim 25, wherein the nanoparticle composition and gemcitabine are both administered weekly to the individual.

30. The method of claim 25, wherein the method comprises administering about 50 mg/m$^2$ to about 250 mg/m$^2$ paclitaxel in a nanoparticle composition to the individual.

31. The method of claim 25, wherein the method comprises administering about 100 mg/m$^2$ to about 150 mg/m$^2$ paclitaxel in a nanoparticle composition to the individual.

32. The method of claim 31, wherein the nanoparticle composition and gemcitabine are both administered weekly to the individual.

33. The method of claim 25, wherein the nanoparticle composition is sterile filterable.

34. The method of claim 25, wherein the pancreatic cancer is metastatic pancreatic cancer.

35. The method of claim 26, wherein the nanoparticle composition and gemcitabine are administered sequentially to the individual.

36. The method of claim 26, wherein the nanoparticle composition and gemcitabine are both administered weekly to the individual.

37. The method of claim 26, wherein the method comprises administering about 50 mg/m$^2$ to about 250 mg/m$^2$ paclitaxel in a nanoparticle composition to the individual.

38. The method of claim 26, wherein the method comprises administering about 100 mg/m$^2$ to about 150 mg/m$^2$ paclitaxel in a nanoparticle composition to the individual.

39. The method of claim 38, wherein the nanoparticle composition and gemcitabine are both administered weekly to the individual.

40. The method of claim 26, wherein the nanoparticle composition is sterile filterable.

41. The method of claim 26, wherein the pancreatic cancer is metastatic pancreatic cancer.

42. The method of claim 27, wherein the nanoparticle composition and gemcitabine are administered sequentially to the individual.

43. The method of claim 27, wherein the nanoparticle composition and gemcitabine are both administered weekly to the individual.

44. The method of claim 27, wherein the method comprises administering about 50 mg/m$^2$ to about 250 mg/m$^2$ paclitaxel in a nanoparticle composition to the individual.

45. The method of claim 27, wherein the method comprises administering about 100 mg/m$^2$ to about 150 mg/m$^2$ paclitaxel in a nanoparticle composition to the individual.

46. The method of claim 45, wherein the nanoparticle composition and gemcitabine are both administered weekly to the individual.

47. The method of claim 27, wherein the nanoparticle composition is sterile filterable.

48. The method of claim 27, wherein the pancreatic cancer is metastatic pancreatic cancer.

* * * * *